(12) United States Patent
Grahn et al.

(10) Patent No.: US 12,415,071 B2
(45) Date of Patent: Sep. 16, 2025

(54) EPIDURAL STIMULATION AND SPINAL STRUCTURE LOCATING TECHNIQUES

(71) Applicant: Mayo Foundation for Medical Education and Research, Rochester, MN (US)

(72) Inventors: Peter J. Grahn, Rochester, MN (US); Igor A. Lavrov, Rochester, MN (US); Kristin D. Zhao, Rochester, MN (US); Kendall H. Lee, Rochester, MN (US); Megan L. Gill, Rochester, MN (US); Riazul Islam, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 280 days.

(21) Appl. No.: 17/626,319

(22) PCT Filed: Jul. 29, 2020

(86) PCT No.: PCT/US2020/044003
§ 371 (c)(1),
(2) Date: Jan. 11, 2022

(87) PCT Pub. No.: WO2021/021886
PCT Pub. Date: Feb. 4, 2021

(65) Prior Publication Data
US 2022/0241587 A1    Aug. 4, 2022

Related U.S. Application Data

(60) Provisional application No. 62/880,050, filed on Jul. 29, 2019.

(51) Int. Cl.
*A61N 1/36* (2006.01)
*A61N 1/05* (2006.01)

(52) U.S. Cl.
CPC ....... *A61N 1/36003* (2013.01); *A61N 1/0551* (2013.01)

(58) Field of Classification Search
CPC ... A61B 5/24; A61B 2562/046; A61B 5/4836; A61B 5/0006; A61B 5/05;
(Continued)

(56) References Cited

U.S. PATENT DOCUMENTS 5,002,053 A    3/1991    Garcia-Rill et al.
5,843,142 A    12/1998   Sultan
(Continued)

FOREIGN PATENT DOCUMENTS

WO    WO 2017031306    2/2017

OTHER PUBLICATIONS

EP Extended Search Report in European Appln. No. 20846513.8, dated Aug. 29, 2022, 12 pages.
(Continued)

*Primary Examiner* — Deborah L Malamud
(74) *Attorney, Agent, or Firm* — Fish & Richardson P.C.

(57) ABSTRACT

Epidural electrical stimulation (EES) systems and techniques for accessing and locating targeted spinal cord segments are disclosed. In some examples, a method includes providing a first set of electrodes of an EES system at a first set of locations on the dura mater of a spine of a mammal, the first set of locations on the dura mater corresponding to a first muscle group of the mammal; providing a second set of electrodes of the epidural electrical stimulation system at a second set of locations on the dura mater of the spine of the mammal, the second set of locations on the dura mater corresponding to a second muscle group of the mammal; and stimulating the first and second sets of locations on the dura mater by electrically energizing the first and second sets of
(Continued)

electrodes, respectively, thereby activating the first and second muscle groups in a coordinated manner.

17 Claims, 53 Drawing Sheets

(58) Field of Classification Search
CPC ............ A61B 2562/043; A61B 5/4076; A61B 5/0036; A61B 5/0082; A61B 5/00; A61N 1/05; A61N 1/0551; A61N 1/0476; A61N 1/375; A61N 1/0553; A61N 1/36185; A61N 1/08; A61N 1/0492; A61N 1/3606; A61N 1/0529; A61N 1/36062; A61N 1/3605; A61N 1/044; A61N 1/303; A61N 1/18; A61N 1/37; A61N 1/00
See application file for complete search history.

(56) References Cited

U.S. PATENT DOCUMENTS

| | | | |
|---|---|---|---|
| 6,662,053 | B2 | 12/2003 | Borkan |
| 6,839,594 | B2 | 1/2005 | Cohen et al. |
| 8,352,026 | B2 | 1/2013 | DiUbaldi |
| 9,101,769 | B2 | 8/2015 | Edgerton et al. |
| 9,358,384 | B2 * | 6/2016 | Dubuclet ................. A61N 1/05 |
| 9,409,023 | B2 | 8/2016 | Burdick et al. |
| 10,265,525 | B2 | 4/2019 | Courtine et al. |
| 2006/0069415 | A1 | 3/2006 | Cameron et al. |
| 2007/0179579 | A1 | 8/2007 | Feler et al. |
| 2009/0062883 | A1 | 3/2009 | Meadows et al. |
| 2010/0057177 | A1 | 3/2010 | Moffitt et al. |
| 2012/0123293 | A1 | 5/2012 | Shah et al. |
| 2015/0032187 | A1 | 1/2015 | Ranu et al. |
| 2015/0231396 | A1 | 8/2015 | Burdick et al. |
| 2016/0279418 | A1 | 9/2016 | Courtine et al. |
| 2017/0173326 | A1 | 6/2017 | Bloch et al. |
| 2018/0229036 | A1 | 8/2018 | Harkema et al. |
| 2020/0086116 | A1 | 3/2020 | Formento et al. |
| 2021/0052889 | A1 | 2/2021 | Grahn et al. |
| 2023/0166105 | A1 | 6/2023 | Grahn et al. |

OTHER PUBLICATIONS

Andersson et al., "Peripheral feedback mechanisms acting on the central pattern generators for locomotion in fish and cat," Can. J. Physiol. Pharmacology, 1981, 59(7):713-726.
Angeli et al., "Altering spinal cord excitability enables voluntary movements after chronic complete paralysis in humans," Brain, May 2014, 137(5):1394-1409.
Barolat, "Epidural spinal cord stimulation: anatomical and electrical properties of the intraspinal structures relevant to spinal cord stimulation and clinical correlations," Neuromodulation, Apr. 1998, 1(2):63-71.
Behrman et al., "Neuroplasticity after spinal cord injury and training: an emerging paradigm shift in rehabilitation and walking recovery," Phys. Therapy, Oct. 2006, 86(10):1406-1425.
Bozkus et al., "Comparative anatomy of the porcine and human thoracic spines with reference to thoracoscopic surgical techniques," Surg. Endoscopy, Dec. 2005, 19(12):1652-1665.
Busscher et al., "Comparative anatomical dimensions of the complete human and porcine spine," Eur. Spine Journal, Jul. 2010, 19(7):1104-1114.
Capogrosso et al., "A brain-spinal interface alleviating gait deficits after spinal cord injury in primates," Nature, Nov. 10, 2016, 539(7628):284-288.
Capogrosso et al., "A Computational Model for Epidural Electrical Stimulation of Spinal Sensorimotor Circuits," J. Neuroscience, Dec. 4, 2013, 33(49):19326-19340.
Carhart et al., "Epidural Spinal-Cord Stimulation Facilitates Recovery of Functional Walking Following Incomplete Spinal-Cord Injury," IEEE Trans. Neural Syst. Rehabil. Engineering, Mar. 2004, 12(1):32-42.

Coburn et al., "A theoretical study of epidural electrical stimulation of the spinal cord—Part I: Finite element analysis of stimulus fields," IEEE Trans. Biomed. Engineering, Nov. 1985, 32(11):971-977.
Coburn, "A theoretical study of epidural electrical stimulation of the spinal cord—Part II: Effects on long myelinated fibers," IEEE Trans. Biomed. Engineering, Nov. 1985, 32(11):978-986.
Cotterill et al., "An anatomical comparison of the human and bovine thoracolumbar spine," J. Orthop. Research, 1986, 4(3):298-303.
Courtine et al.,. "Modulation of Multisegmental Monosynaptic Responses (MMR) in a variety of leg muscles during walking and running in humans," J. Physiology, Apr. 19, 2007, 582(Pt 3):1125-1139.
Courtine et al., "Transformation of nonfunctional spinal circuits into functional states after the loss of brain input," Nat. Neuroscience, Sep. 20, 2009, 12(10):1333-1342.
Cuellar et al., "The Role of Functional Neuroanatomy of the Lumbar Spinal Cord in Effect of Epidural Stimulation," Front. Neuroanatomy, Sep. 2017, 11:82, 17 pages.
Danner et al., "Human spinal locomotor control is based on flexibly organized burst generators," Brain, Mar. 2015, 138(3):577-588.
Dath et al., "Anatomical measurements of porcine lumbar vertebrae," Clin. Biomechanics, Mar. 13, 2007, 22(5):607-613.
Dietz et al., "Restoration of sensorimotor functions after spinal cord injury," Brain, Oct. 7, 2013, 137(Pt 3):654-667.
Dimitrijevic et al., "Evidence for a Spinal Central Pattern Generator in Humans," Ann. N. Y. Acad. Sciences, Nov. 1998, 860:360-376.
Dobkin et al., "Weight-supported treadmill vs over-ground training for walking after acute incomplete SCI," Neurology, Feb. 2006, 66(4):484-493.
Dominici et al., "Versatile robotic interface to evaluate, enable and train locomotion and balance after neuromotor disorders," Nat. Medicine, Jul. 2012, 18(7):1142-1147.
Engelke et al., "Radiographic Morphometry of the Lumbar Spine in Munich Miniature Pigs," J. Am. Assoc. Lab. Anim. Science, May 1, 2016, 55(3):336-345.
Fehlings et al., "The evidence for intraoperative neurophysiological monitoring in spine surgery: does it make a difference?," Spine, Apr. 20, 2010, 35(9S):S37-S46.
Field-Fote et al., "Influence of a Locomotor Training Approach on Walking Speed and Distance in People With Chronic Spinal Cord Injury: A Randomized Clinical Trial," Phys. Therapy, Jan. 2011, 91(1):48-60.
Fong et al., "Spinal cord-transected mice learn to step in response to quipazine treatment and robotic training," J. Neuroscience, Dec. 14, 2005, 25(50):11738-11747.
Forrest et al., "Neuromotor and Musculoskeletal Responses to Locomotor Training for an Individual with Chronic Motor Complete AIS-B Spinal Cord Injury," J. Spinal Cord Medicine, Jan. 2008, 31(5):509-521.
Forssberg et al., "The locomotion of the acute spinal cat injected with clonidine i.v.," Brain Research, Feb. 1973, 50(1):184-186.
Gad et al., "Initiation of bladder voiding with epidural stimulation in paralyzed, step trained rats," PLoS One, Sep. 29, 2014, 9(9):e108184, 9 pages.
Gad et al., "Neuromodulation of motor-evoked potentials during stepping in spinal rats," J. Neurophysiology, Jun. 12, 2013, 110(6):1311-1322.
Gad et al., "Neuromodulation of the neural circuits controlling the lower urinary tract," Exp. Neurology, Jul. 2, 2016, 285(Pt B):182-189.
Gad et al., "Weight Bearing Over ground Stepping in an Exoskeleton with Non-invasive Spinal Cord Neuromodulation after Motor Complete Paraplegia," Front. Neuroscience, Jun. 2017, 11:333, 8 pages.
Gerasimenko et al., "Epidural Spinal Cord Stimulation Plus Quipazine Administration Enable Stepping in Complete Spinal Adult Rats," J. Neurophysiology, Nov. 2007, 98(5):2525-2536.
Gerasimenko et al., "Initiation of Locomotor Activity in Spinal Cats by Epidural Stimulation of the Spinal Cord," Neurosci. Behav. Physiology, Mar. 2003, 33(3):247-254.

(56) References Cited

OTHER PUBLICATIONS

Gerasimenko et al., "Initiation of locomotor activity in spinalized cats by means of spinal cord epidural stimulation," Ross Fiziol Zh Im I M Sechenova, Sep. 2001, 87(9):1161-1170 (with English Abstract).
Gerasimenko et al., "Noninvasive Reactivation of Motor Descending Control after Paralysis," J. Neurotrauma, Dec. 2015, 32(24):1968-1980.
Gerasimenko et al., "Spinal cord reflexes induced by epidural spinal cord stimulation in normal awake rats," J. Neurosci. Methods, Oct. 2006, 157(2):253-263.
Gill et al., "Neuromodulation of lumbosacral spinal networks enables independent stepping after complete paraplegia," Nat. Medicine, Nov. 2018, 24(11):1677-1682.
Grahn et al., "Enabling Task-Specific Volitional Motor Functions via Spinal Cord Neuromodulation in a Human With Paraplegia," Mayo Clin. Proceedings, Apr. 2017, 92(4):544-554.
Grahn et al., "Motor-evoked responses via epidural spinal cord stimulation evaluated at intra- and inter-segmental resolution," Poster, Presented at Proceedings of the NANS2-NIC Joint Meeting, Baltimore, MD, Jun. 25-29, 2016, 1 page.
Grahn et al., "MRI-Guided Stereotactic System for Delivery of Intraspinal Microstimulation," Spine, Jul. 1, 2016, 41(13):E806-E813.
Grillner et al., "Activation of NMDA-receptors elicits "fictive locomotion" in lamprey spinal cord in vitro," Acta Physiol. Scandinavica, Dec. 1981, 113(4):549-551.
Guiho et al., "Impact of direct epispinal stimulation on bladder and bowel functions in pigs: A feasibility study," Neurourol. Urodynamics, Jun. 12, 2017, 37(1):138-147.
Hachmann et al., "Electrical Neuromodulation of the Respiratory System After Spinal Cord Injury," Mayo Clin. Proceedings, Aug. 3, 2017, 92(9):1401-1414.
Hachmann et al., "Large Animal Model for Development of Functional Restoration Paradigms Using Epidural and Intraspinal Stimulation," PLoS One, Dec. 2013, 8(12):e81443, 7 pages.
Hachmann et al., "Review of Epidural Spinal Cord Stimulation for Augmenting Cough after Spinal Cord Injury," Front. Hum. Neuroscience, Mar. 28, 2017, 11:144, 10 pages.
Harkema et al., "Balance and Ambulation Improvements in Individuals With Chronic Incomplete Spinal Cord Injury Using Locomotor Training-Based Rehabilitation," Arch. Phys. Med. Rehabilitation, Sep. 2012, 93(9):1508-1517.
Harkema et al., "Effect of epidural stimulation of the lumbosacral spinal cord on voluntary movement, standing, and assisted stepping after motor complete paraplegia: a case study," Lancet, Jun. 4, 2011, 377(9781)1938-1947.
Harkema et al., "Locomotor Training: As a Treatment of Spinal Cord Injury and in the Progression of Neurologic Rehabilitation," Arch. Phys. Med. Rehabilitation, Sep. 2012, 93(9):1588-1597.
Holsheimer et al., "How do geometric factors influence epidural spinal cord stimulation? A quantitative analysis by computer modeling," Stereotact. Func. Neurosurgery, 1991, 56(4):234-249.
Holsheimer, "Computer modelling of spinal cord stimulation and its contribution to therapeutic efficacy," Spinal Cord, Aug. 1998, 36(8):531-541.
Holsheimer, "Which neuronal elements are activated directly by spinal cord stimulation," Neuromodulation, Jan. 2002, 5(1):25-31.
Ichiyama et al., "Hindlimb stepping movements in complete spinal rats induced by epidural spinal cord stimulation," Neurosci. Letters, Aug. 2005, 383(3):339-344.
Iwahara et al., "Spinal cord stimulation-induced locomotion in the adult cat," Brain Res. Bulletin, Jan. 1992, 28(1):99-105.
Kandziora et al., "Comparison between sheep and human cervical spines: an anatomic, radiographic, bone mineral density, and biomechanical study," Spine, May 1, 2001, 26(9):1028-1037.
Kettler et al., "Are the spines of calf, pig and sheep suitable models for pre-clinical implant tests?," Eur. Spine Journal, Aug. 25, 2007, 16(12):2186-2192.
Kirazli et al., "Anatomy of the spinal dorsal root entry zone: its clinical significance," Acta Neurochirurgica, Oct. 21, 2014, 156(12):2351-2358.
Ko et al., "Gross quantitative measurements of spinal cord segments in human," Spinal Cord, Jan. 2004, 42(1):35-40.
Kowalski et al., "Diaphragm activation via high frequency spinal cord stimulation in a rodent model of spinal cord injury," Exp. Neurology, Mar. 13, 2013, 247:689-693.
Kowalski et al., "High frequency spinal cord stimulation—New method to restore cough," Respir. Physiol. Neurobiology, Jul. 6, 2016, 232:54-56.
Kowalski et al., "Safety assessment of epidural wire electrodes for cough production in a chronic pig model of spinal cord injury," J. Neurosci. Methods, May 7, 2016, 268:98-105.
Ladenbauer et al., "Stimulation of the human lumbar spinal cord with implanted and surface electrodes: A computer simulation study," IEEE Trans. Neural Sys. Rehabil. Engineering, Dec. 2010, 18(6):637-645.
Lavrov et al., "Activation of spinal locomotor circuits in the decerebrated cat by spinal epidural and/or intraspinal electrical stimulation," Brain Research, Mar. 2015, 1600(C):84-92.
Lavrov et al., "Epidural Stimulation Induced Modulation of Spinal Locomotor Networks in Adult Spinal Rats," J. Neuroscience, Jun. 2008, 28(23):6022-6029.
Lavrov et al., "Facilitation of stepping with epidural stimulation in spinal rats: role of sensory input," J. Neuroscience, Jul. 30, 2008, 28(31):7774-7780.
Lavrov et al., "Integrating multiple sensory systems to modulate neural networks controlling posture," J. Neurophysiology, Oct. 7, 2015, 114(6):3306-3314.
Lavrov et al., "Plasticity of Spinal Cord Reflexes After a Complete Transection in Adult Rats: Relationship to Stepping Ability," J. Neurophysiology, Oct. 2006, 96(4):1699-1710.
Lavrov et al., "The Role of Functional Neuroanatomy of the Lumbar Spinal Cord in Effect of Epidural Stimulation," Front. Neuroanatomy, Sep. 2017, 11:82, 17 pages.
Lee et al., "A novel porcine model of traumatic thoracic spinal cord injury," J. Neurotrauma, Jan. 14, 2013, 30(3):142-159.
Lempka et al., "Computational analysis of kilohertz frequency spinal cord stimulation for chronic pain management," Anesthesiology, Jun. 2015, 122(6):1362-1376.
Lu et al., "Engaging Cervical Spinal Cord Networks to Reenable Volitional Control of Hand Function in Tetraplegic Patients," Neurorehabil. Neural Repair, Nov. 2016, 30(10):951-962.
McLain et al., "Comparative morphometry of L4 vertebrae: comparison of large animal models for the human lumbar spine," Spine, Apr. 15, 2002, 27(8):200-206.
Minassian et al., "Stepping-like movements in humans with complete spinal cord injury induced by epidural stimulation of the lumbar cord: electromyographic study of compound muscle action potentials," Spinal Cord, Jul. 2004, 42(7):401-416.
Minassian et al., "Targeting Lumbar Spinal Neural Circuitry by Epidural Stimulation to Restore Motor Function After Spinal Cord Injury," Neurotherapeutics, Apr. 2016, 13(2):284-294.
Moraud et al., "Mechanisms Underlying the Neuromodulation of Spinal Circuits for Correcting Gait and Balance Deficits after Spinal Cord Injury," Neuron, Feb. 4, 2016, 89(4):814-828.
Murg et al., "Epidural electrical stimulation of posterior structures of the human lumbar spinal cord: 1. Muscle twitches—a functional method to define the site of stimulation," Spinal Cord, Jul. 2000, 38(7):394-402.
Musienko et al., "Multi-system neurorehabilitative strategies to restore motor functions following severe spinal cord injury," Exp. Neurology, May 2012, 235(1):100-109.
Nandra et al., "A Parylene-based microelectrode array implant for spinal cord stimulation in rats," Conf. Proc. IEEE Eng. Med. Biol. Society, Aug. 11, 2011, 2011:1007-1010.
National Spinal Cord Injury Statistical Center, "Spinal cord injury facts and figures at a glance," J. Spinal Cord Medicine, Sep. 2014, 37(5):659-660.
Navarro et al., "Chronic Spinal Compression Model in Minipigs: A Systematic Behavioral, Qualitative, and Quantitative Neuropathological Study," J. Neurotrauma, Jan. 13, 2012, 29(3):499-513.

(56) References Cited

OTHER PUBLICATIONS

Ney et al., "Cost-effectiveness of intraoperative neurophysiological monitoring for spinal surgeries: beginning steps," Clin. Neurophysiology, Mar. 3, 2012, 123(9):1705-1707.
PCT International Preliminary Report on Patentability in International Appln. No. PCT/US2019/014757, dated Jul. 28, 2020, 6 pages.
PCT International Preliminary Report on Patentability in International Appln. No. PCT/US2020/044003, dated Feb. 1, 2022, 7 pages.
PCT International Search Report and Written Opinion in International Appln. No. PCT/US2019/014757, dated Jun. 3, 2019, 9 pages.
PCT International Search Report and Written Opinion in International Appln. No. PCT/US2020/044003, dated Jan. 7, 2021, 10 pages.
Pettigrew et al., "Epidural Spinal Stimulation to Improve Bladder, Bowel, and Sexual Function in Individuals With Spinal Cord Injuries: A Framework for Clinical Research," IEEE Trans. Biomed. Engineering, Feb. 2017, 64(2):253-262.
Pleticha et al., "Pig lumbar spine anatomy and imaging-guided lateral lumbar puncture: A new large animal model for intrathecal drug delivery," J. Neurosci. Methods, Mar. 19, 2013, 216(1):10-15.
Rattay et al., "Epidural electrical stimulation of posterior structures of the human lumbosacral cord: 2. Quantitative analysis by computer modeling," Spinal Cord, Aug. 2000, 38(8):473-489.
Rattay et al., "Finite Element Modeling for Extracellular Stimulation," In: Encyclopedia of Computational Neuroscience, Jaeger et al. (eds.), Mar. 4, 2014, 12 pages.
Rejc et al., "Effects of Lumbosacral Spinal Cord Epidural Stimulation for Standing after Chronic Complete Paralysis in Humans," PLoS One, Jul. 2015, 10(7):e0133998, 20 pages.
Rejc et al., "Effects of Stand and Step Training with Epidural Stimulation on Motor Function for Standing in Chronic Complete Paraplegics," J. Neurotrauma, May 2017, 34(9):1787-1802.
Sayenko et al., "Effects of paired transcutaneous electrical stimulation delivered at single and dual sites over lumbosacral spinal cord," Neurosci. Letters, Nov. 2015, 609(C):229-234.
Sayenko et al., "Neuromodulation of evoked muscle potentials induced by epidural spinal-cord stimulation in paralyzed individuals," J. Neurophysiology, Mar. 2014, 111(5):1088-1099.
Sayenko et al., "Spinal segment-specific transcutaneous stimulation differentially shapes activation pattern among motor pools in humans," J. Appl. Physiology, Jun. 2015, 118(11):1364-1374.
Schomberg et al., "Translational relevance of Swine Model of Spinal Cord Injury," J. Neurotrauma, Aug. 25, 2016, 34(3):541-551.
Shah et al., "Spinal epidural stimulation strategies: clinical implications of locomotor studies in spinal rat," Neuroscientist, Mar. 26, 2017, 23(6):664-680.
Shah et al., "Unique Spatiotemporal Neuromodulation of the Lumbosacral Circuitry Shapes Locomotor Success after Spinal Cord Injury," J. Neurotrauma, Sep. 2016, 33(18):1709-1723.
Sheng et al., "Anatomy of large animal spines and its comparison to the human spine: A systematic review," Eur. Spine Journal, Oct. 30, 2009, 19(1):46-56.
Sheng et al., "Comparison of cervical spine anatomy in calves, pigs and humans," PLoS One, Feb. 11, 2016, 11(2):e0148610, 10 pages.
Stecker, "A review of intraoperative monitoring for spinal surgery," Surg. Neurol. International, Jul. 17, 2012, 3(Suppl 3):S174-S187.
Struijk et al., "Excitation of Dorsal Root Fibers in Spinal Cord Stimulation: A Theoretical Study," IEEE Trans. Biomed. Engineering, Jul. 1993, 40(7):632-639.
Toossi et al., "Mechanically Stable Intraspinal Microstimulation Implants for Human Translation," Ann. Biomed. Engineering, Aug. 25, 2016, 45(3):681-694.
van den Brand et al., "Restoring Voluntary Control of Locomotion after Paralyzing Spinal Cord Injury," Science, Jun. 2012, 336(6085):1182-1185.
Wenger et al., "Spatiotemporal neuromodulation therapies engaging muscle synergies improve motor control after spinal cord injury," Nat. Medicine, Feb. 2016, 22(2):138-145.
Wilke et al., "Anatomy of the sheep spine and its comparison to the human spine," Anat. Record, Apr. 1997, 247(4):542-555.
Yingling et al., "The porcine cervical spine as a model of the human lumbar spine: an anatomical, geometric, and functional comparison," J. Spinal Disorders, Oct. 1999, 12(5):415-423.
Yushkevich et al., "User-guided 3D active contour segmentation of anatomical structures: significantly improved efficiency and reliability," NeuroImage, Mar. 20, 2006, 31(3):1116-1128.
Zurita et al., "The pig model of chronic paraplegia: A challenge for experimental studies in spinal cord injury," Prog. Neurobiology, May 5, 2012, 97(3):288-303.
Behrman et al., "Locomotor training after human spinal cord injury: a series of case studies, " Phys. Ther., Jul. 2000, 80(7):688-700.
ClinicalTrials.gov [online], "Spinal Cord Injury Epidural Stimulation," NCT02592668, Jan. 2016, last updated Apr. 2020, retrieved from URL<https://www.clinicaltrials.gov/study/NCT02592668>, 11 pages.
Courtine et al., "Defining ecological strategies in neuroprosthetics," Neuron, Apr. 2015, 86(1):29-33.
Dimitrijevic et al., "EMG evidence of suprasegmental infuence on motor unit activity in paralyzed muscles," Clin. Neurophysiol., 1983, 56:S68.
Dimitrijevic et al., "Human Spinal Cord Motor Control That is Partially or Completely Disconnected from the Brain," Am. J. Neuroprot. Neuroregen., Oct. 2016, 8(1):12-26.
Dimitrijevic, "Residual motor functions in spinal cord injury," Adv. Neurol., 1988, 47:138-155.
Huang et al., "Modulation effects of epidural spinal cord stimulation on muscle activities during walking, " IEEE Trans. Neural. Syst. Rehabil. Eng., Mar. 2006, 14(1):14-23.
Kakulas, "Pathology of spinal injuries," Cent. Nerv. Syst. Trauma, Jan. 1984, 1(2):117-129.
Minassian et al., "Spinal Cord Stimulation and Augmentative Control Strategies for Leg Movement after Spinal Paralysis in Humans," CNS Neurosci. Ther., Apr. 2016, 22(4):262-270.
Moritz, "Now is the Critical Time for Engineered Neuroplasticity," Neurotherapeutics, Jul. 2018, 15(3):628-634.
Shah et al., "Variability in step training enhances locomotor recovery after a spinal cord injury, " Eur. J. Neurosci., Jul. 2012, 36(1):2054-2062.
Sherwood et al., "Evidence of subclinical brain influence in clinically complete spinal cord injury: discomplete Sci," J. Neurol. Sci., Jul. 1992, 110(1-2):90-98.
Taccola et al., "And yet it moves: Recovery of volitional control after spinal cord injury," Prog. Neurobiol., Jan. 2018, 160:64-81.
Wenger et al., "Closed-loop neuromodulation of spinal sensorimotor circuits controls refined locomotion after complete spinal cord injury," Sci. Transl. Med., Sep. 2014, 6(255):255ra133.
Anderson et al., "Astrocyte scar formation aids central nervous system axon regeneration," Nature, Apr. 2016, 532(7598):195-200.
Angeli et al., "Recovery of Over-Ground Walking after Chronic Motor Complete Spinal Cord Injury," N. Engl. J. Med., Sep. 2018, 379(13):1244-1250.
Bydon et al., "The current role of steroids in acute spinal cord injury," World Neurosurg., Nov. 2014, 82(5):848-854.
Calvert et al., "Electrophysiological Guidance of Epidural Electrode Array Implantation over the Human Lumbosacral Spinal Cord to Enable Motor Function after Chronic Paralysis," J. Neurotrauma, May 2019, 36(9):1451-1460.
Chen et al., "GDNF Schwann cells in hydrogel scaffolds promote regional axon regeneration, remyelination and functional improvement after spinal cord transection in rats," J. Tissue Eng. Regen. Med., Jan. 2018, 12(1):e398-e407.
Collinger et al., "High-performance neuroprosthetic control by an individual with tetraplegia," Lancet, Feb. 2013, 381(9866):557-564.
Flesher et al., "Intracortical microstimulation of human somatosensory cortex," Sci. Transl. Med., Oct. 2016, 8(361):361ra141.
Gerasimenko et al., "Transcutaneous electrical spinal-cord stimulation in humans," Ann. Phys. Rehabil. Med., Sep. 2015, 58(4):225-231.
Harkema et al., "Normalization of Blood Pressure With Spinal Cord Epidural Stimulation After Severe Spinal Cord Injury," Front. Hum. Neurosci., Mar. 2018, 12:83.

(56) References Cited

OTHER PUBLICATIONS

Harvey, "Physiotherapy rehabilitation for people with spinal cord injuries," J. Physiother., Jan. 2016, 62(1):4-11.
Ichiyama et al., "Step training reinforces specific spinal locomotor circuitry in adult spinal rats," J. Neurosci., Jul. 2008, 28(29):7370-7375.
Kirshblum et al., "Reference for the 2011 revision of the international standards for neurological classification of spinal cord injury," J. Spinal Cord Med., Nov. 2011, 34(6):547-554.
Lang et al., "Modulation of the proteoglycan receptor PTPσ promotes recovery after spinal cord injury," Naure, Feb. 2015, 518(7539):404-408.
Minassian et al., "Human lumbar cord circuitries can be activated by extrinsic tonic input to generate locomotor-like activity," Hum. Mov. Sci., Apr. 2007, 26(2):275-295.
Rejc et al., "Motor recovery after activity-based training with spinal cord epidural stimulation in a chronic motor complete paraplegic," Sci. Rep., Oct. 2017, 7(1):13476.
Sekhon et al., "Epidemiology, demographics, and pathophysiology of acute spinal cord injury," Spine, Dec. 2001, 26(24 Suppl):S2-S12.
Terson de Paleville et al., "Epidural stimulation with locomotor training improves body composition in individuals with cervical or upper thoracic motor complete spinal cord injury: A series of case studies," J. Spinal Cord Med., Jan. 2019, 42(1):32-38.
West et al., "Association of Epidural Stimulation With Cardiovascular Function in an Individual With Spinal Cord Injury," JAMA Neurol., May 2018, 75(5):630-632.

\* cited by examiner

Week 4 of EES + MMR
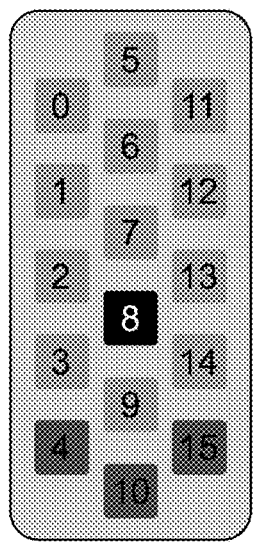
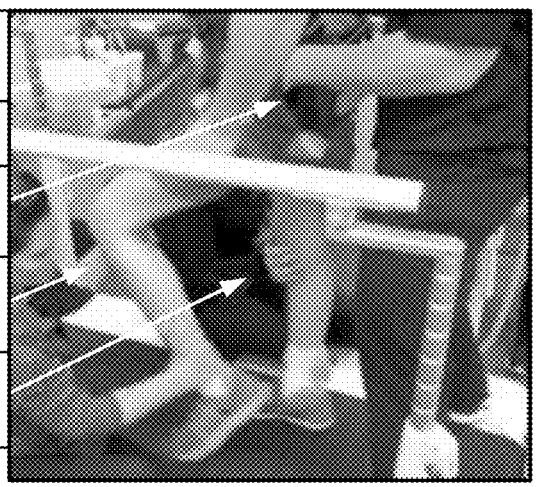
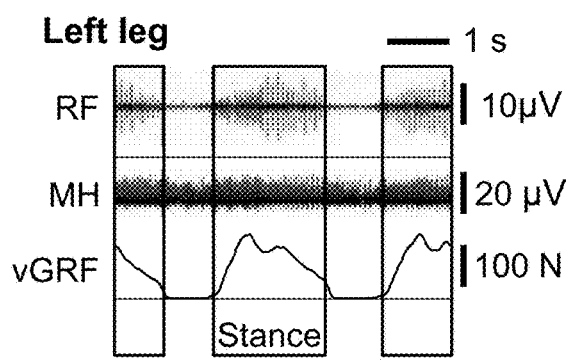
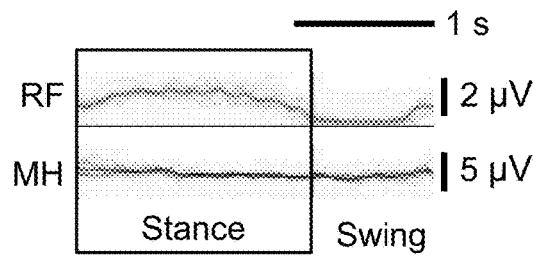
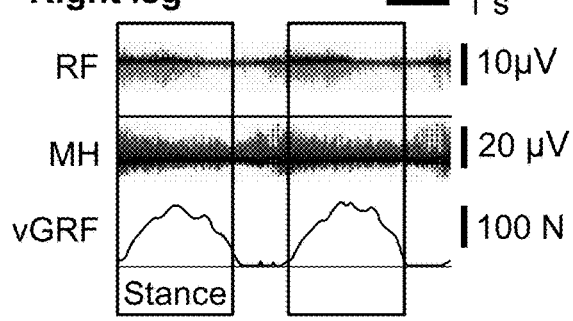
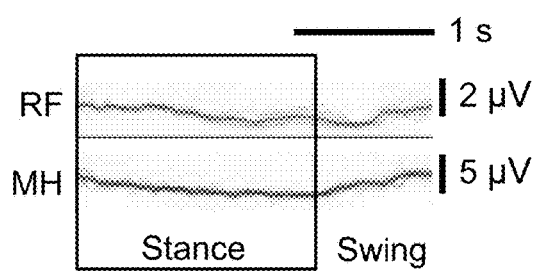
FIGS. 4A-4J E
Muscle activity normalized to step cycle average (10 step cycles)
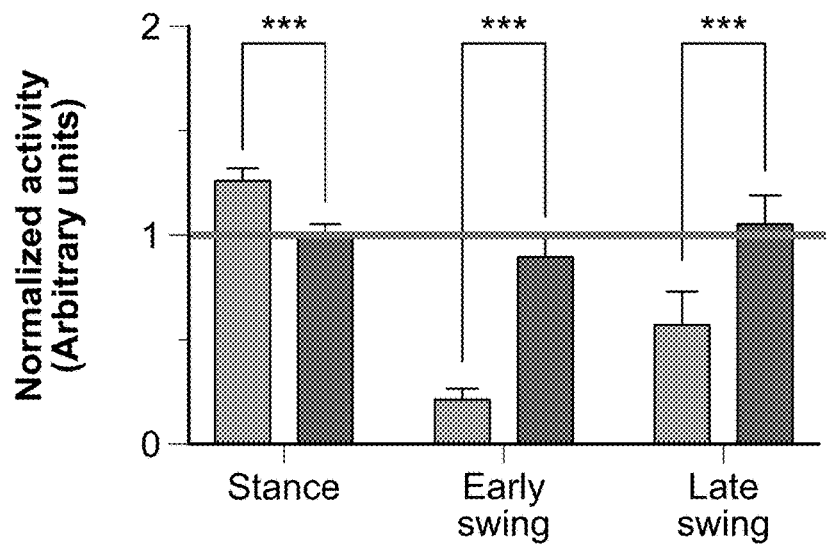
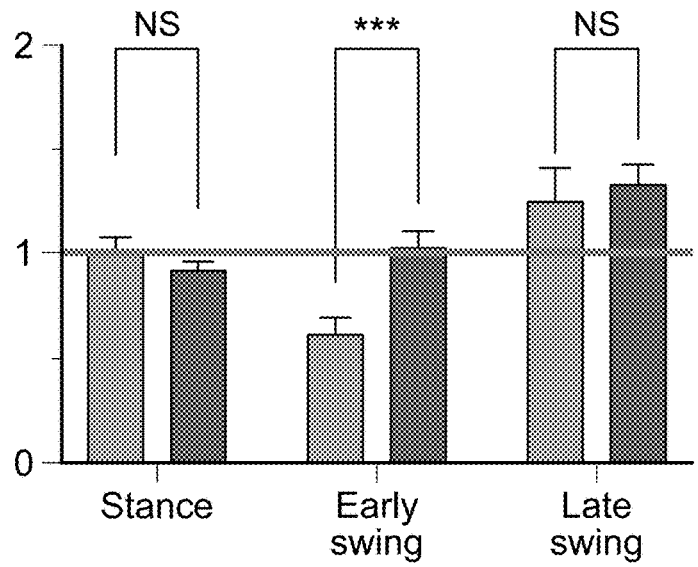
FIGS. 4A-4J (Cont. 1)

F Week 43 of EES + MMR
Two interleaved EES programs
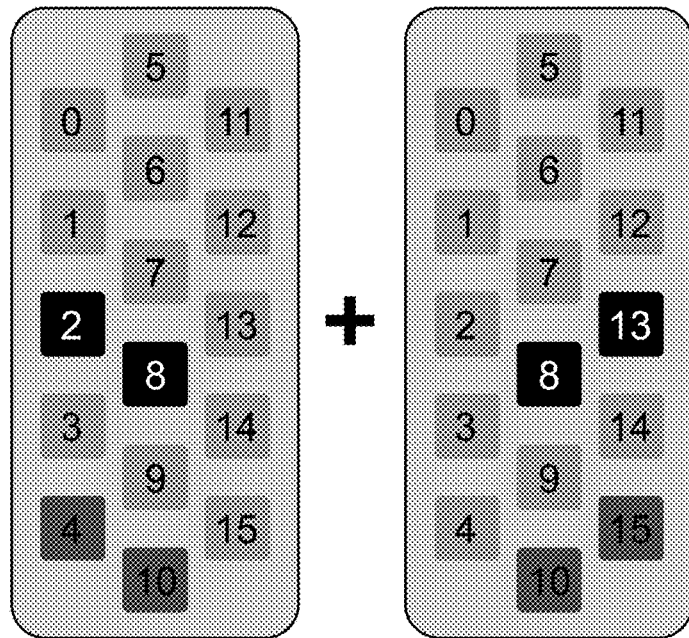
210 µs
20 Hz
3.3 V
210 µs
20 Hz
3.7 V
G
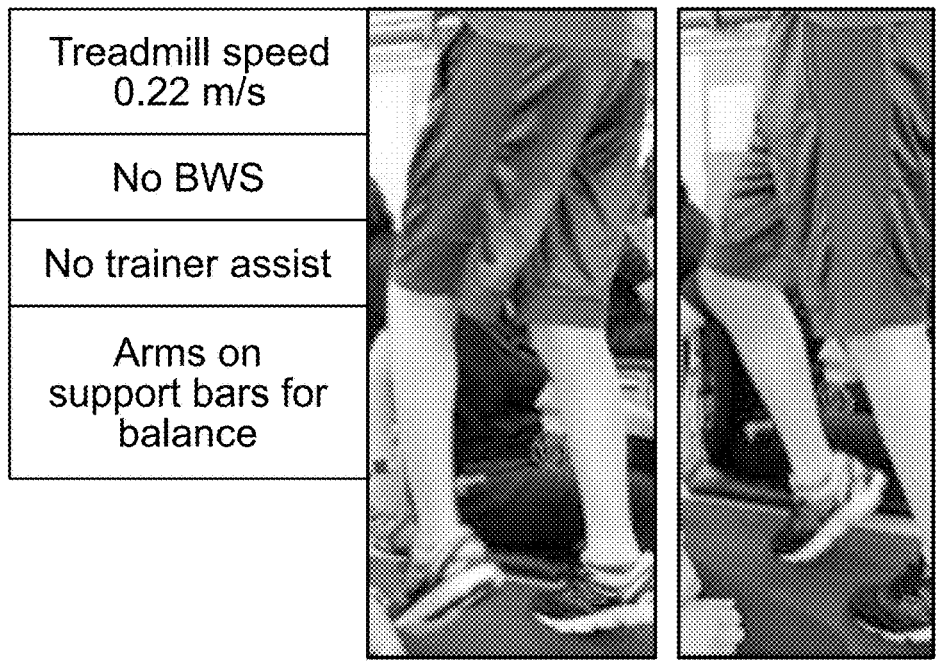
Treadmill speed 0.22 m/s
No BWS
No trainer assist
Arms on support bars for balance
FIGS. 4A-4J (Cont. 2)

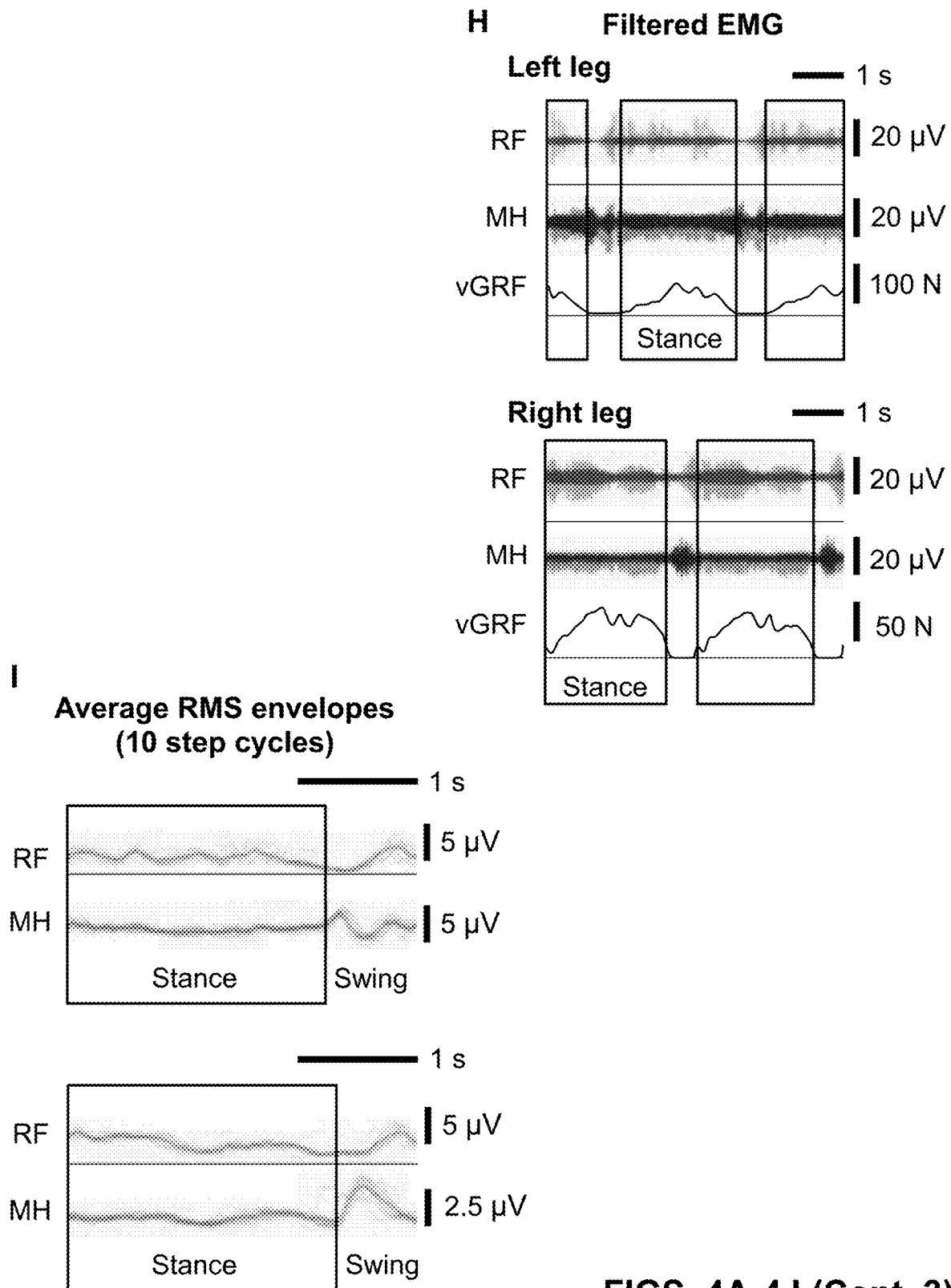
FIGS. 4A-4J (Cont. 3)

J
Muscle activity normalized to step cycle average (10 step cycles)
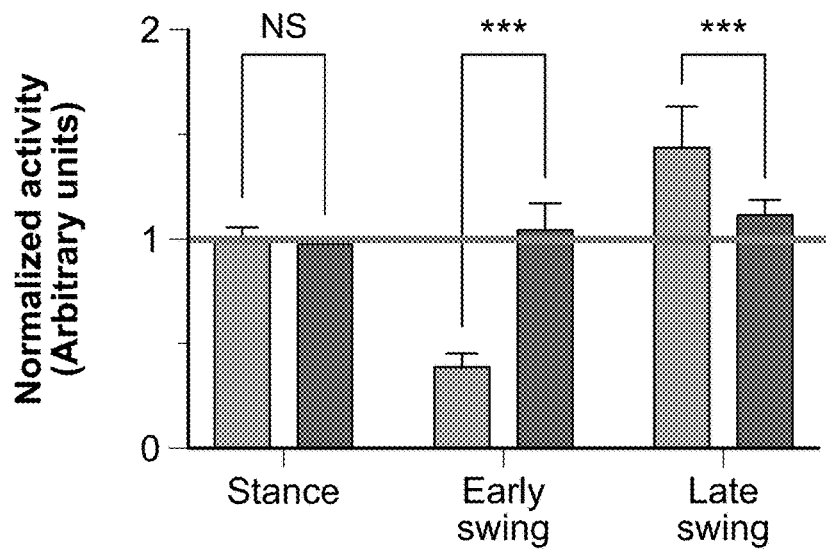
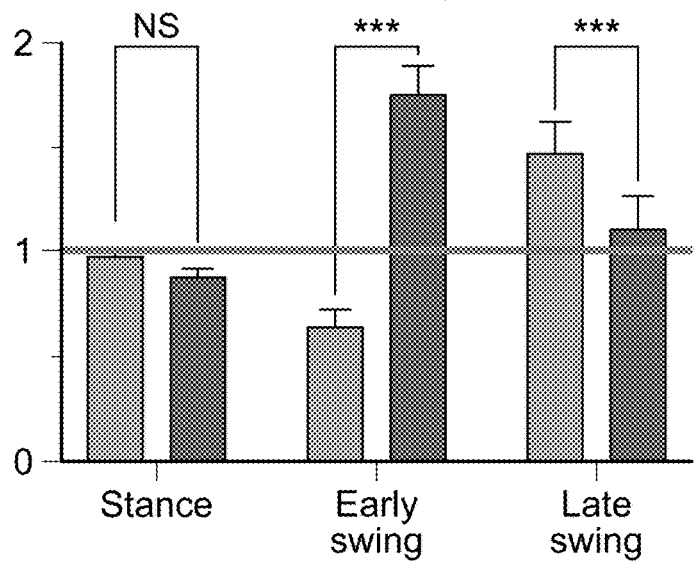
FIGS. 4A-4J (Cont. 4)

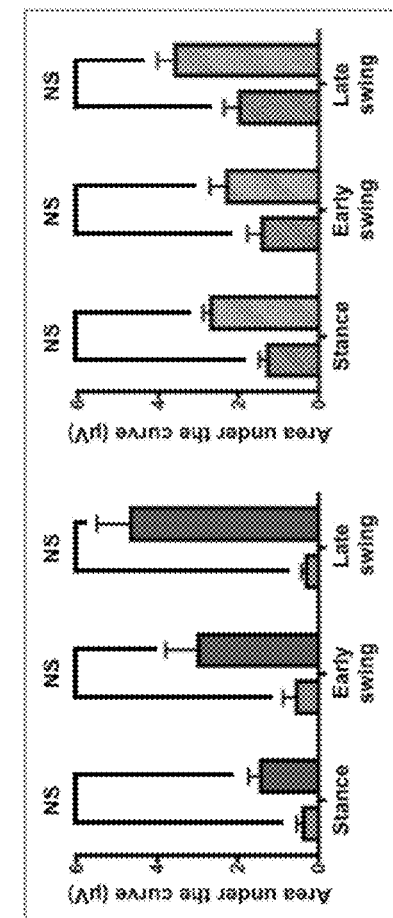
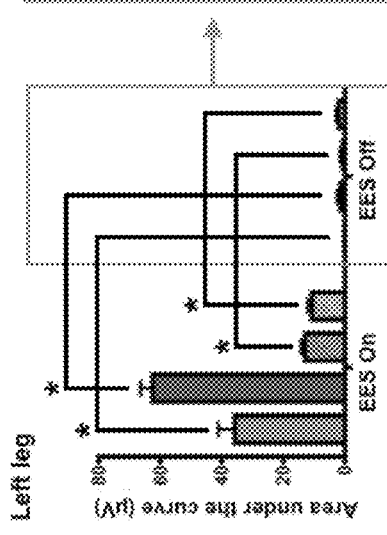
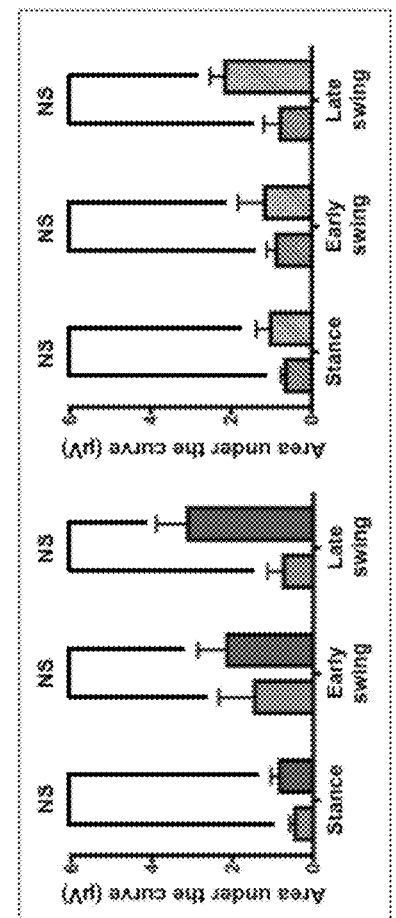
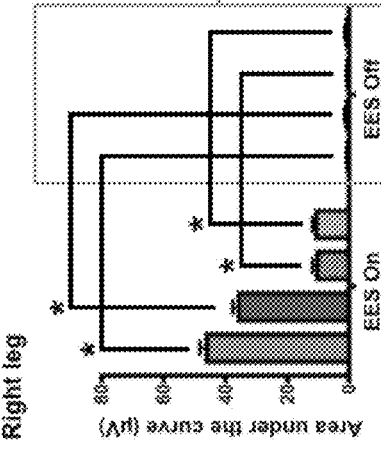
FIGS. 5A-5C (Cont.)

Week 16 of EES + MMR
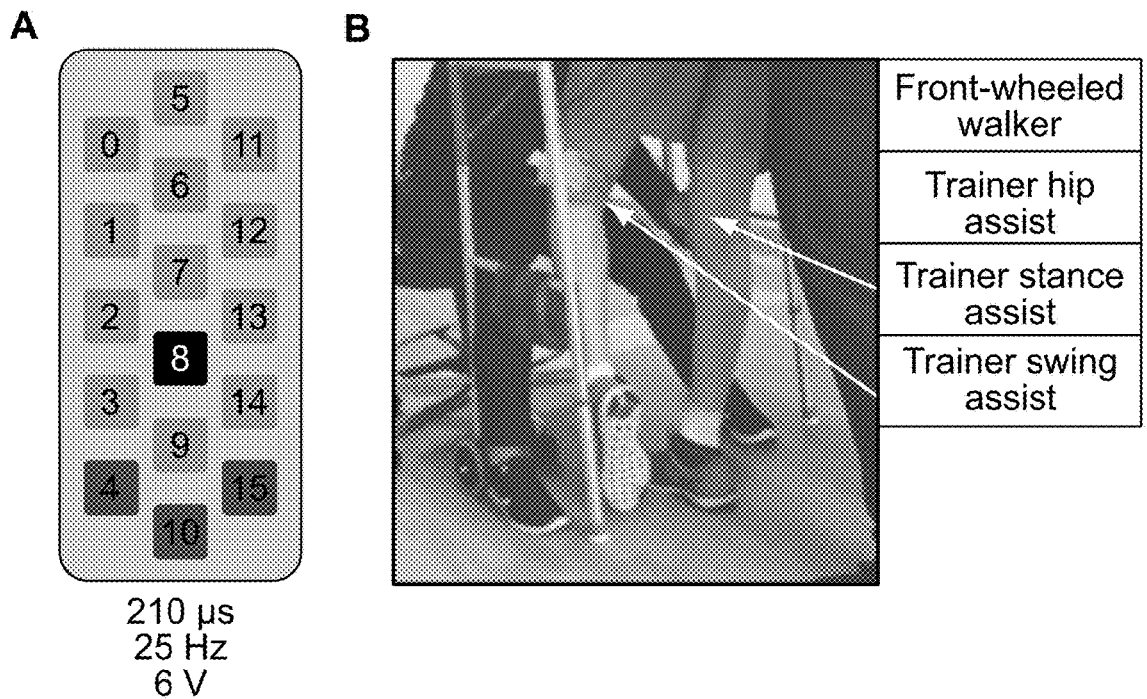
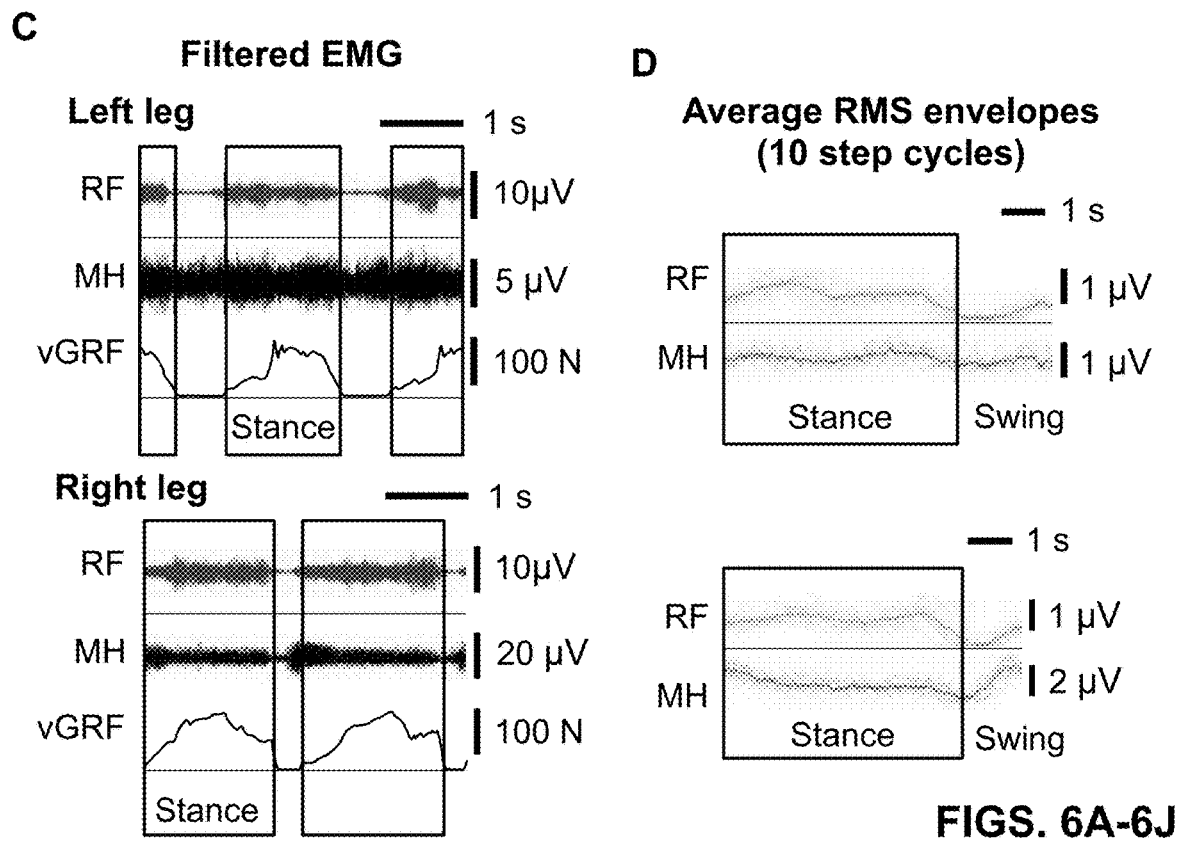
FIGS. 6A-6J

E
Muscle activity normalized to step cycle average (10 step cycles)
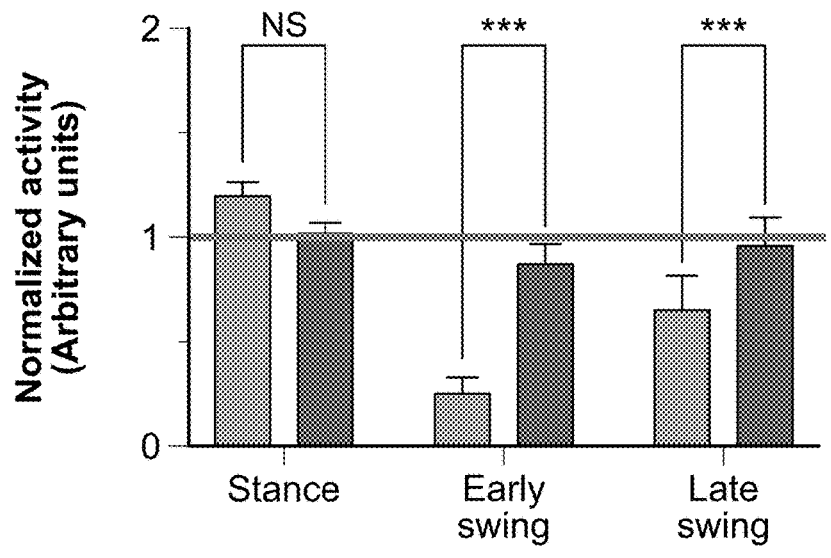
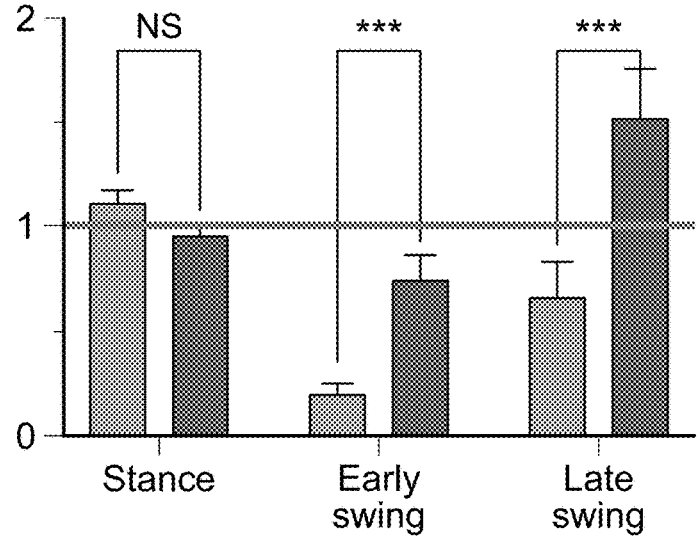
FIGS. 6A-6J (Cont. 1)

F Week 43 of EES + MMR
Two interleaved EES programs
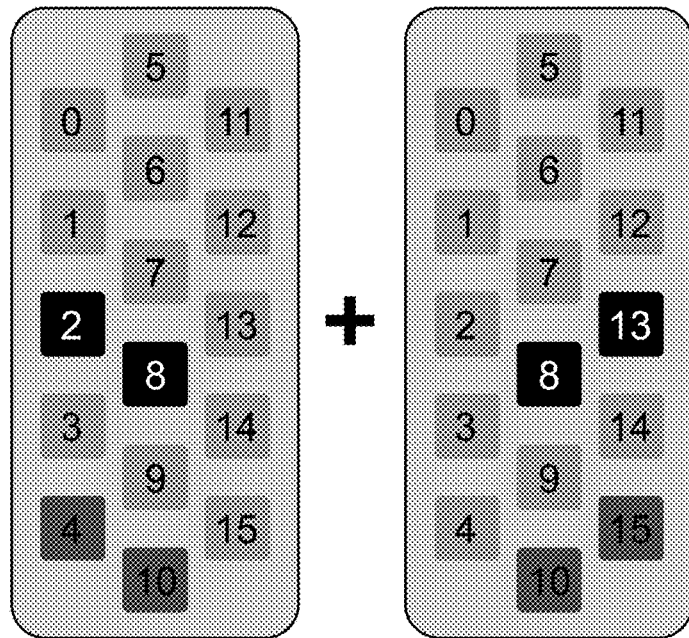
210 μs    210 μs
20 Hz     20 Hz
3.4 v     3.8 v
G
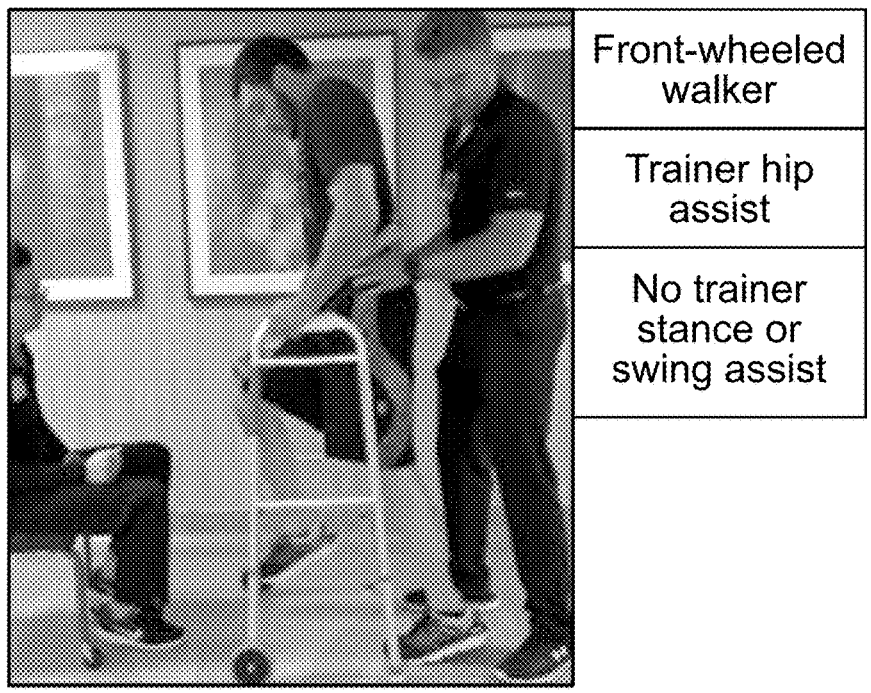
| Front-wheeled walker |
| Trainer hip assist |
| No trainer stance or swing assist |
FIGS. 6A-6J (Cont. 2)

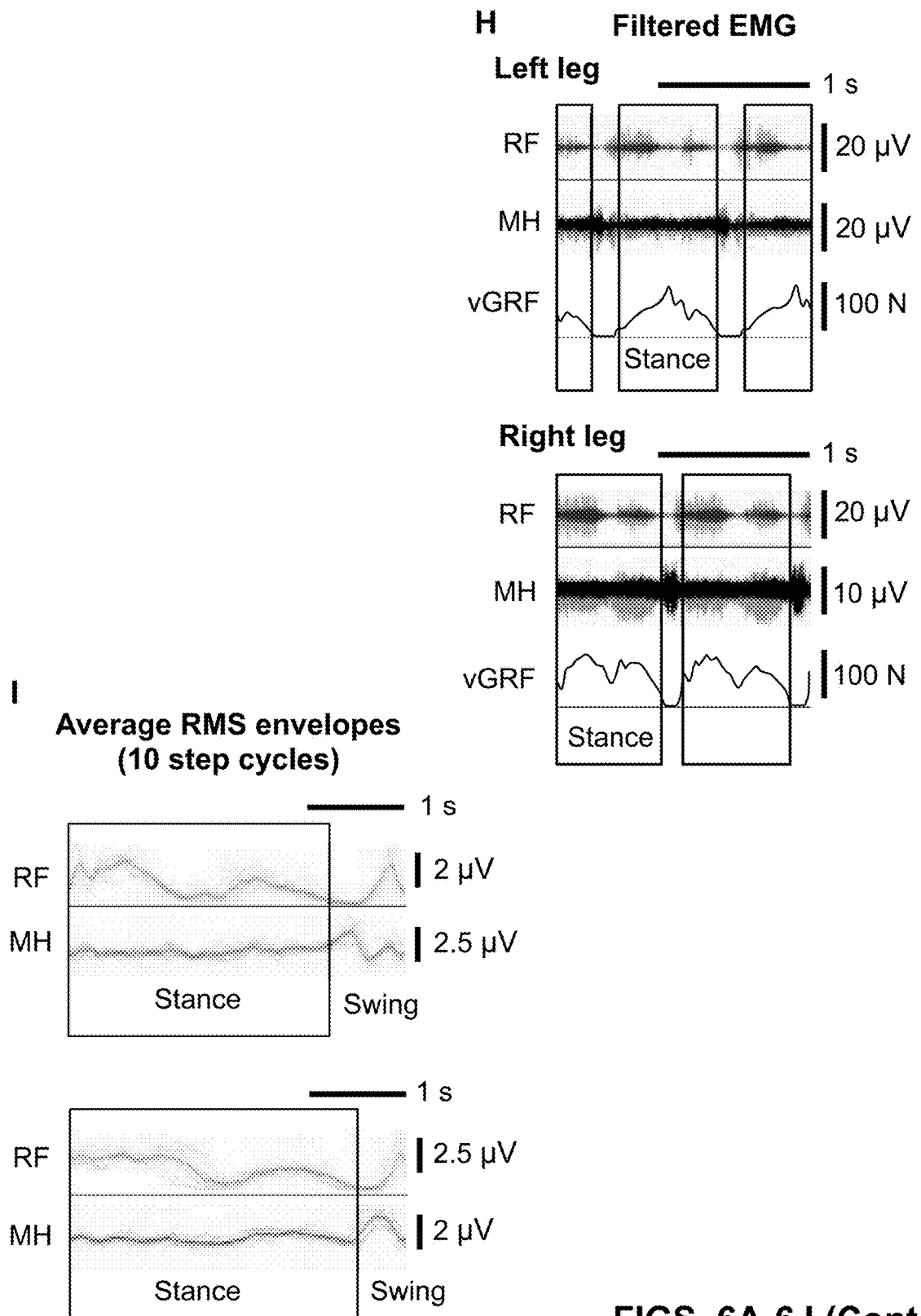
FIGS. 6A-6J (Cont. 3)

J
Muscle activity normalized to step cycle average (10 step cycles)
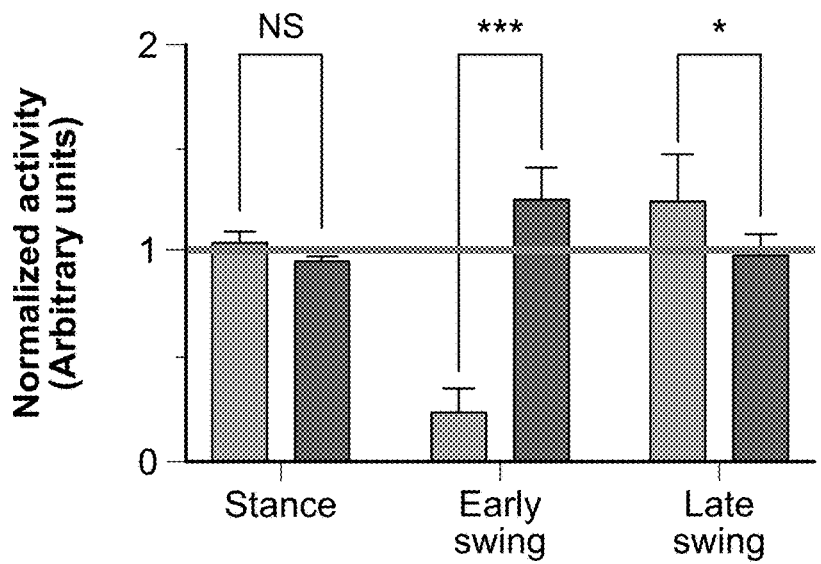
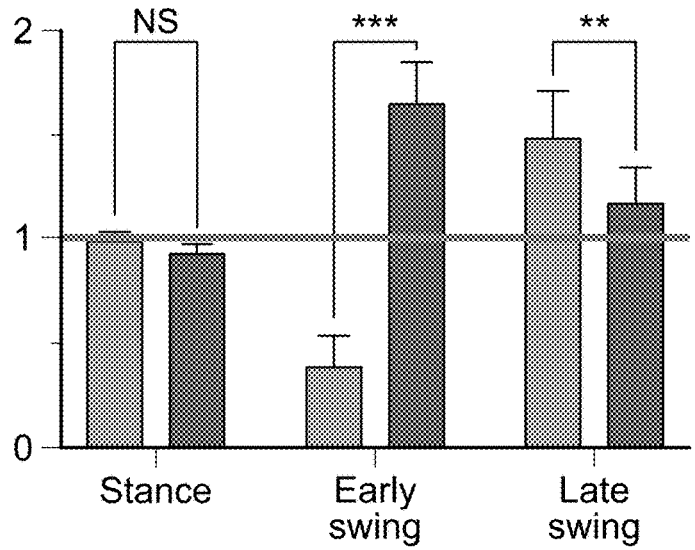
FIGS. 6A-6J (Cont. 4)

ES 100 Rostral Configuration
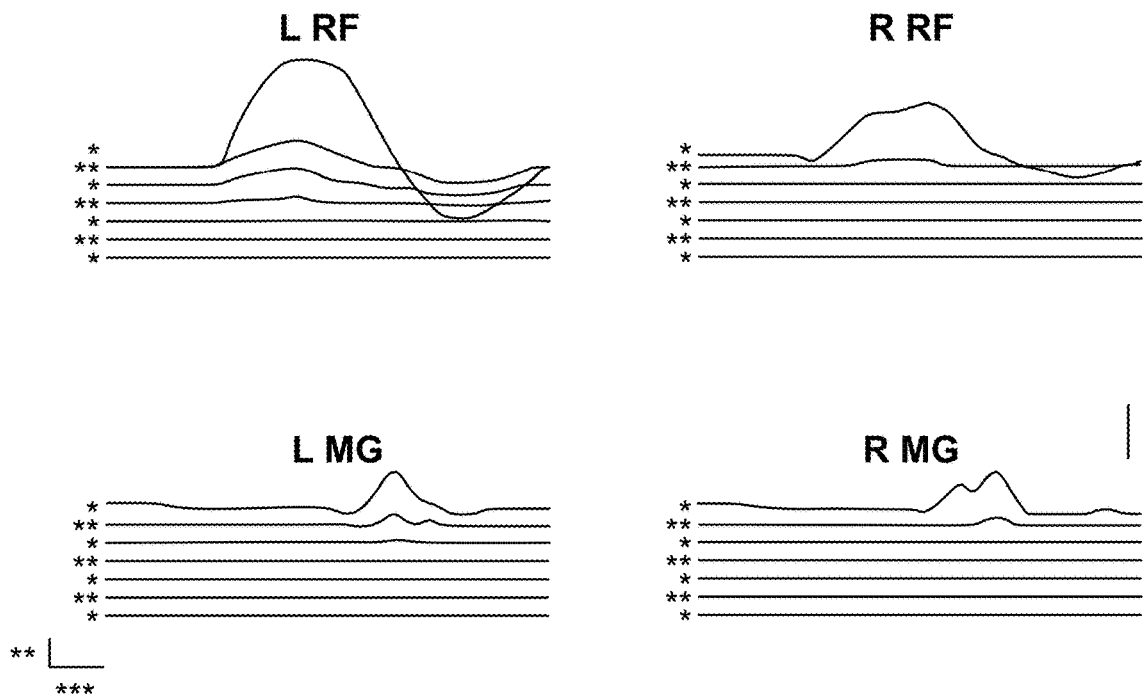
ES 100 Caudal Configuration
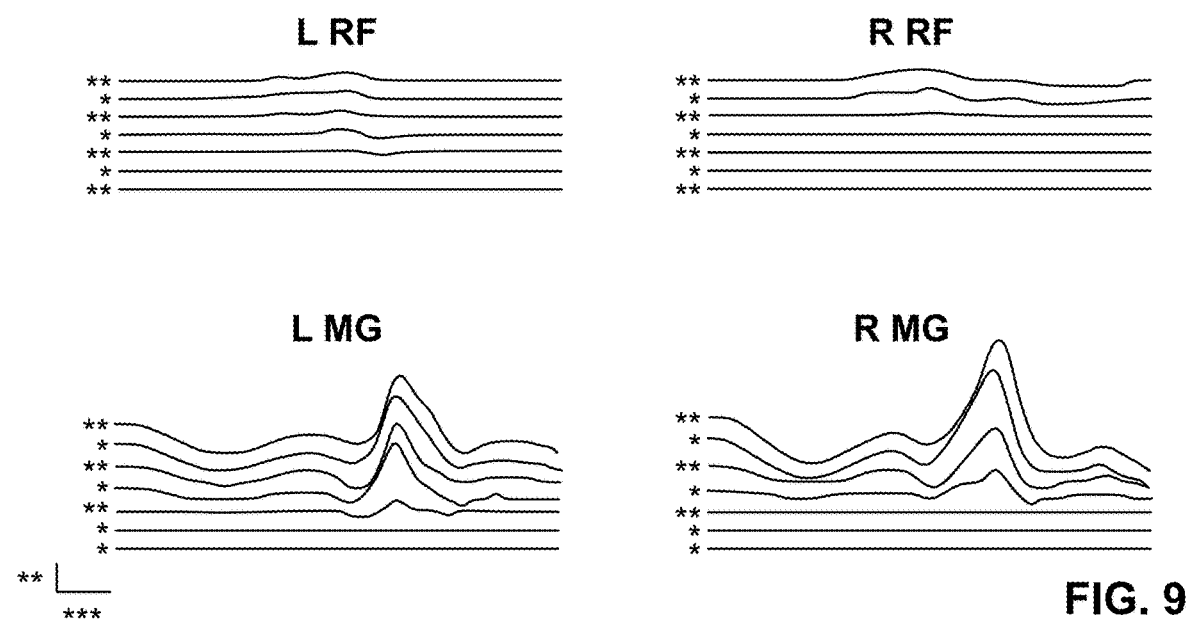
FIG. 9

ES 400 Rostral Configuration
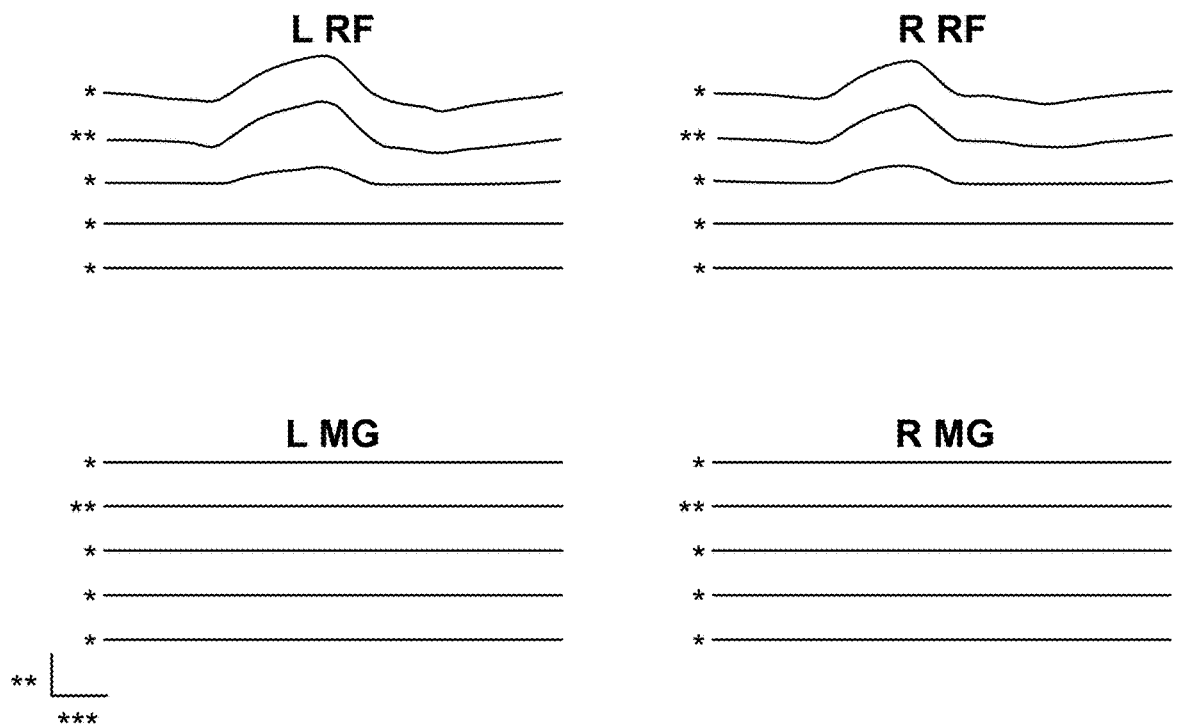
ES 400 Caudal Configuration
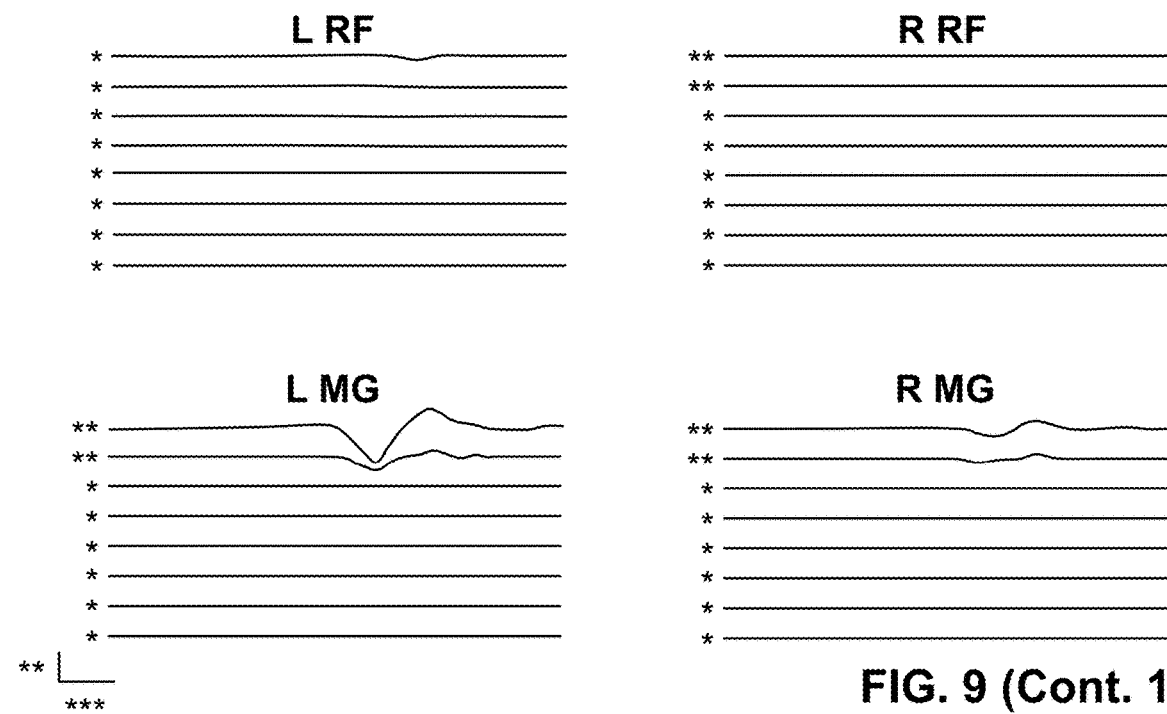
FIG. 9 (Cont. 1)

ES 400 Left Configuration
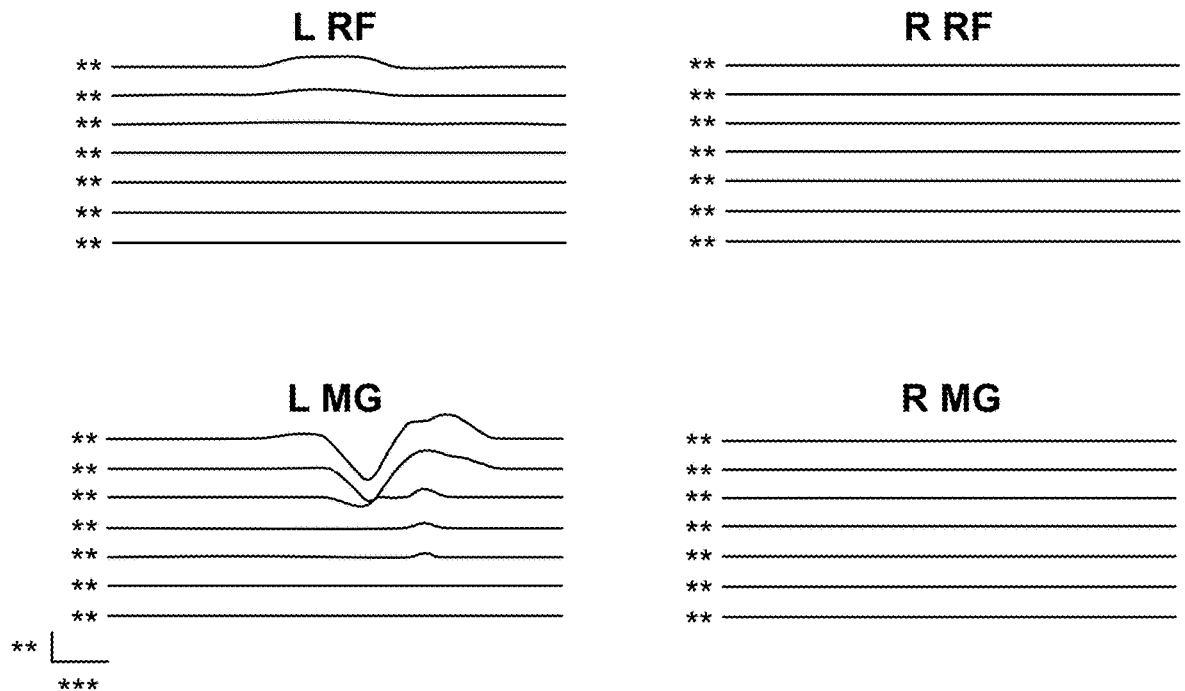
ES 400 Right Configuration
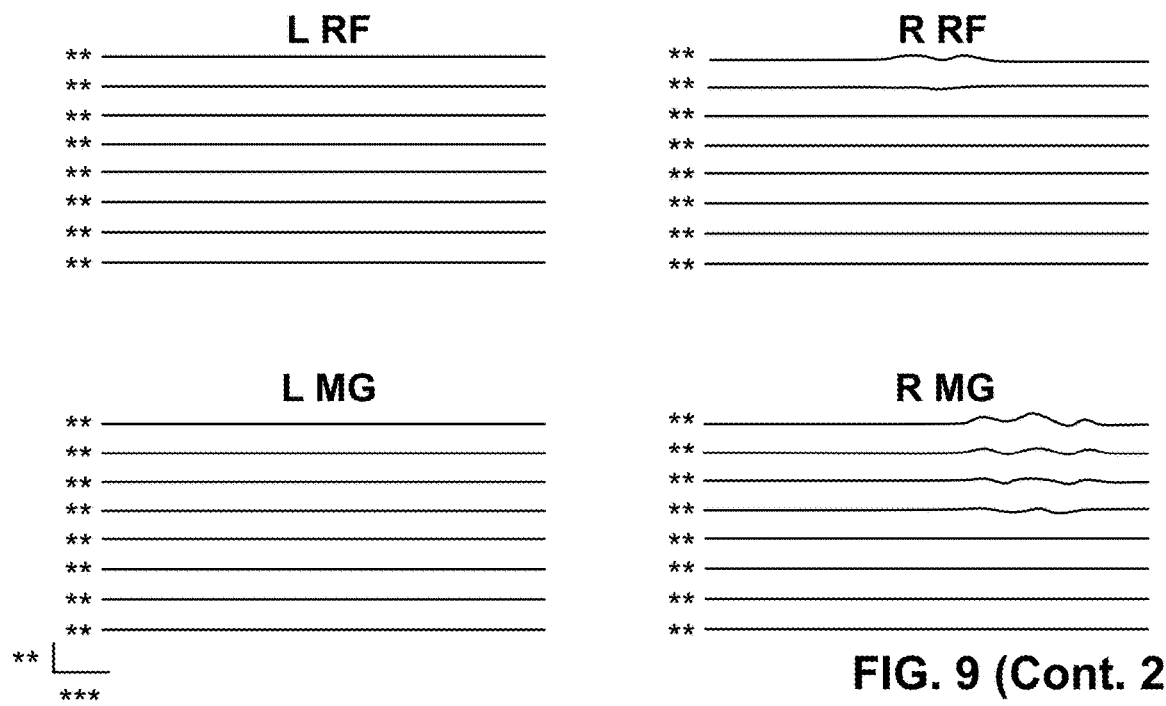
FIG. 9 (Cont. 2)

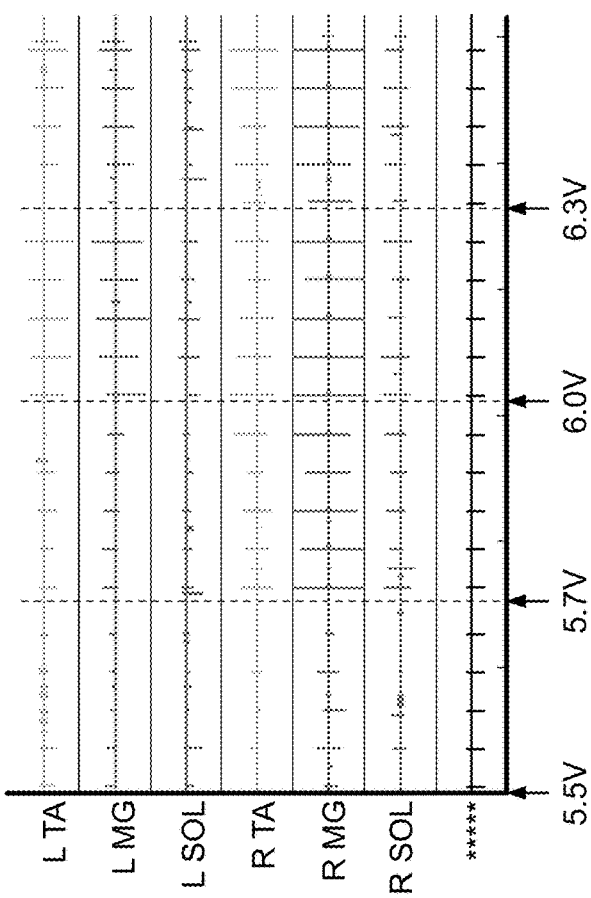
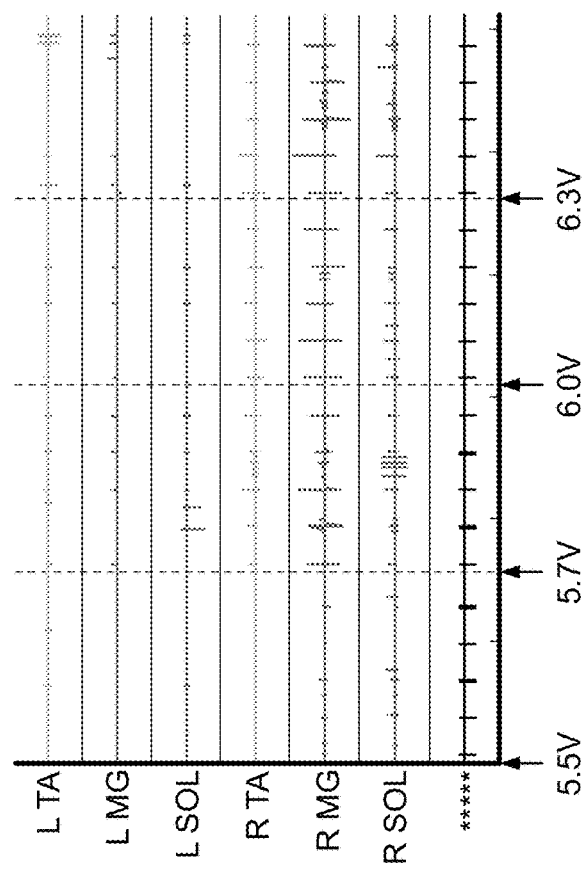
FIG. 10

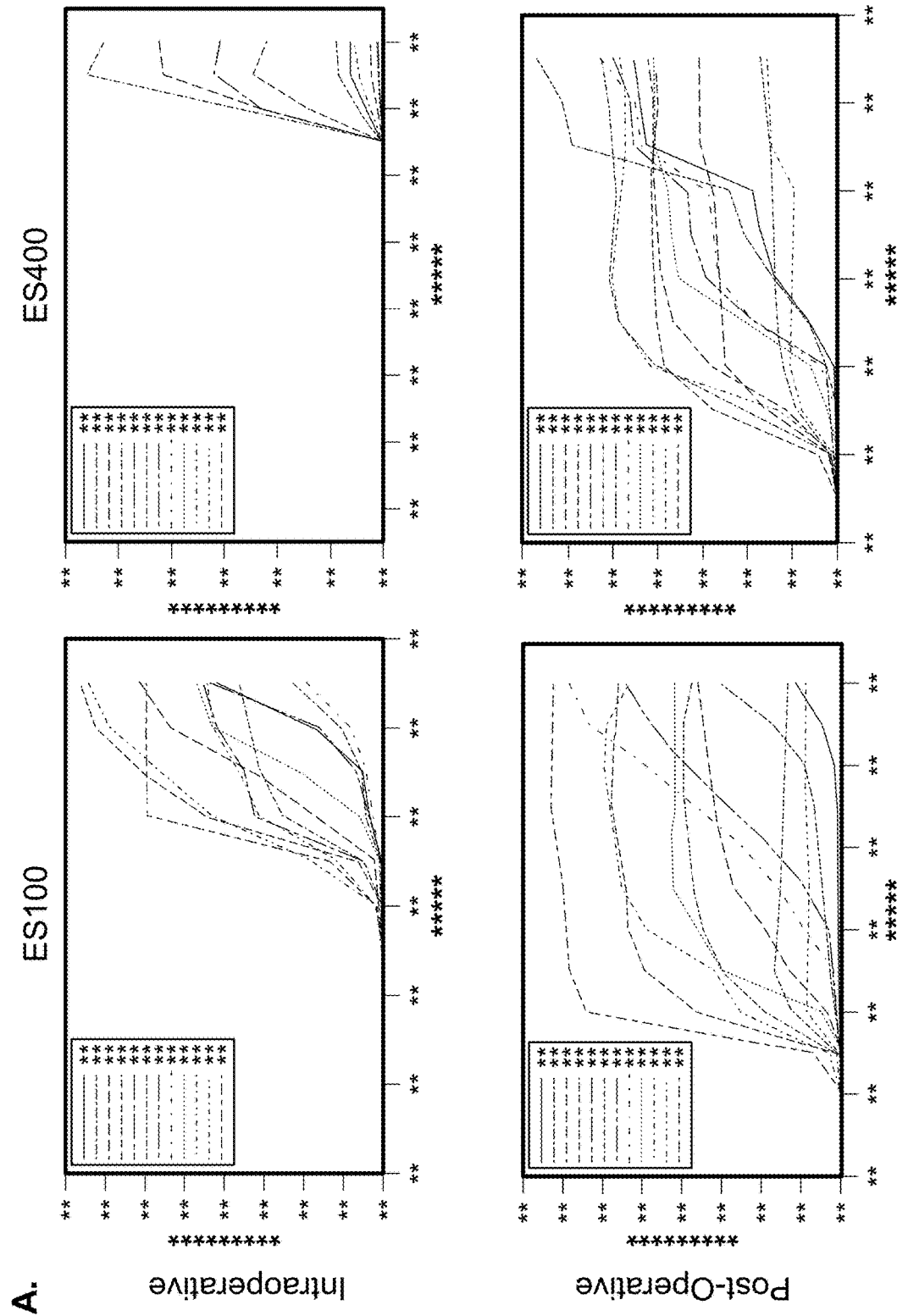
FIGS. 12A-B

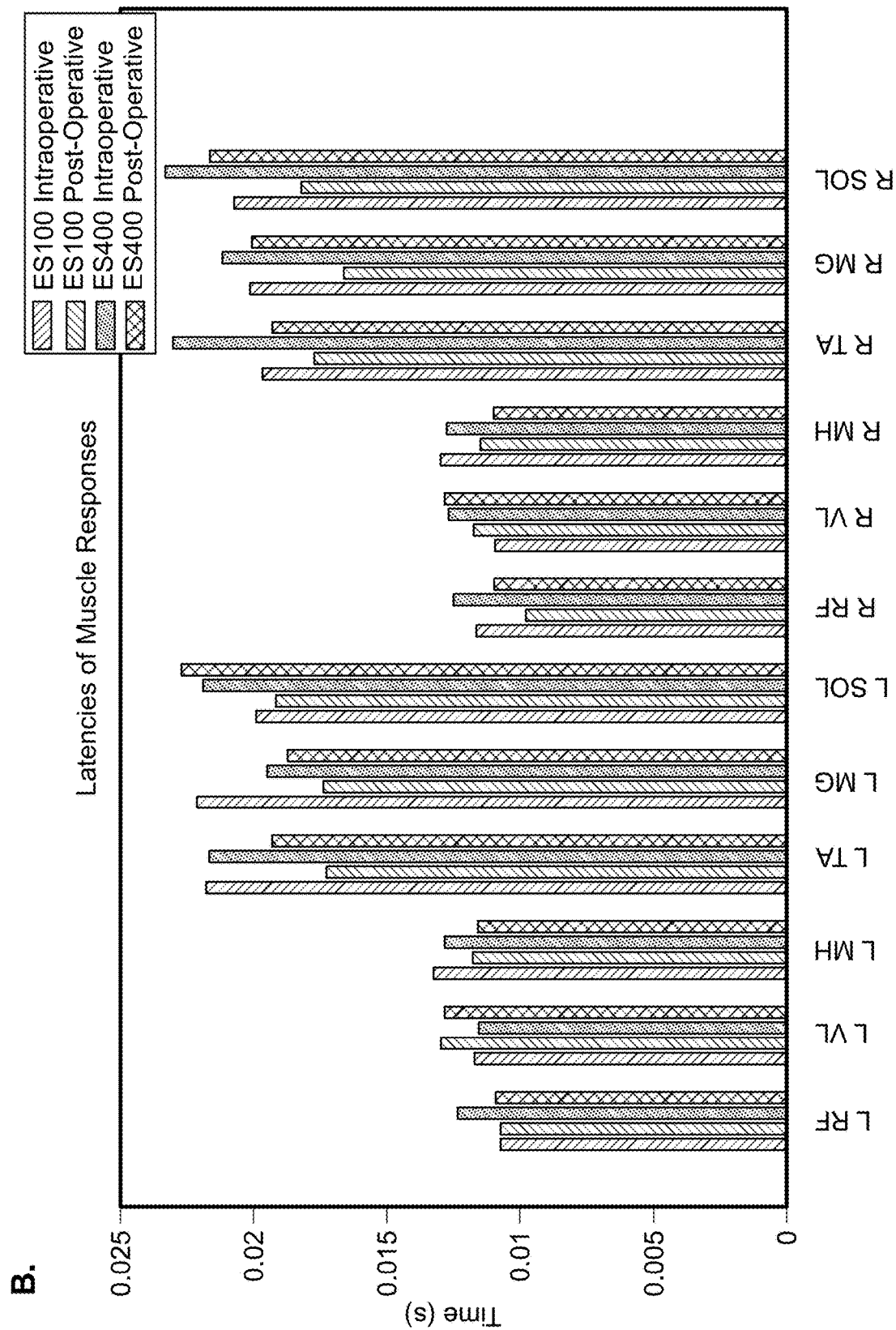
FIGS. 12A-B (Cont.)

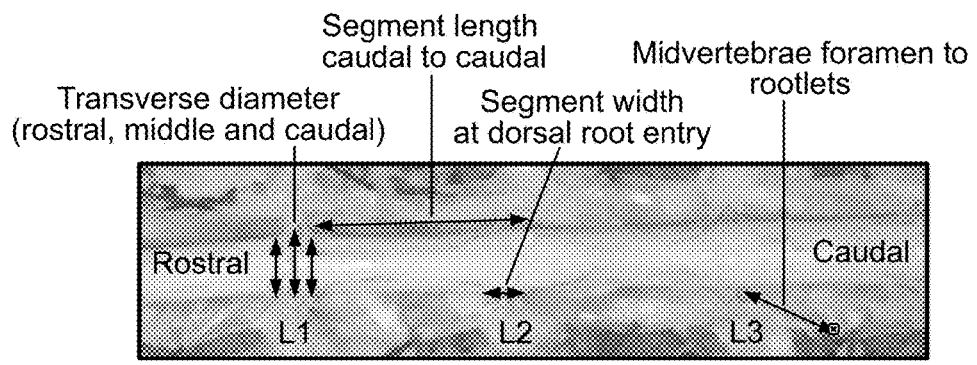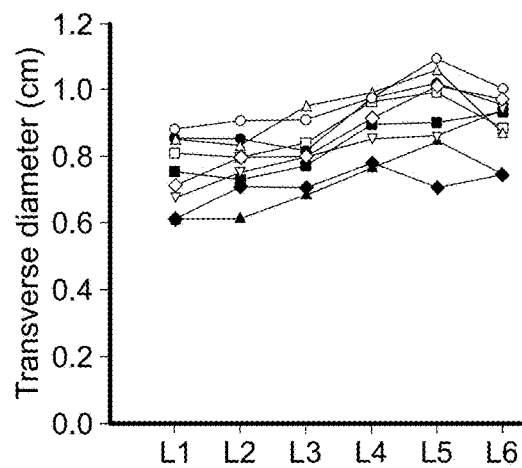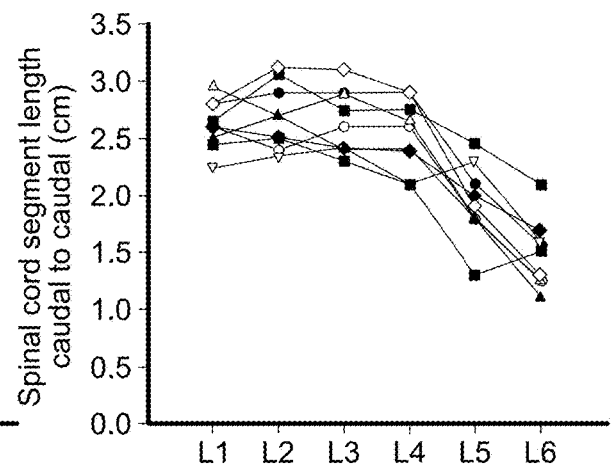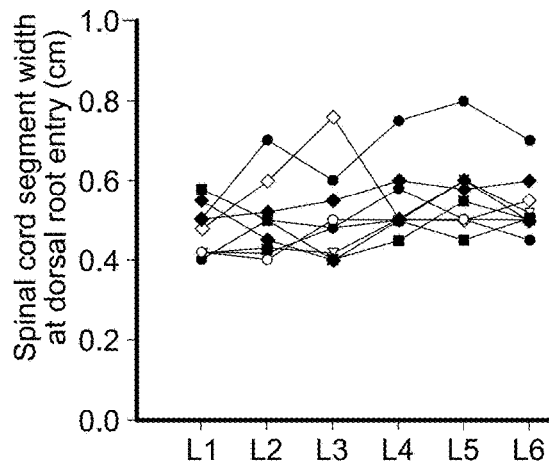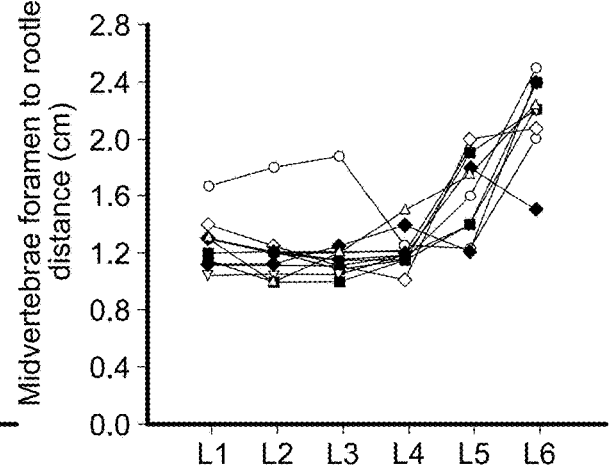
FIG. 13

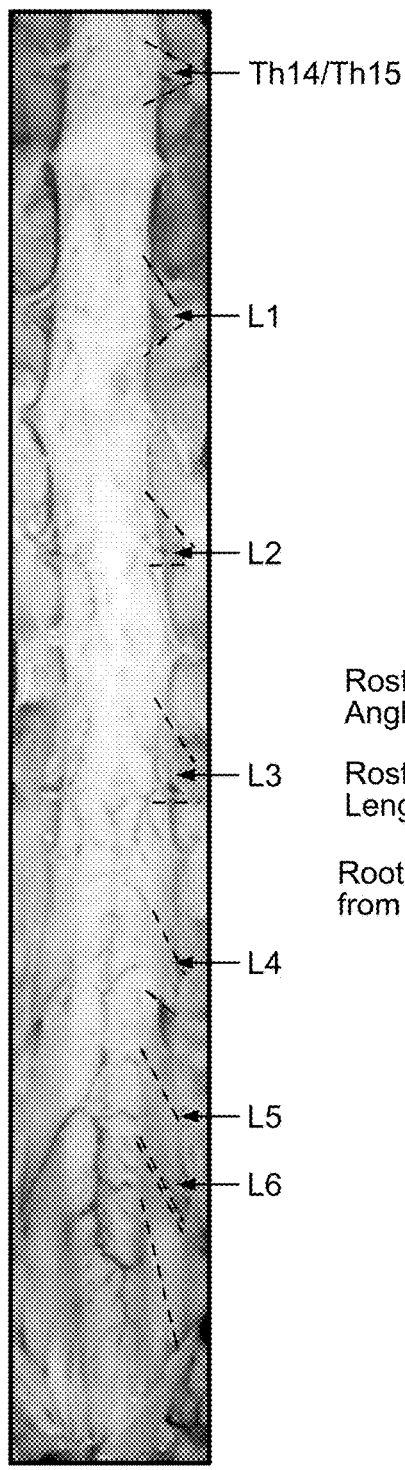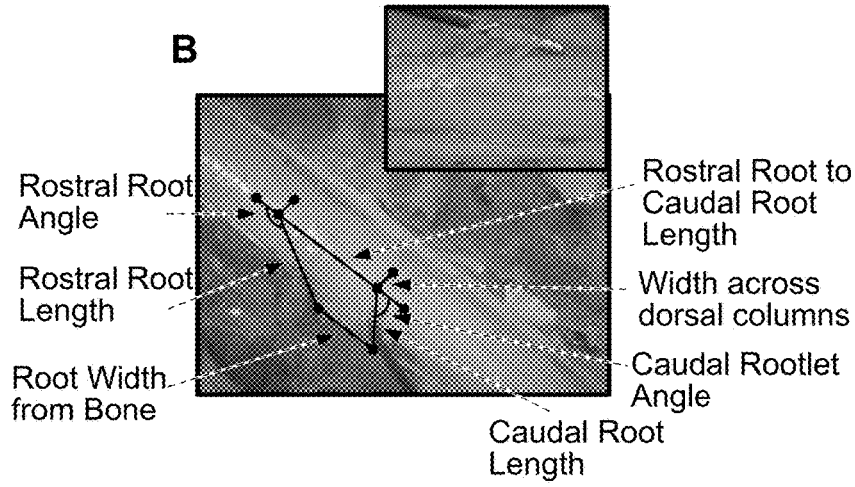
FIG. 14

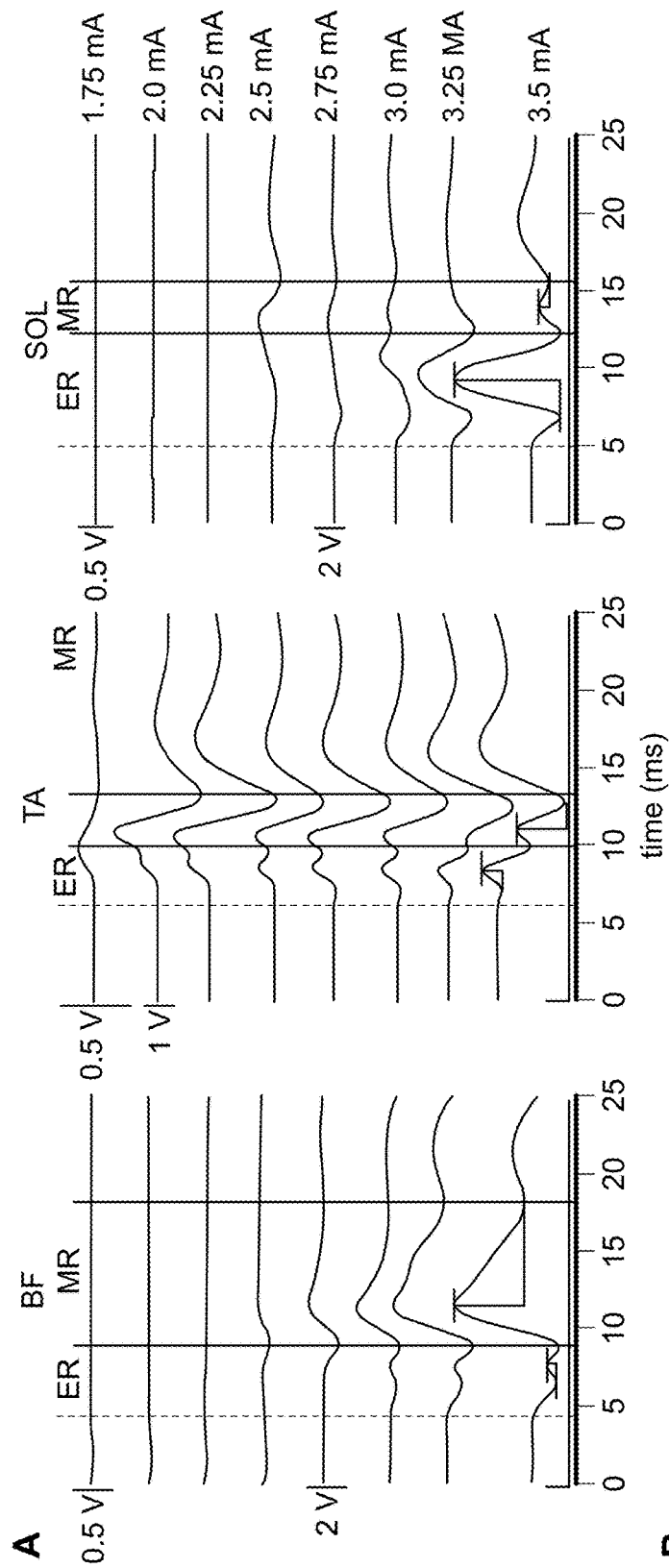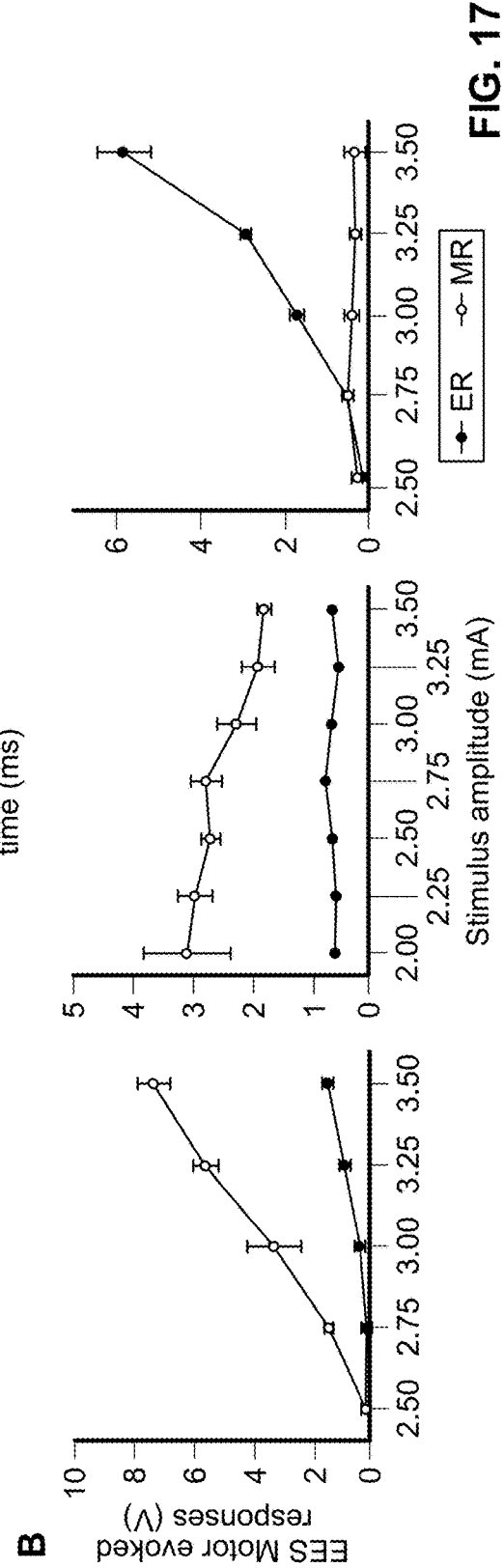
FIG. 17

EPIDURAL STIMULATION AND SPINAL STRUCTURE LOCATING TECHNIQUES

CROSS-REFERENCE TO RELATED APPLICATIONS

This application is a National Stage application under 35 U.S.C. § 371 of International Application No. PCT/US2020/044003, having an International Filing Date of Jul. 29, 2020, which claims the benefit of U.S. Provisional Application Ser. No. 62/880,050, filed Jul. 29, 2019. The disclosure of the prior application is considered part of the disclosure of this application, and is incorporated by reference in its entirety. The disclosures of U.S. Provisional Application Ser. No. 62/734,741, filed Sep. 21, 2018, and U.S. Provisional Application Ser. No. 62/620,953, filed Jan. 23, 2018, are also considered part of the disclosure of this application, and are incorporated by reference in their entireties.

BACKGROUND

Complete spinal cord injury (SCI) is thought to lead to permanent loss of voluntary control over function below the injury level. Despite a loss of brain input, evidence from both animal models and humans with motor complete SCI has shown that epidural electrical stimulation (EES) of lumbosacral spinal circuitry can generate muscle activity comprised of tonic and rhythmic firing patterns. See Ichiyama R M, Gerasimenko Y P, Zhong H, Roy R R, Edgerton V R. Hindlimb stepping movements in complete spinal rats induced by epidural spinal cord stimulation. Neuroscience Letters 2005; 383(3):339-44; Gerasimenko Y P, Ichiyama R M, Lavrov I A, et al. Epidural Spinal Cord Stimulation Plus Quipazine Administration Enable Stepping in Complete Spinal Adult Rats. Journal of Neurophysiology 2007; 98(5): 2525-36; Lavrov I, Dy C J, Fong A J, et al. Epidural Stimulation Induced Modulation of Spinal Locomotor Networks in Adult Spinal Rats. Journal of Neuroscience 2008; 28(23):6022-9; Dimitrijevic M R, Gerasimenko Y, Pinter M M. Evidence for a spinal central pattern generator in humans. Ann NY Acad Sci 1998; 860:360-76; Minassian K, Jilge B, Rattay F, et al. Stepping-like movements in humans with complete spinal cord injury induced by epidural stimulation of the lumbar cord: electromyographic study of compound muscle action potentials. Spinal Cord 2004; 42(7): 401-16; Danner S M, Hofstoetter U S, Freundl B, et al. Human spinal locomotor control is based on flexibly organized burst generators. Brain 2015; 138(3):577-88.

SUMMARY

This specification generally describes systems, methods, devices, and other techniques for activating motor function in an individual having complete or partial paralysis of one or more limbs due to spinal cord injury (SCI). In particular, the techniques described herein involve the use of epidural electrical stimulation (EES) systems to activate motor function in limbs that cannot otherwise be activated from the brain or central nervous system as a result of a complete or partial SCI.

A conventional EES system includes a pulse generator and an electrode array, and can be implanted in a patient to facilitate desired motor functionality. The pulse generator sends electrical signals to the electrode array, which in turn includes one or more electrodes that have been placed on the dura at a location corresponding to a particular portion of the spine. The electrical signals activate the electrodes, thereby causing the electrodes to generate local electrical pulses according to the signals. The electrical pulses can stimulate muscle tissue in the paralyzed limb so as to activate motor function. Typically, however, EES systems have only been equipped to provide a single stimulation program at a time, such as to activate motor function in a single limb or to activate the same motor function in multiple limbs.

This specification describes improved EES systems, methods, devices, and other techniques. For example, and EES system can include two or more implantable pulse (waveform) generators (IPGs). In some implementations, the system includes a multi-electrode array and at least two independent IPGs configured to independently deliver multiple stimulation programs simultaneously. The stimulation parameter settings can be independently adjusted for each IPG. The system can select particular electrodes in the array and localize stimulation timing and position over spinal cord regions that are associated with motor functions such as standing and stepping. In some implementations, multiple IPGs are contained in a single implanted device, and the stimulation provided by each IPG is coordinated to achieve desired stimulation of particular locations of the spinal cord. The spinal cord reacts to the stimulations to drive leg or other limb movement. The EES system may also include a wireless communication component for short-range wireless communication. The system may also include a rechargeable power supply module.

Furthermore, this specification describes an approach to optimizing efficacy of an EES system in the context of physical rehabilitation in order to achieve desired outcomes for a patient. In some implementations, an EES system is configured to execute two or more independent stimulation programs in series or concurrently to stimulate different portions of the spinal cord affecting motion of the patient. In some examples, an interleaved stimulation method involves running two independent stimulation programs applied to different portions of the spinal cord to alternate stimulation of left and right leg motor pools and enable walking by a completely paralyzed patient. In some examples, current controlled stimulation can be applied to different portions of the spinal cord.

This specification further describes techniques for the use of vertebral anatomical markers to target electrode placement over specific dorsal roots. Electrode location can then be verified using intra-operative and/or post-operative electrophysiology (e.g., electromyography) of electrical evoked spinal motor potentials recorded for select leg muscles. In some implementations, an EES system provides selective orientation or steering of an electric field with respect to dorsal root location and root trajectories or orientations for precise targeting of dorsal spinal cord structures without undesirably activating adjacent structures. In some examples, the electrode array and device described in this specification are also applicable to subdural placement.

Some implementations of the subject matter described herein include a method. The method can include steps of: providing a first set of electrodes of an epidural electrical stimulation system at a first set of locations on the dura mater of a spine of a mammal, the first set of locations on the dura mater corresponding to a first muscle group of the mammal; providing a second set of electrodes of the epidural electrical stimulation system at a second set of locations on the dura mater of the spine of the mammal, the second set of locations on the dura mater corresponding to a second muscle group of the mammal; and stimulating the first and second sets of locations on the dura mater by electrically energizing the first and second sets of electrodes, respectively, thereby activating the first and second muscle groups in a coordinated manner.

These and other implementations can optionally include one or more of the following features.

The first set of electrodes and the second set of electrodes are part of an implanted epidural electrode array.

Providing the first set of electrodes can include placing the first set of electrodes at the first set of locations on the dura mater of the spine of the mammal and verifying that the first set of electrodes are operable, when energized at the first set of locations, to activate the first muscle group by capturing a first electromyogram (EMG) using EMG electrodes located at the first muscle group. Providing the second set of electrodes can include placing the second set of electrodes at the second set of locations on the dura mater of the spine of the mammal and verifying that the second set of electrodes are operable, when energized at the second set of locations, to activate the second muscle group by capturing a second EMG using EMG electrodes located at the second muscle group.

Stimulating the first and second sets of locations on the dura mater can include energizing the first and second sets of electrodes with electrical waveforms generated by at least one implanted pulse generating devices.

Stimulating the first set of locations on the dura mater can include energizing the first set of electrodes with a first electrical waveform generated by a first implanted pulse generating device, and stimulating the second set of locations on the dura mater comprises energizing the second set of electrodes with a second electrical waveform generated by a second implanted pulse generating device.

The first and second implanted pulse generating devices can energize the first and second sets of electrodes concurrently using different waveform parameters.

The first and second implanted pulse generating devices can energize the first and second sets of electrodes in an alternating fashion.

The first or second electrical waveforms can have at least one of the following waveform parameters: (i) a pulse width in the range 10 microseconds to 1 second, (ii) a frequency in the range 0.5 to 10 kHz, (iii) a pulse amplitude in the range 0 to 20 Volts, or (iv) an electrical current level in the range 0.1 to 20 milliamps.

The first muscle group can be a muscle group in a first leg of the mammal. The second muscle group can be a muscle group in a second leg of the mammal. The first and second sets of electrodes can be energized to stimulate the first and sets of locations on the dura mater, respectively, thereby activating the first and second sets of muscles to cause a walking motion of the first and second legs of the mammal.

Some implementations of the subject matter described herein include an epidural electrical stimulation system. The system can include a plurality of electrodes, a plurality of waveform generators, and a controller. The plurality of electrodes can be configured to be disposed at various locations on nerve tissue of a mammal, such as on the dura mater of a spine of the mammal. Each waveform generator can be coupled to a different subset of the plurality of electrodes and can be configured to energize its corresponding subset of the plurality of electrodes, thereby stimulating local nerve tissue proximate to the corresponding subset of the plurality of electrodes and activating a muscle group associated with the local nerve tissue. The controller can be configured to coordinate the plurality of waveform generators so as to activate a plurality of muscle groups of the mammal to perform a specified action.

These and other implementations can optionally include one or more of the following features.

The specified action can be walking.

The mammal can be a human.

The system can include between two and ten independent waveform generators.

The plurality of muscle groups can be located in one or more limbs of the mammal. The mammal can have a complete or partial spinal cord injury that has resulted in paralysis of the one or more limbs.

Some aspects of the subject matter disclosed herein include methods for locating spinal cord structures. The methods can include determining values for one or more features of at least one vertebra of a spine of a subject. Locations of one or more structures of the spinal cord of the subject are determined based on the values for the one or more features of the at least one vertebra. The one or more structures of the spinal cord of the subject can then be accessed using their estimated locations.

These and other aspects can optionally include one or more of the following.

The locations of the one or more structures of the spinal cord can be estimated without physically accessing the spinal cord, or without using an image of the spinal cord.

The one or more structures of the spinal cord can include dorsal root entry zones. Estimating the locations of the one or more structures can include estimating the locations of at least one of dorsal root entry zones along the spinal cord, dorsal rootlet projections, ventral rootlet projections, gap between adjacent rootlet projections, or mid-line of the spinal cord.

Accessing the one or more structures of the spinal cord can include locating one or more electrodes on the spinal cord at or proximate to the dorsal root entry zones.

Accessing the one or more structures of the spinal cord can include drilling one or more holes into one or more vertebrae of the subject.

The subject can be a mammal, such as a human or a swine.

Estimating the locations of the one or more structures of the spinal cord of the subject can include (1) estimating values for one or more features of the spinal cord based on the one or more features of the at least one vertebra and (2) estimating the locations of the one or more structures of the spinal cord based on the estimated values for the one or more features of the spinal cord. The one or more features of the at least one vertebra can include at least one of an intervertebral length, a midvertebrae foramen length, a vertebral bone length, or an intervertebral spinous process length. The one or more features of the spinal cord can include at least one of a length of a spinal cord segment, a transverse diameter of a spinal cord segment, or a width of a spinal cord segment at a dorsal root entry. The one or more features of the at least one vertebra can include an intervertebral spinous process length for the L2 vertebra, and the one or more features of the spinal cord can include a length of a spinal cord segment corresponding to the L2 vertebra.

The one or more features of the at least one vertebra can include an intervertebral spinous process length for the L2 verterbra of the subject.

Determining the values for the one or more features of the at least one vertebra of the spine of the subject can include acquiring one or more images of the spine that depict a plurality of vertebral bones of the subject. Values for the one or more features of the at least one vertebra are measured from the one or more images of the spine.

The at least one vertebra can be located in the lumbar region of the subject's spine.

Accessing the one or more structures of the spinal cord of the subject using their estimated locations can include placing electrodes on the spinal cord at or near the one or more structures. The methods can further include stimulating the spinal cord using the placed electrodes.

Some aspects of the subject matter disclosed herein include paddle-type electrode arrays for epidural stimulation. The electrode array can include an elongated substrate having a central longitudinal axis, a plurality of central electrodes linearly arranged on the substrate along the central longitudinal axis, a first group of inner electrodes arranged on the substrate along a first inner longitudinal axis, the first inner longitudinal axis parallel to the central longitudinal axis, and a second group of inner electrodes arranged on the substrate along a second inner longitudinal axis, the second inner longitudinal axis parallel to the central longitudinal axis. In some embodiments, one or more of the longitudinal axes and their corresponding electrodes are optional. For example, a paddle-type electrode array may include inner and outer longitudinal sets of electrodes but no central longitudinal set.

These and other aspects can optionally include one or more of the following.

In certain implementations, the second group of inner electrodes may be symmetrical to the first group of inner electrodes with respect to the central longitudinal axis.

In certain implementations, the electrode array may further include a first group of outer electrodes arranged on the substrate along a first outer longitudinal axis, the first outer longitudinal axis parallel to the first inner longitudinal axis, the first inner longitudinal axis positioned between the central longitudinal axis and the first outer longitudinal axis. The electrode array may further include a second group of outer electrodes arranged on the substrate along a second outer longitudinal axis, the second outer longitudinal axis parallel to the second inner longitudinal axis, the second inner longitudinal axis positioned between the central longitudinal axis and the second outer longitudinal axis.

In certain implementations, the second group of outer electrodes may be symmetrical to the first group of outer electrodes with respect to the central longitudinal axis.

In certain implementations, the first group of inner electrodes may be arranged linearly or undulatingly along the first inner longitudinal axis. In certain implementations, the second group of inner electrodes may be arranged linearly or undulatingly along the second inner longitudinal axis.

In certain implementations, the first group of outer electrodes may arranged linearly or undulatingly along the first outer longitudinal axis. The second group of outer electrodes may be arranged linearly or undulatingly along the second outer longitudinal axis.

In certain implementations, the substrate has a plurality of sections longitudinally arranged along the central longitudinal axis, the first and second groups of inner electrodes being arranged on the plurality of sections. In each of the sections, the inner electrodes in the first and second groups may be spaced equally along the first and second inner longitudinal axes.

In certain implementations, the substrate has a plurality of sections longitudinally arranged along the central longitudinal axis, the first and second groups of inner electrodes being arranged on the plurality of sections. In each of the sections, at least one set of adjacent electrodes in the first group of inner electrodes may be spaced at a different distance from at least another set of adjacent electrodes in the first group of inner electrodes. In each of the sections, at least one set of adjacent electrodes in the second group of inner electrodes may be spaced at a different distance from at least another set of adjacent electrodes in the second group of inner electrodes.

In certain implementations, the substrate has a plurality of sections longitudinally arranged along the central longitudinal axis, the first and second groups of outer electrodes being arranged on the plurality of sections. In each of the sections, the outer electrodes in the first and second groups may be spaced equally along the first and second outer longitudinal axes.

In certain implementations, the substrate has a plurality of sections longitudinally arranged along the central longitudinal axis, the first and second groups of outer electrodes being arranged on the plurality of sections. In each of the sections, at least one set of adjacent electrodes in the first group of outer electrodes may be spaced at a different distance from at least another set of adjacent electrodes in the first group of outer electrodes. In each of the sections, at least one set of adjacent electrodes in the second group of outer electrodes may be spaced at a different distance from at least another set of adjacent electrodes in the second group of outer electrodes.

In certain implementations, the plurality of central electrodes includes 4 central electrodes spreading out along a length of the substrate.

In certain implementations, each of the first and second groups of inner electrodes includes 18 inner electrodes.

In certain implementations, each of the first and second groups of outer electrodes includes 12 outer electrodes.

In certain implementations, the plurality of central electrodes are operated to position the substrate against a lumbar spine.

In certain implementations, the substrate includes a plurality of sections corresponding to a plurality of spinal segments (e.g., cervical, thoracic, lumbar).

In certain implementations, the plurality of lumbar segments includes L4, L5, and L6.

In certain implementations, the electrodes are arranged at a constant distance along a length of the array to provide a homogeneous contact density.

In certain implementations, the electrodes are arranged at variable distances along a length of the array to provide a variable contact density.

Some aspects of the subject matter disclosed herein include an electrode lead for epidural stimulation. The electrode lead includes a flexible lead wire body and an array of electrode contacts. The array can include a plurality of rows of electrode contacts and can be disposed along a distal portion of the lead wire body.

These and other aspects can optionally include one or more of the following features.

In certain implementations, each of the plurality of rows includes multiple semi-cylindrical stimulating contacts disposed around an axial center of the lead wire body.

In certain implementations, the plurality of rows are arranged at an identical distance to provide a homogeneous contact density.

In certain implementations, the plurality of rows are arranged at variable distances to provide a variable contact density.

In certain implementations, the lead wire body is flexed to mimic an angle at which rootlets enter a spinal cord.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other reference mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 4A-J depict the progression of EES-enabled walking performance on a treadmill. EES settings used during week 4 (Panel A) and week 43 (Panel F) for walking on a treadmill are shown (anodes=black, cathodes=red). Photographs from week 4 (Panel B) and week 43 (Panel G) depict treadmill parameters, BWS, and trainer assistance required to walk during EES. RF and MH activity synchronized to vGRF indicates bilateral step cycle phases at week 4 (Panel C) and week 43 (Panel H). RMS envelopes calculated from 10 consecutive steps of each leg show individual and averaged traces with respect to stance and swing phases at week 4 (Panel D) and week 43 (Panel I). RF and MH muscle activity during stance, early swing phase (first 50%), and late swing phase (last 50%) phase were normalized to the average activity during 10 consecutive steps of each leg at week 4 (Panel E) and week 43 (Panel J). Average activity was assigned an arbitrary unit of 1. Muscle activities above or below 1 were defined as activated and inhibited, respectively. (Key: EES=epidural electrical stimulation; Hz=Hertz; V=Volts; BWS=body weight support; EMG=electromyography; s=second; RMS=root mean square; µV; =microvolt; vGRF=vertical ground reaction force; N=Newton; RF=rectus femoris; MH=medial hamstring).

FIGS. 6A-J depict progression of EES-enabled walking performance over ground. EES settings used during week 4 (Panel A) and week 43 (Panel F) for walking over ground are shown (anodes=black, cathodes=red). Photographs from week 4 (Panel B) and week 43 (Panel G) depict required trainer assistance to walk during EES. RF and MH activity synchronized to vGRF indicates bilateral step cycle phases at week 4 (Panel C) and week 43 (Panel H). RMS envelopes calculated from 10 consecutive steps of each leg show individual and averaged traces with respect to stance and swing phases at week 4 (Panel D) and week 43 (Panel I). RF and MH muscle activity during stance, early swing phase (first 50%), and late swing (last 50%) phase were normalized to the average activity during 10 consecutive steps of each leg at week 4 (Panel E) and week 43 (Panel J). Average activity was assigned an arbitrary unit of 1. Muscle activities above and below 1 were defined as activated and inhibited, respectively. (Key: EES=epidural electrical stimulation; Hz=Hertz; V=Volts; BWS=body weight support; EMG=electromyography; s=second; RMS=root mean square; µV; =microvolt; vGRF=vertical ground reaction force; N=Newton; RF=rectus femoris; MH=medial hamstring).

FIG. 8A is a diagram depicting location of EES array within the spine and implanted pulse generator. FIG. 8B shows an x-ray of each subject (ES100, ES400) before and after EES implantation surgery. Both subjects were implanted T12-L1 interspace and slid rostrally to the T11 vertebral region. ES100 was sitting during imaging, while ES400 was supine. ES100 has spinal fusion hardware at T11 and rostral to this region. This was used to guide implantation of the EES electrode below this region. ES400 does not have any device at this region, and therefore implantation was primarily accomplished through imaging techniques.

FIG. 9 depicts plots of intraoperative electrophysiology data ensuring optimal placement of electrode. Rostral configuration stimulates proximal muscles (R RF, L RF), and caudal configuration stimulates distal muscles (R MG, L MG). While left and right configurations stimulate ipsilateral muscles. Here, each line represents the average response to stimulation over at least five stimulations. Voltage increases from bottom to top. Stimulation is given at the start of each trace.

FIG. 10 depicts plots of electrode location determined by intraoperative electrophysiological recording. Intraoperative data from ES400 using a caudal, symmetric (−10/+8) configuration. Electromyography (EMG) data from three bilateral distal muscles are shown (TA=Tibialis Anterior, MG=Medial Gastrocnemius, SOL=Soleus) as well as a stimulation artifact recorded from the left paraspinal muscles. Panel A displays EMG data as voltage is incrementally increased from 5.5 to 6.3 volts. Following this data recording, the electrode array was shifted left in order to achieve recruitment of both legs during stimulation. Panel B displays the same muscles and voltages following movement of the electrode.

FIGS. 12A-B depicts plots showing similar electrophysiological responses across subjects and testing. Latency and amplitude of EMG (Electromyography) data was calculated to assess differences and similarities between testing conditions and subjects. Amplitude was calculated as the difference between the maximum and minimum of response. Latency is defined as the time between stimulation and beginning of response. Data was examined across six bilateral muscles: RF (rectus Femoris), VL (vastus lateralis), MH (medial hamstring), TA (tibialis anterior), MG (medial gastrocnemius), SOL (soleus).

FIG. 13 depicts images of a swine's lumbar spinal cord anatomy. (A) Depiction of the spinal cord anatomical landmarks identified in this study: transverse diameter, segment length caudal to caudal, segment width at dorsal root entry and midvertebrae foramen to rootlets. Data per specimen (n=9) across lumbar segments is shown for (B) Spinal cord transverse diameter, (C) Segment length (caudal to caudal root distance), (D) Segment width at dorsal root entry zone and (E) Midvertebrae foramen to rootlets.

FIG. 17 depicts epidural electrical stimulation (EES)-evoked motor responses. (A) ER and MR representative responses recorded in BF (biceps femoris), TA (tibalis anterior) and SOL (soleus) muscles at different stimulation intensities (1.75 mA-3.5 mA) in subject 2 using the multi-contact rod array. Each trace is the average of ten motor evoked responses. Dotted lines indicate the beginning of the first deflection corresponding to ER. Continuous lines indicate MR. Examples of the peak-to-peak amplitude measurements for both ER and MR are shown at the bottommost traces (3.5 mA). (B) Recruitment curves showing ER (black dots) and MR (white dots) responses as shown in (A).

DETAILED DESCRIPTION

This specification describes techniques for activating muscle groups in a mammal using an implantable epidural electrical stimulation (EES) system. Severe, traumatic injury of the spine results in fracture and dislocation of spine structures that in turn leads to acute and chronic disruption of spinal cord tissues. Among the techniques discussed are a surgical approach to implant the EES system, intraoperative and post-operative electrophysiological monitoring of electrically evoked motor potentials to guide placement in the operating room, verifying stimulator/electrode positioning post-operatively, and coordinating stimulation of multiple sets of electrodes using one or more waveform generating devices concurrently or in series to affect motion of paralyzed limbs, such as for walking. Also described are techniques for reliably locating spinal cord structures (e.g., dorsal root entry zones, ventral root entry zones, dorsal rootlet projections, ventral rootlet projections, and/or zones in between adjacent rootlet projections). A set of anatomy specific paddle and lead arrays to target the spinal cord structures. In addition to EES for spinal cord injury, the disclosed techniques are further relevent for EES application including but not limited to chronic pain, Parkinson's disease, ALS, or other neurological diseases.

Figure 1:
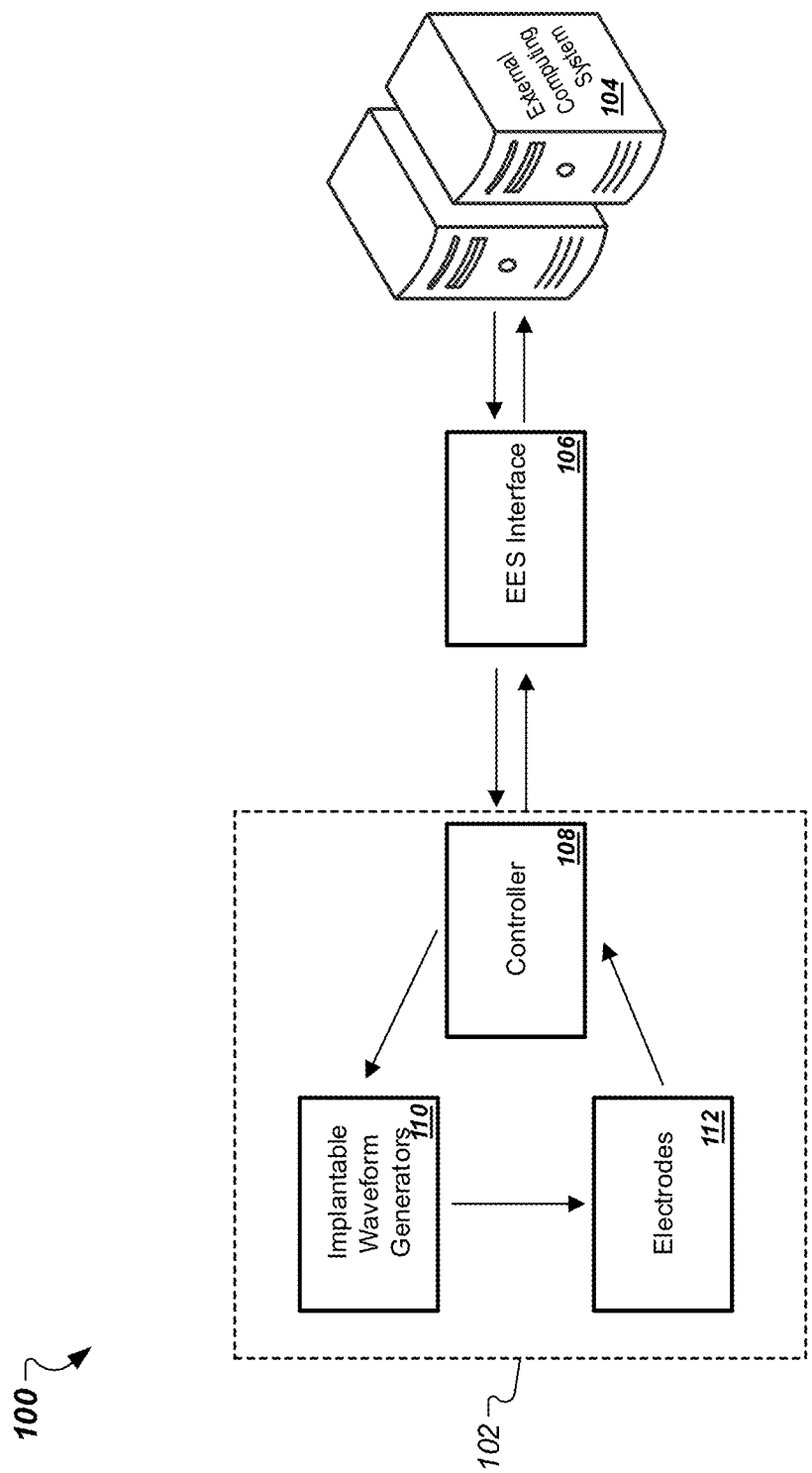
FIG. 1 is a block diagram of an example epidural electrical stimulation system according to certain implementations of the subject matter disclosed herein.

FIG. 1 depicts a conceptual diagram of an example epidural stimulation system 100. The system includes an implantable portion 102 and, optionally, an interface 106 and an external computing system 104. In general, the implantable portion 102 is configured to be implanted in a mammal (e.g., a human) to stimulate nerve tissue that drives activation of particular muscle groups in the mammal. The implantable portion 102 includes a controller 106, one or more waveform generators 110, and a set of electrodes 112. The implantable portion 102 is surgically implanted in the mammal, such as according to the techniques described in the Example Implementations below. Different sets of electrodes 112, for example, may be placed on the dura mater of the spine of the mammal at locations that correspond to muscle groups that are desired to be activated. The electrodes 112 can be energized by waveform generators 110. One type of waveform generator is an implantable pulse generator (IPG), which is configured to generate a pulsed waveform. In some implementations, the system 100 includes multiple implanted waveform generators 110, which can be co-located on an integrated device or physical separate from each other. A first waveform generator 110 may be installed, for instance, proximate to a first subset of electrodes that it drives, while a second waveform generator 110 may be installed, for instance, proximate to a second subset of electrodes that it is configured to drive. The controller 106 is a data processing apparatus that selects parameters for the waveforms generated by each of the waveform generators 110. In some implementations, the controller 106 is separate from the waveform generators 110, but alternately the controller 106 may be integrated in the same devices as the waveform generators 110. Because each waveform generator 110 can independently drive a different subset of electrodes to affect motion of different muscle groups, the controller 106 may also coordinate operations of multiple waveform generators 110 and thereby coordinate the movements of multiple muscle groups to achieve a specified action (e.g., walking). The system 100 can be an open-loop or closed-loop feedback system. In some implementations, the controller 106 communicates with an external computing system 104 via EES interface 106. For example, a user may define a stimulation program on external computing system 104, which can then be uploaded to the implantable system 102 (e.g., controller 106) using the EES interface 106.

In some implementations, the system 100 is configured to facilitate walking in an individual with a complete or partial SCI and paralyzed legs. Electrodes 112 are positioned on the dura of the spine to target select spinal motor pools associated with enabling desire movements of each leg. Separate waveform generators 110 drive different subsets of electrodes 112 in an interleaved program to independently facilitate stimulation of select spinal cord structures that affect alternating limb activation. For example, a first waveform can be applied to a first subset of electrodes 112 to cause movement of the left leg and a second waveform can be applied to a second subset of electrodes 112 to cause movement of the right leg in alternating fashion to recreate a walking motion. In general, the waveforms applied to the electrodes can be pulsed with a pulse with duration of about 10 microseconds to 1 second (e.g., 0.1-0.5 milliseconds), a frequency of about 0.5 to 10,000 Hz (e.g., 0.5-200 Hertz), a pulse amplitude in the range of about 0-20 V (e.g., 0-10 V, in 0.05 V increments), a current in the range of about 0.1 to 20 milliamps and the waveform can either be voltage gated or current gated. In some examples, the frequency can be adjusted in increments of about 0.1 Hz to about 1 Hz, from about 0.5 Hz to about 2 Hz, from about 1 Hz to about 5 Hz, or from about 5 Hz to about 10 Hz. The waveforms applied to each subset of electrodes can be independently optimized, so as to optimize timing and position of probes and waveform parameters for multiple stimulation programs (e.g., waveform) executed concurrently.

Electrodes 112 can be implanted in the patient blow the spinal cord injury (SCI). To verify optimal placement of the electrodes 112, intraoperative and/or post-operative electrophysiology can be perform to ensure that the locations on the dura where the electrodes are placed can activate spinal motor pools associated with motor activity of desired muscle groups (e.g., muscle groups in the arms or legs). For example, additional electrodes can be located on the surface of the patient over the targeted muscle groups or within the targeted muscle groups to detect electrical activity from muscles below the level of injury, such as trunk and leg muscles involved in posture and weight bearing during standing.

In some implementations, specific spinal landmarks are used to optimize electrode placement with respect to dorsal root ganglia. In this way, the geometry/anatomy of vertebrae can be leveraged as a proxy for spinal cord geometry. In some implementations, imaging techniques such as computed tomography (CT) scans, ultrasound, or magnetic resonance imaging (MRI) can be employed to target dorsal rootlets for optimal electrode placement. In particular, these imaging techniques can be used to visualize spine and spinal cord landmarks that can be used to correlation the location of target dorsal roots.

In some implementations, the patient's rehabilitation strategy may rely on a combination of epidural electrical stimulation and multimodal physical rehabilitation (MMR). Rather than a "top down" approach designed to sequentially train muscle groups in stages, MMR uses simultaneous rehab approach to train all targeted muscle groups for specific tasks, such as sit to stand, standing, weight shifting, treadmill walking, or over-ground walking. The MMR team can assist with movement, for example, so that the EES system can stimulate nerve tissue to activate motor function for a normal walking rhythm. Waveform parameters and stimulation programs can be optimized based on patient and therapist feedback gathered from MMR. For instance, movement threshold can inform adjustments in waveform parameters used to stimulate the nerve tissue, such as the frequency, pulse width, and/or amplitude of the waveform. Therapists may be provided with automated tools to measure kinematics and to guide changes in waveform parameters.

Figure 2:
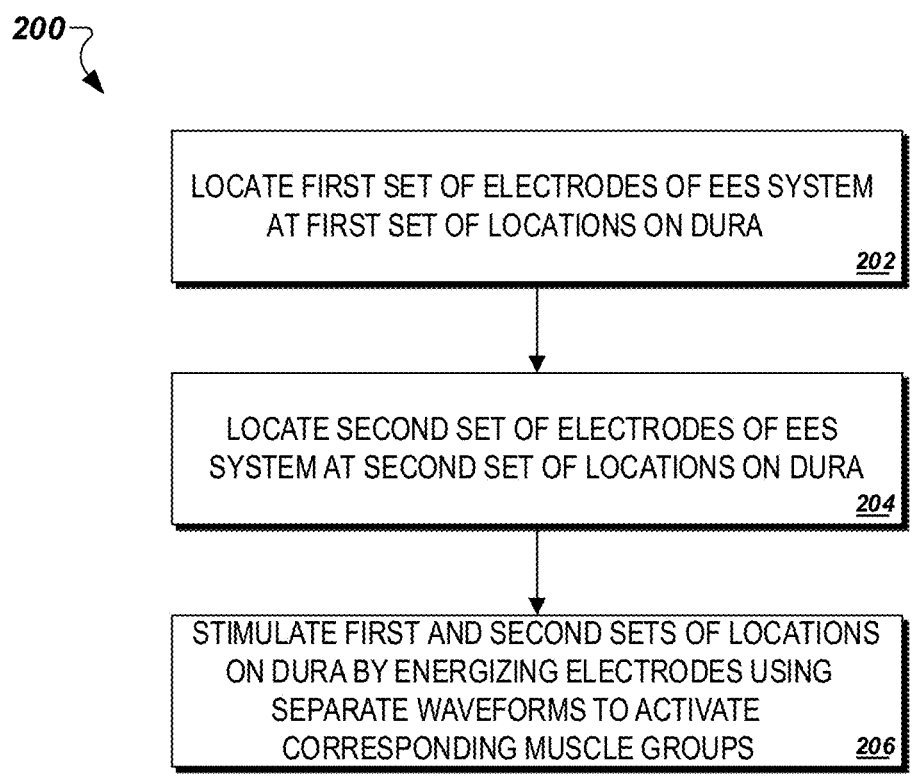
FIG. 2 is a flowchart of an example process for animating muscle groups of a mammal by coordinated stimulation of nerve tissue of the mammal, e.g., using two or more implantable pulse generators.

FIG. 2 is a flowchart of an example process 200 for locating electrodes in an implantable epidural electrical stimulation (EES) system, and for using the system activate muscle groups causing motion in a patient. At stage 202, a first set of electrodes are placed on the dura mater of the spine at targeted locations corresponding to a muscle group that is to be activated. At stage 204, a second set of electrodes are placed on the dura at additional targeted locations corresponding to an additional muscle group that is to be activated. At stage 206, the system stimulates the locations of the dura where the electrodes are placed by energizing the electrodes with in implantable pulse or waveform generator. Different waveforms can be applied concurrently or in series to the different sets of electrodes. As a result of the stimulation, the muscle groups corresponding to the targeted spinal locations can be activated to cause motion, such as alternating leg motion for walking.

As further described with respect to example implementation #3 below, improved (e.g., higher) peak-to-peak motor responses to epidural electrical stimulation can be achieved by targeted stimulation of the dorsal root entry zones at one or more locations along the spine. As demonstrated below, experimental results in swine indicate that the magnitude of the motor response to EES is highly dependent on proximity of the stimulating electrodes to the dorsal rootlet projections. Even small (e.g., a few millimeters) offset between position of the electrode on the spinal cord and the dorsal rootlet projections can significantly impact the therapeutic impact of EES. To determine the locations of the dorsal rootlet projections, or other targeted structures of the spinal cord, correlations between features (anatomical landmarks) of a subject's vertebrae and features of the spinal cord can be utilized to estimate the locations of the targeted structures. These correlations can be used to facilitate precise implantation of electrodes or other devices at specific locations of the spinal cord (e.g., dorsal root entry zones for targeted spinal segments, dorsal rootlet projections for targeted spinal segments, ventral rootlet projections for targeted spinal segments), even without the need to perform a laminectomy or without a clear image of the spinal cord.

Figure 20:
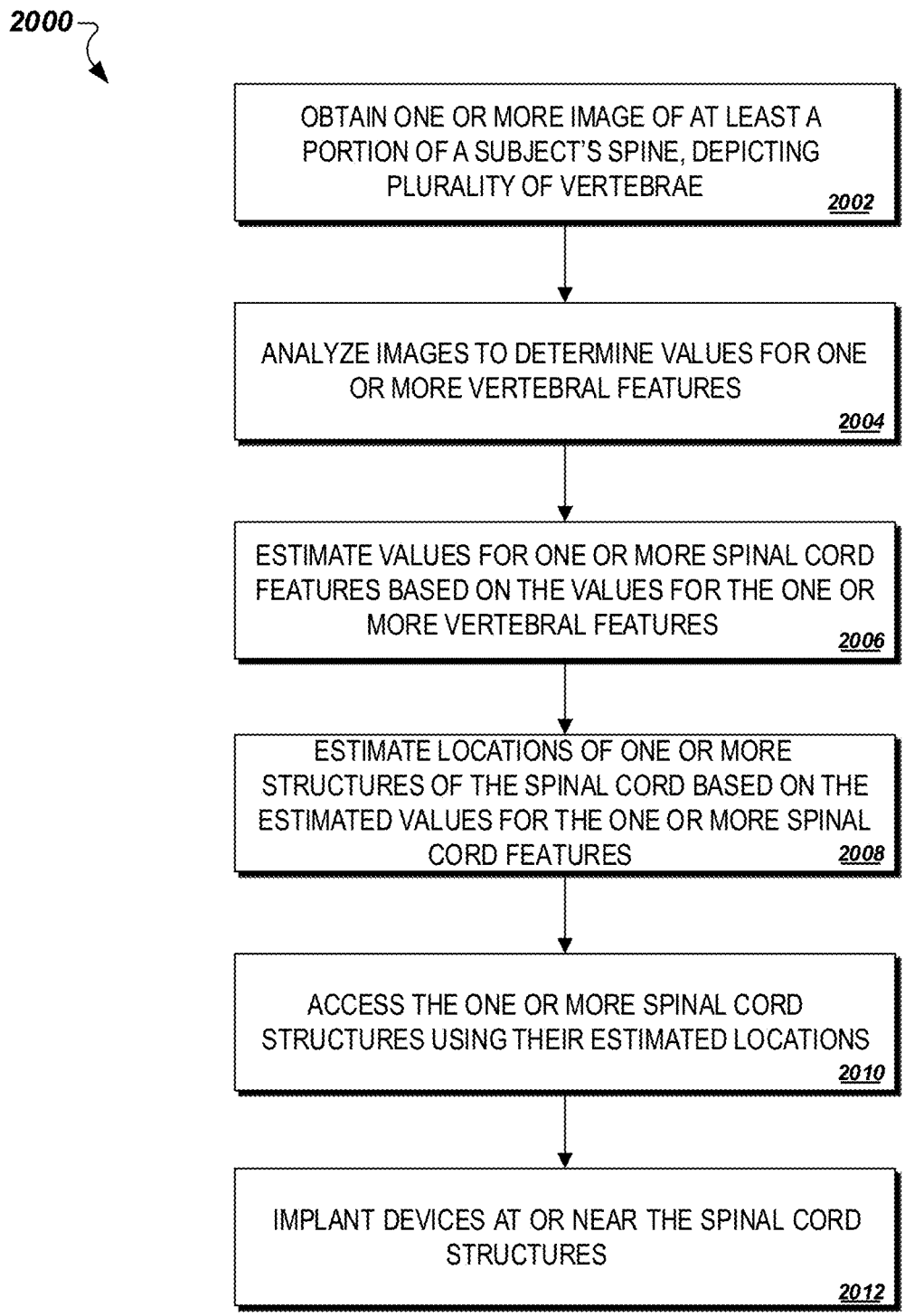
FIG. 20 is a flowchart of an example process for using anatomical features of a subject's vertebrae to determine estimated locations of spinal cord structures, and using the estimated locations to access the structures and implant electrodes or other devices along the spinal cord structures.

An example process 2000 for accessing targeted structures or locations of the spinal cord based on anatomical features of the verterbrae is represented in the flowchart of FIG. 20. The process 2000 can be performed, for example, by a surgeon or other medical team during a pre-operation phase for a procedure to implant electrodes in the spine for EES therapy. More generally, the process 200 may be adapted to access targeted structures or locations of the spinal cord for any purpose, such as for placement of epidural electrodes for treatment of chronic pain, for spinal cord injury, for subdural or intrathecal drug delivery, for spinal cord stereotaxic surgeries, including selective rhizotomy, and more.

At stage 2002, the physician obtains one or more images of at least a portion of a subject's spine. The images can be obtained using any suitable technique, such as computed tomography (CT) imaging or magnetic resonance imaging (MRI). The subject may be a human or other mammal, such as swine, calf, sheep, or rodents. Typically, the images will show the relevant portion of the subject's spine in which access to particular spinal cord segments is desired, such as the lumbar region and/or the lower thoracic region.

At stage 2004, the images are analyzed to determine values for one or more vertebral features of the subject's spine. The vertebral features can serve as references from which values for one or more spinal cord features and estimated locations of particular structures along the spinal cord can be determined based on statistically defined correlations between the vertebral features, the spinal cord features, and/or the locations of the spinal cord structures (e.g., dorsal rootlet projections, ventral rootlet projections, dorsal root entry zones). In some aspects, the vertebral features are intervertebral or intersegmental features that have high statistical correlation with spinal cord features and/or locations of one or more spinal cord structures. The vertebral features can include intervertebral lengths for one or more pairs of vertebrae, midvertebrae foramen length for one or more vertebrae, vertebral bone length for one or more vertebrae, and/or intervertebral spinous process length for one or more vertebrae. In the study described below with respect to example implementation #3, the L2 intervertebral spinous process length was shown to have highest correlation with spinal segment length and can serve as an effective vertebral feature for determining estimated values for certain spinal cord features (e.g., spinal cord segment length).

Figure 16:
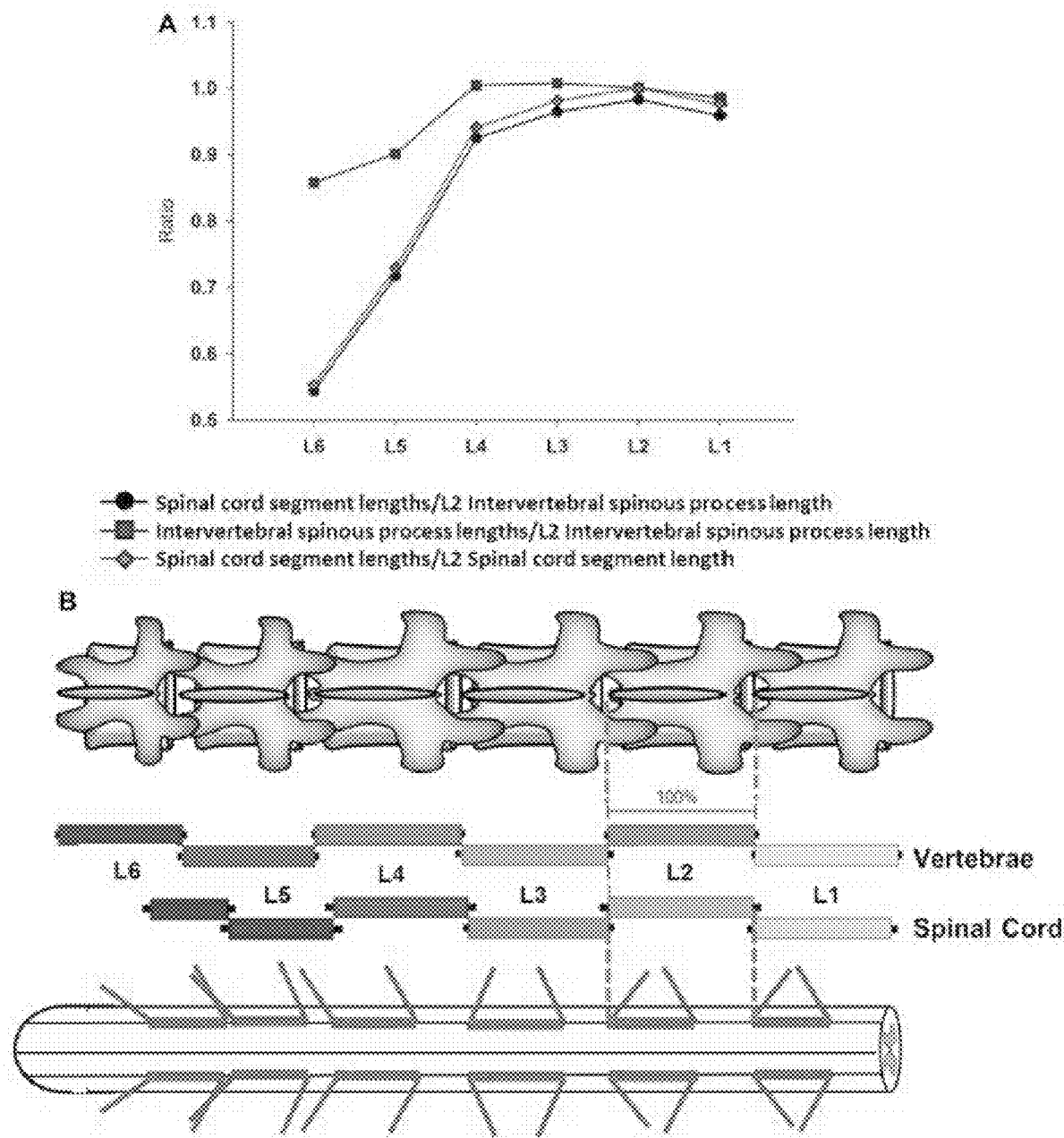
FIG. 16 depicts intersegmental relationship between the spine and spinal cord. (A) Ratios between the intervertebral spinous process length at L2 vertebra and the spinal cord segments lengths from L1 to L6 vertebras (black line and circles). The ratios between the intervertebral spinous process lengths across lumbar segments and the L2 intervertebral spinous process length (blue line and squares), as well as the ratios between the spinal cord segments lengths and L2 spinal cord segment length are also shown (red line and diamonds). (B) Schematic representation of intervertebral spinous process lengths (top diagram and blue palette rectangles) and spinal cord segment lengths (bottom diagram and red palette rectangles) showing the segmental correspondence between them. Mean lengths (±SD, black bars) are expressed as percentage of the L2 intervertebral spinous process length (100%). The thicker on the spinal cord diagram represent the segment sizes at dorsal root entries expressed as percentage respect to L2 intervertebral spinous process length. Dorsal root mean angles (rostral and caudal) are also shown (thinner projecting lines).

At stage 2006, values for one or more features of the spinal cord are estimated based on the values for the one or more vertebral features. The spinal cord features can include, for example, lengths of one or more spinal segments (e.g., lengths of segments corresponding to particular vertebrae). For example, a statistical model for a class of subjects may indicate that the length of the L4 segment of the spinal cord is 80-percent of the length of the L2 intervertebral spinous process length, and the physician may estimate the L4 length as such. Other features of the spinal cord that may be modeled and estimated from the determined vertebral features include, for each spinal segment, a transverse diameter of the cord, a length of the segment, a width of the segment at the dorsal root entry, and distance from midvertebrae foramen to spinal rootlets. FIG. 16, for example, depicts the intersegmental relationship between the spine and spinal cord for swine, based on the study described below in example implementation #3. An estimated spinal cord segment length can be determined from the L2 intervertebral spinous process length based on the high correlation between these features.

At stage 2008, locations of one or more structures along the spinal cord can be estimated based on the values for the one or more spinal cord features. For example, FIG. 16(*b*) shows a schematic representation of the spinal segment sizes at the dorsal root entries, along with rostral and caudal root mean angles for each segment. The dorsal rootlet projection corresponds to the root entry zone contained by the rostral and caudal angle. Based on a model such as that shown in FIG. 16(*b*) of the location and orientation of dorsal rootlet projections for each spinal segment, the absolute locations of the dorsal rootlet projections can be determined by computing the lengths of the spinal cord segments (e.g., based on a relationship to a vertebral feature such as the L2 intervertebral spinous process) and identifying the portion of each segment where the targeted structure (e.g., the dorsal rootlet projections, dorsal root entry zone) is located. In some aspects, a distance between the targeted structure and one or more landmark features of the vertebrae can be determined using the estimated lengths of the spinal cord structures and the modeled locations of the structures at each spinal segment.

At stage 2010, the targeted structures along the spinal cord can be accessed based on information about their estimated locations. In some aspects, accessing the spinal cord structures involves drilling through one or more vertebrae to reach the determined locations of the structures. In some aspects, at stage 2012, a device can be implanted at or near the targeted structures of the spinal cord. For example, stimulation electrodes can be implanted at the dorsal rootlet projections to maximize therapeutic effect of epidural electrical stimulation.

Referring now to FIGS. 21-32, example electrode arrays or leads 3000, 3100, 3200, 3300, 3400, 3500, and/or 3600 are illustrated. The arrays or leads 3000-3600 can be used in some implementations to carry out the epidural stimulation techniques described herein.

As described herein, the electrode arrays or leads 3000, 3100, 3200, 3300, 3400, 3500, and/or 3600 are configured so that, in use, respective sets of electrodes are disposed on the dura mater of the spine of the mammal at targeted locations. For example, a given electrode array can be configured for placement on portions of the dura mater that correspond to muscle groups that are desired to be activated, e.g., to alleviate chronic pain or enable motor function, respiratory muscle activation, and/or bladder control following spinal cord injury.

In some embodiments, the geometries of the epidural stimulation electrode arrays are based on the anatomy of one or more specific spinal cord segments, such as lumbar segments L4, L5, and/or L6. The electrode arrays are configured (e.g., based on the arrangement, size, and spacing of the electrodes) to provide targeted delivery of stimulation. Although the example electrode arrays described herein are configured to be applied to portions of the spinal cord corresponding to lumbar segments L4, L5, and L6 (e.g., and thus have geometries that correspond to these segments), it is understood that the electrode arrays can also be configured to be applied to one or more other spinal cord segments such as lumbar segments L1-L3, or thoracic segments.

The electrodes in the arrays or leads 3000, 3100, 3200, 3300, 3400, 3500, and/or 3600 can be arranged in groups or units, with each group configured to stimulate a different targeted rootlet projection entering the dorsal column. Each group or unit of electrodes may be independently activated and controlled, and each may be oriented in a direction corresponding to the direction of the targeted rootlet projection. In this way the electrodes can be placed over or in close proximity to the rootlet projections to enhance the stimulation efficiency of the electrodes (e.g., so that a target level of stimulation can be achieved with minimum or reduced excitation/signal power from the electrodes). For example, vectors of two or more electrodes that match a direction of a particular dorsal rootlet projection can be selectively activated as a unit to stimulate the root. The unit of electrodes, for instance, can include one electrode from an outer column of the array and one or more electrodes from one or more inner columns of electrodes. Therefore, the electrode arrays or leads 3000, 3100, 3200, 3300, 3400, 3500, and/or 3600 may consume less power for stimulation compared to other approaches. Additionally, the electrode arrays or leads 3000, 3100, 3200, 3300, 3400, 3500, and/or 3600 may provide a high stimulation contact density that permits more specific or targeted stimulation.

In some embodiments, the electrode arrays 3000, 3100, 3200, and 3300 can each include two or more differently sized electrodes capable of specifically stimulating diverging rootlets entering the spinal cord. For example, electrodes of a larger size are arranged at an outer side of the array and can act as a common anode for electrodes of a smaller size which are arranged at an inner side of the array and function as cathodes. This configuration can achieve higher specificity without increasing the number of contacts. The electrode arrays may operate to independently stimulate both sides of the spinal cord through separate anode and cathode, resulting in bilateral specificity. Alternatively, electrode arrays can each include single-sized electrodes. For example, the electrode arrays or leads 3400, 3500, and 3600 may or may not have electrodes having a same size.

In some embodiments, the electrode arrays 3000, 3100, 3200, 3300, 3400, and/or 3500 have the orientation of electrodes configured to reduce the chance of stimulation spillover to the other side of the spinal cord and thus eliminate phase contradicting the stimulation effect.

Figure 21:
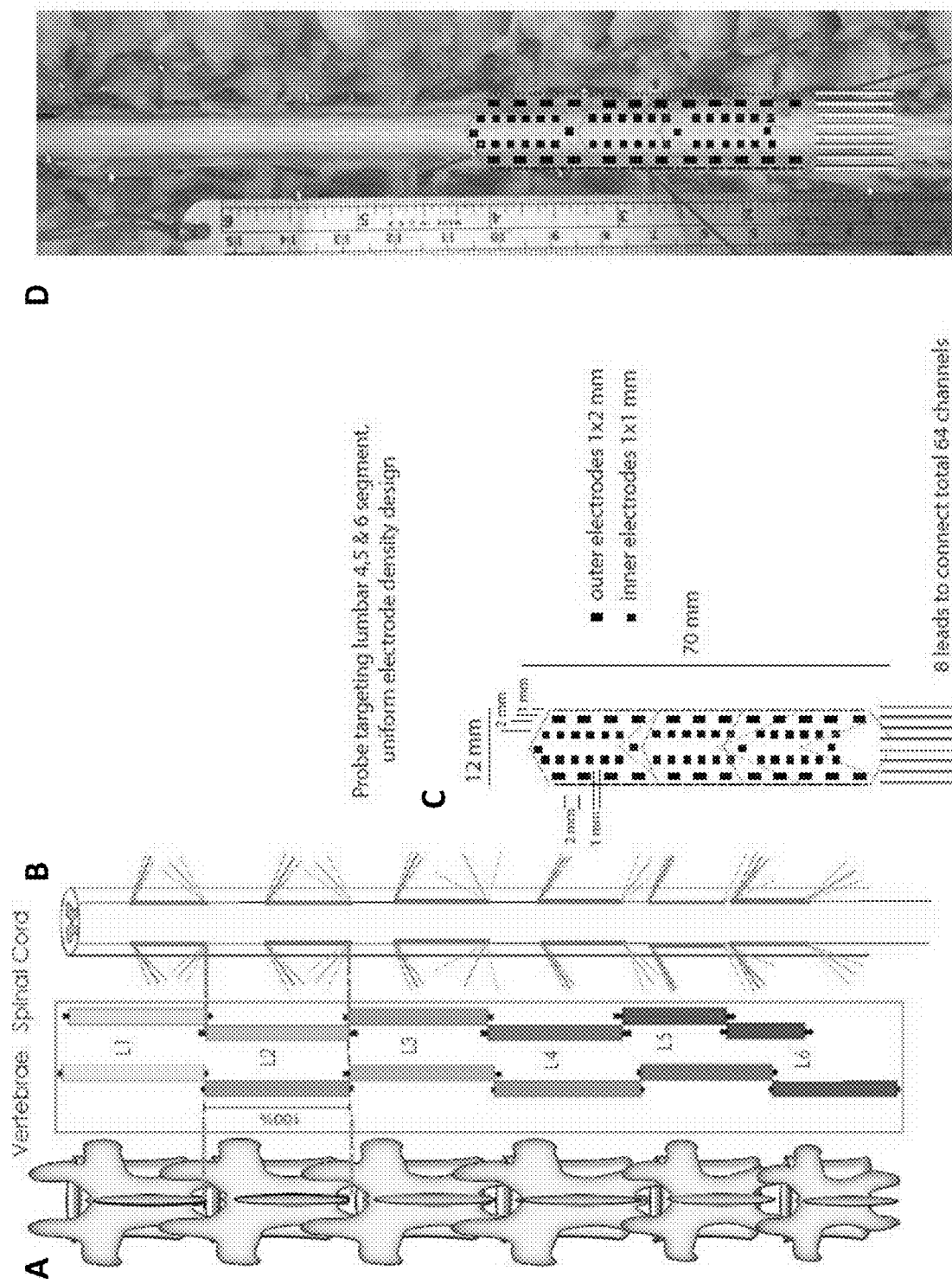
FIGS. 21-32 depict example electrode arrays or leads that can be employed to carry out epidural stimulation techniques.
Figure 22:
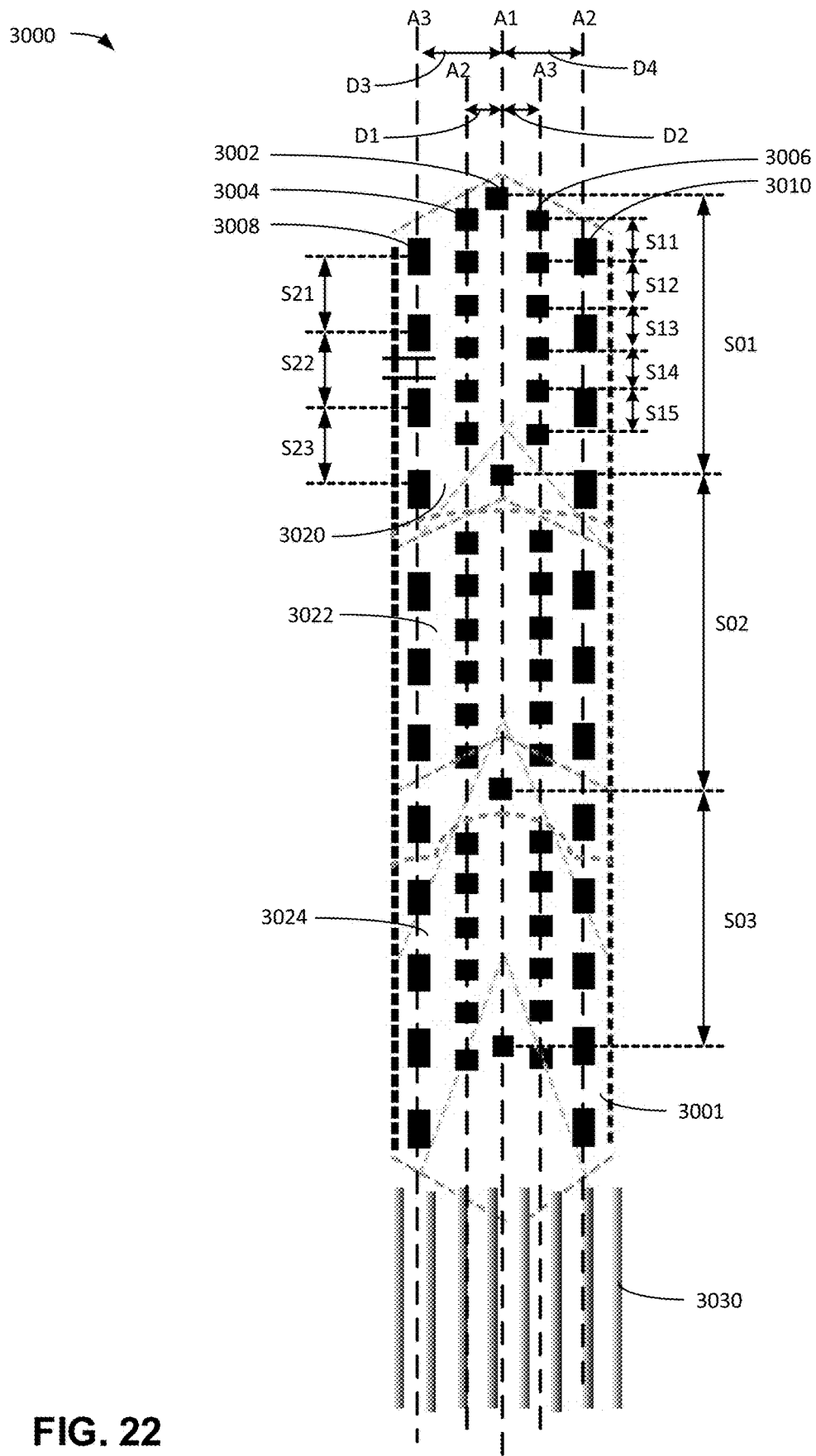

Referring to FIGS. 21 and 22, a first example epidural stimulation electrode array 3000 is depicted. Dorsal roots are illustrated in FIG. 21B, which shows various rostral and caudal root angles across different lumbar segments L1-L6. The spatial orientation of dorsal roots are correlated to the anatomical landmarks of the lumbar spine. For example, the geometry/anatomy of vertebrae (FIG. 21A) can be leveraged as a proxy for spinal cord geometry. Example angles of the dorsal rootlet projections are illustrated in FIG. 27B, which correspond to the lumbar segments shown in FIG. 27A. FIGS. 27C and 27E illustrate an example electrode array 3000 (described below with reference to FIGS. 21 and 22) and an example electrode array 3020 (described below with reference to FIGS. 25 and 26) which are configured to cover the ranges of angles of the roots as shown in FIG. 27B. FIGS. 27D and 27E schematically illustrate the engagement of the arrays 3000 and 3020 with desired lumbar segments.

The angles of each dorsal root or dorsal rootlet projection can vary across a population. The variation is represented in the figures by means and deviations. In FIG. 21B, the solid line of each dorsal root represents a mean projection orientation of the dorsal root, and the two dashed lines on either side of the solid line indicates statistical deviations of the root from the mean orientation based on measurement results of dorsal root angles. An example epidural stimulation electrode array 3000 is shown in FIG. 21C, which is further described with reference to FIG. 22. FIG. 21D schematically illustrates that the electrode array 3000 is arranged to target lumbar segments (e.g., L4, L5, and L6).

As shown in FIG. 22, the electrode array 3000 is configured to provide a uniform electrode density. The electrode array 3000 includes a substrate 3002, a plurality of central electrodes 3004, a first group of inner electrodes 3006, and a second group of inner electrodes 3008. The electrode array 3000 can further include a first group of outer electrodes 3010 and a second group of outer electrodes 3012.

The substrate 3002 can be of an elongated profile adapted to cover one or more spinal segments, such as a plurality of of lumbar segments. The substrate is configured to be placed based on a bone anatomy to provide targeted delivery of stimulation. In some embodiments, the length of the substrate can range from about 40 mm to about 90 mm, while the width of the substrate can range from about 4 mm to about 20 mm. In other embodiments, the substrate can be about 70 mm in length and 12 mm in width. Other configurations are also possible.

The plurality of central electrodes 3002 is arranged on the substrate along a central longitudinal axis A1. The plurality of central electrodes 3002 can in some embodiments be configured to facilitate positioning of the substrate along a target lumbar spinal segment. In some embodiments, the central electrodes 3002 are arranged linearly along the central longitudinal axis A1. In other embodiments, the central electrodes 3002 are arranged undulatingly along the central longitudinal axis A1.

The number of the central electrodes 3002 can vary as appropriate. In some embodiments, four central electrodes 3002 are provided as illustrated in FIG. 22. Other numbers of central electrodes 3002, such as one, two, three, five, six, and more, can be provided in other embodiments. In yet other embodiments, no central electrode can be provided on the substrate.

The central electrodes 3002 can be of various shapes, such as square, rectangle, circle, oval, etc. The central electrodes 3002 can be of the same shape. Alternatively, the central electrodes 3002 can vary in shape. The central electrodes 3002 can be of various dimensions. In one embodiment, the central electrodes 3002 are sized to be about 1×1 mm2. Other dimensions are also possible in other embodiments. The central electrodes 3002 can be of the same size. Alternatively, the central electrodes 3002 can vary in size.

The central electrodes 3002 can be spaced equally along the central longitudinal axis A1. In other embodiments, a spacing S0 (e.g., S01, S02, or S03) between adjacent central electrodes 3002 can vary along the central longitudinal axis A1.

Figure 25:
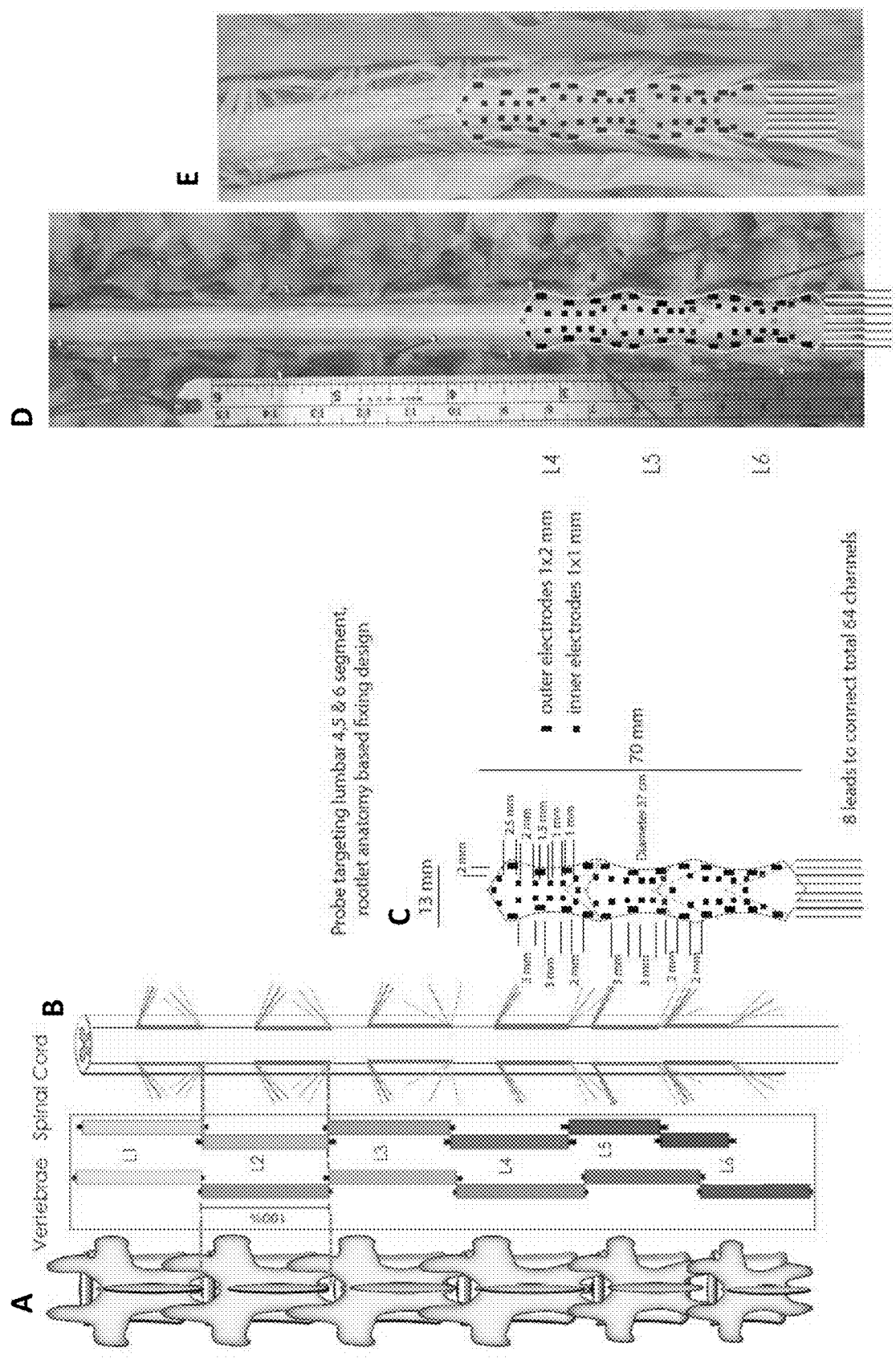
Figure 26:
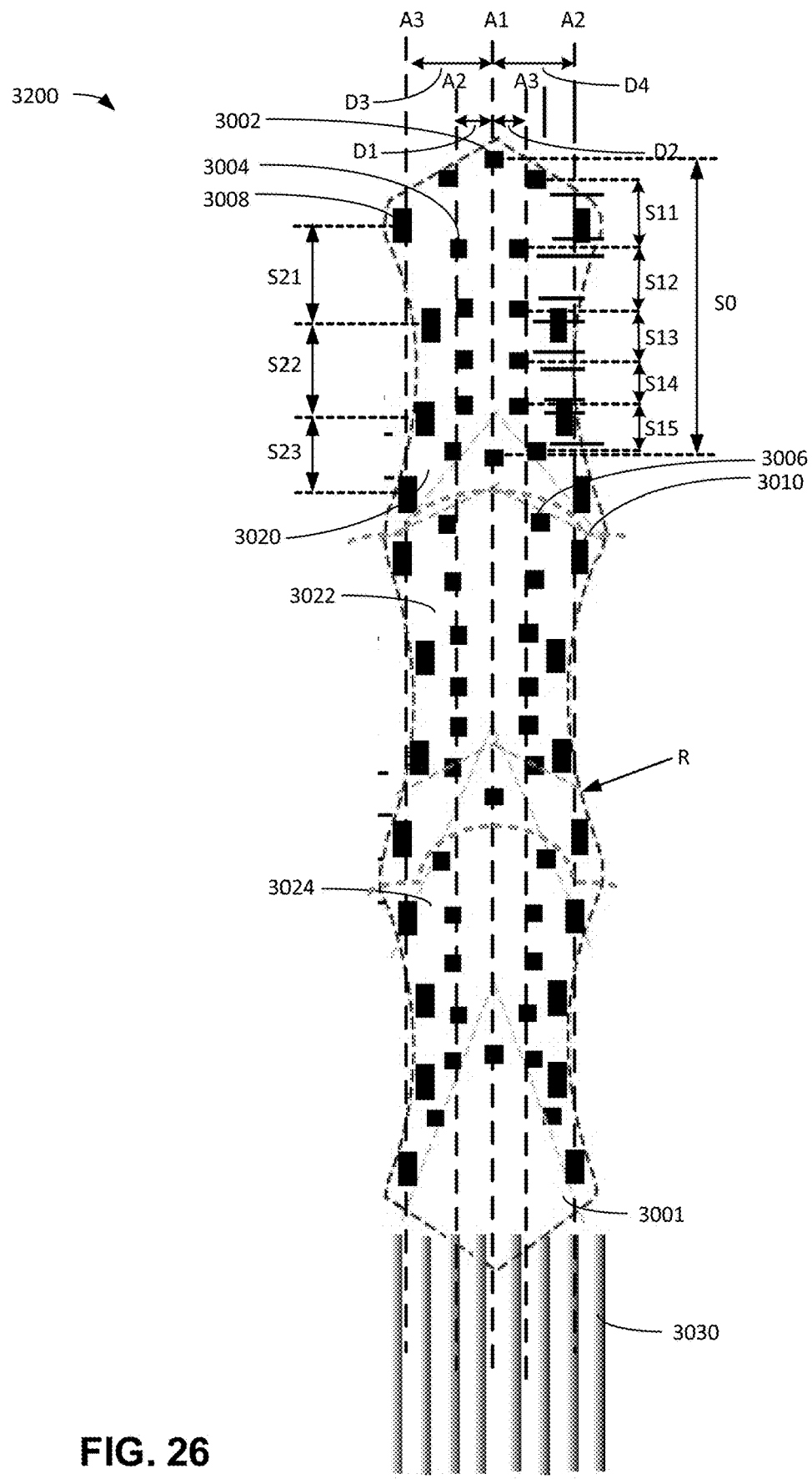
Figure 27:
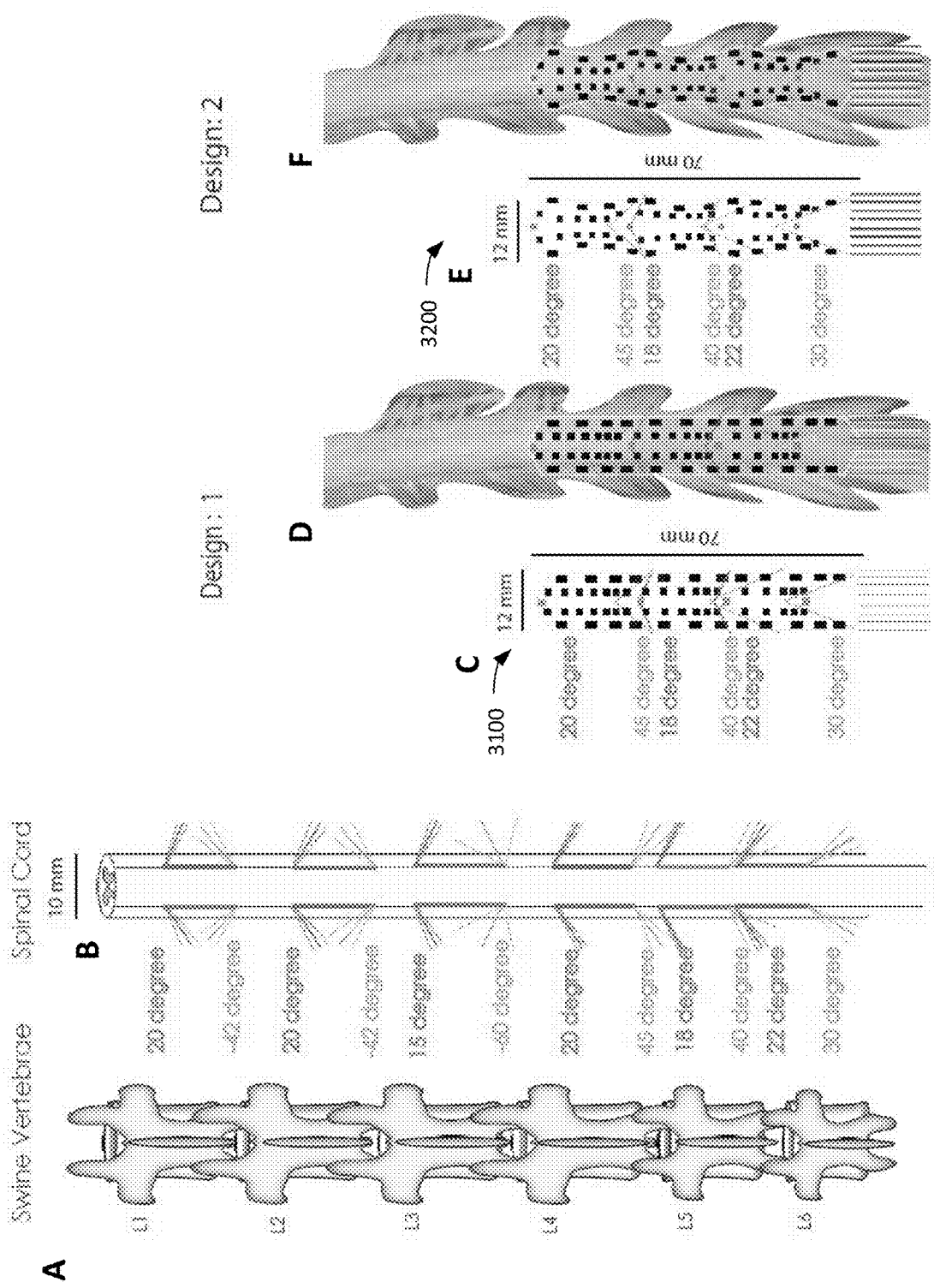

The first group of inner electrodes 3004 is arranged on the substrate along a first inner longitudinal axis A2 that is parallel to the central longitudinal axis A1. In some embodiments, as illustrated in FIGS. 21 and 22, the first group of inner electrodes 3004 can be arranged linearly along the first inner longitudinal axis A2, such that the inner electrodes 3004 are aligned along the first inner longitudinal axis A2. In other embodiments, the first group of inner electrodes 3004 can be arranged in a non-linear manner along the first inner longitudinal axis A2. In some examples, at least one of the inner electrodes 3004 is not aligned with the other inner electrodes 3004. In other examples, the inner electrodes 3004 can be arranged to be undulated along the first inner longitudinal axis A2, as illustrated in FIGS. 25 and 26. Other arrangements are also possible.

The second group of inner electrodes 3006 is arranged on the substrate along a second inner longitudinal axis A3 that is parallel to the central longitudinal axis A1. In some embodiments, as illustrated in FIGS. 21 and 22, the second group of inner electrodes 3006 can be arranged linearly along the second inner longitudinal axis A3, such that the inner electrodes 3006 are aligned along the second inner longitudinal axis A3. In other embodiments, the second group of inner electrodes 3006 can be arranged in a non-linear manner along the second inner longitudinal axis A3. In some examples, at least one of the inner electrodes 3006 is not aligned with the other inner electrodes 3006. In other examples, the inner electrodes 3006 can be arranged to be undulated along the second inner longitudinal axis A3, as illustrated in FIGS. 25 and 26 (showing certain electrodes offset to the left or right form the longitudinal axis A3). Other arrangements are also possible.

In some embodiments, the first and second inner longitudinal axes A2 and A3 are arranged symmetrically about the central longitudinal axis A1. In other embodiments, the first and second inner longitudinal axes A2 and A3 can be arranged asymmetrically about the central longitudinal axis A1. The first inner longitudinal axis A2 can be spaced from the central longitudinal axis A1 at a distance D1 ranging from about 0.5 mm to about 5.5 mm in some embodiments. The second inner longitudinal axis A3 can be spaced from the central longitudinal axis A1 at a distance D2 ranging from about 0.5 mm to about 5.5 mm in some embodiments.

In some embodiments, the first and second groups of inner electrodes 3004 and 3006 are arranged symmetrically with respect to the central longitudinal axis A1. In other embodiments, the first and second groups of inner electrodes 3004 and 3006 can be arranged asymmetrically about the central longitudinal axis A1.

The inner electrodes 3004 and 3006 in each of the first and second groups can be of various shapes, such as square, rectangle, circle, oval, etc. The inner electrodes 3004 and 3006 can be of the same shape. Alternatively, the inner electrodes 3004 and 3006 can vary in shape. The inner electrodes 3004 and 3006 in the first and second group can be of various dimensions. In one embodiment, the inner electrodes 3004 and 3006 are sized to be about 1×1 mm2. Other dimensions are also possible in other embodiments. The inner electrodes 3004 and 3006 can be of the same size. Alternatively, the inner electrodes 3004 and 3006 can vary in size.

The number of the inner electrodes 3004 and 3006 in each of the first and second groups can vary. In some embodiments, 18 inner electrodes in each of the first and second groups are provided as illustrated in FIG. 22. Other suitable numbers of inner electrodes 3004 and 3006 can be provided in other embodiments.

Figure 23:
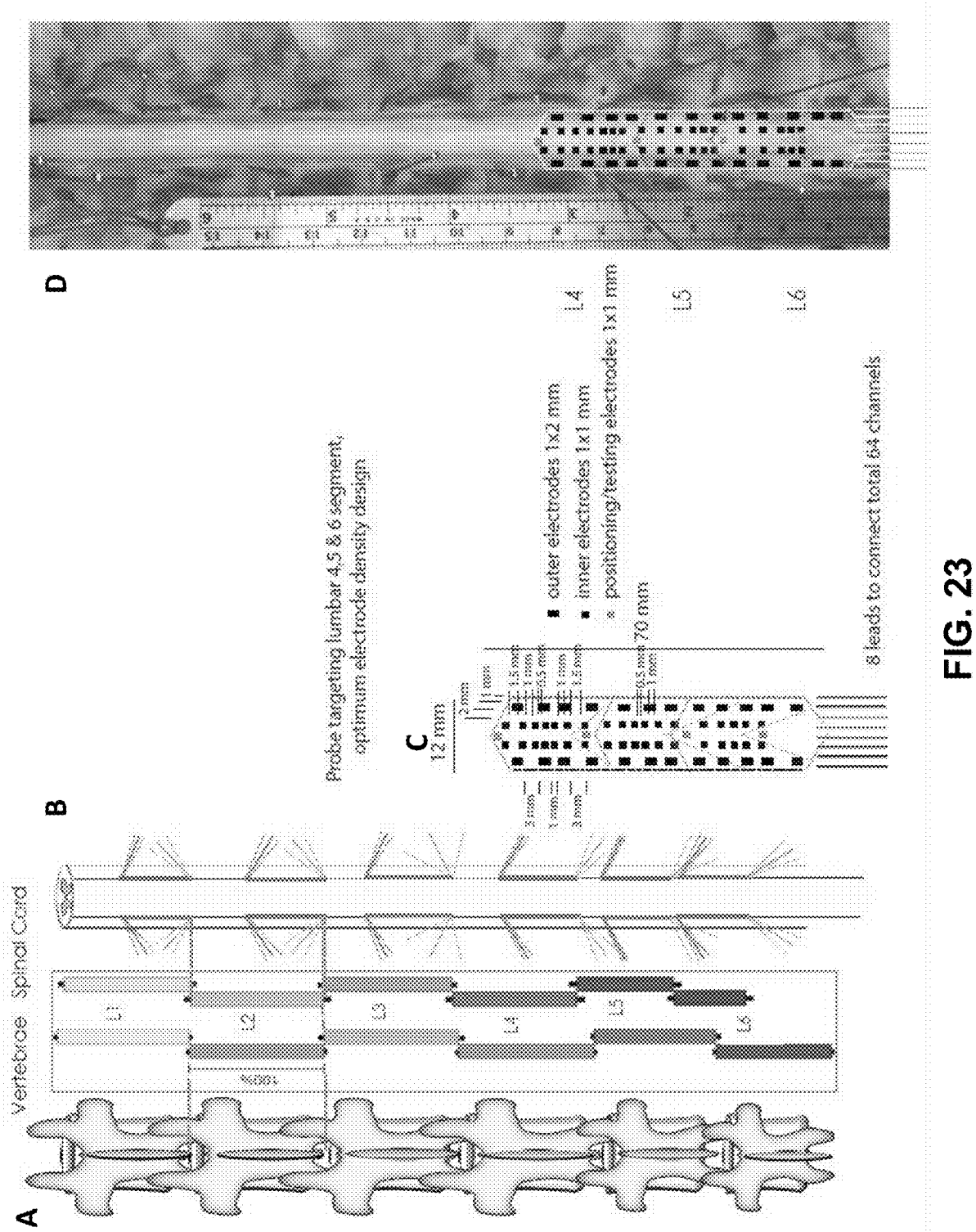
Figure 24:
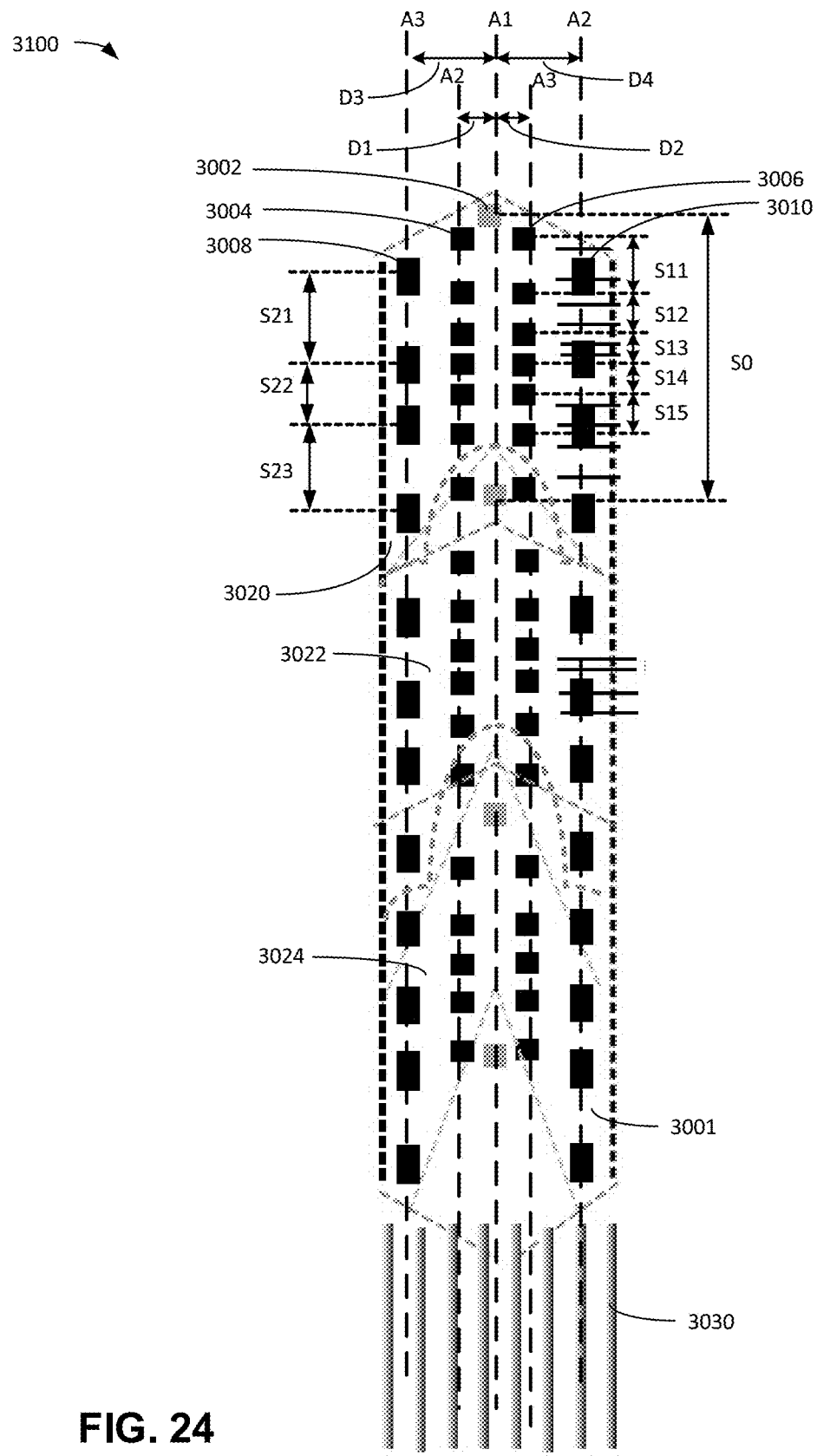

The inner electrodes 3004 and 3006 in each of the first and second groups can be spaced equally (uniformly) along the respective first and second inner longitudinal axis A2 and A3. For example, a spacing S1 (e.g., S11, S12, S13, S14, or S15) between adjacent inner electrodes 3004 or 3006 is shown as being identical to a spacing S1 between other adjacent inner electrodes 3004 or 3006. In other embodiments, as illustrated in FIGS. 23 and 24, a spacing S1 (e.g. S11, S12, S13, S14, or S15) between adjacent inner electrodes 3004 or 3006 can vary along the respective first and second inner longitudinal axis A2 and A3. In some embodiments, the spacing S1 (e.g. S11, S12, S13, S14, or S15) between adjacent inner electrodes 3004 or 3006 can range from about 0.5 mm to about 4 mm. In other embodiments, the spacing S1 (e.g. S11, S12, S13, S14, or S15) between adjacent inner electrodes 3004 or 3006 can be about 2 mm (or about 1 mm between opposing edges of adjacent inner electrodes). In other embodiments, other ranges for the spacing S1 are also possible.

Referring still to FIG. 22, the first group of outer electrodes 3008 is arranged on the substrate along a first outer longitudinal axis A4 that is parallel to the first inner longitudinal axis A2 (and thus to the central longitudinal axis A1). The first inner longitudinal axis A2 is positioned between the central longitudinal axis A1 and the first outer longitudinal axis A4.

In some embodiments, as illustrated in FIGS. 21 and 22, the first group of outer electrodes 3008 can be arranged linearly along the first outer longitudinal axis A4, such that the outer electrodes 3008 are aligned along the first outer longitudinal axis A4. In other embodiments, the first group of outer electrodes 3008 can be arranged in a non-linear manner along the first outer longitudinal axis A4. In some examples, at least one of the outer electrodes 3008 is not aligned with the other outer electrodes 3008. In other examples, the outer electrodes 3008 can be arranged to be undulated along the first outer longitudinal axis A4, as illustrated in FIGS. 25 and 26. Other arrangements are also possible.

The second group of outer electrodes 3010 is arranged on the substrate along a second outer longitudinal axis A5 that is parallel to the second inner longitudinal axis A3 (and thus to the central longitudinal axis A1). The second inner longitudinal axis A3 is positioned between the central longitudinal axis A1 and the second outer longitudinal axis A5.

In some embodiments, as illustrated in FIGS. 21 and 22, the second group of outer electrodes 3010 can be arranged linearly along the second outer longitudinal axis A5, such that the outer electrodes 3010 are aligned along the second outer longitudinal axis A5. In other embodiments, the second group of outer electrodes 3010 can be arranged in a non-linear manner along the second outer longitudinal axis A5. In some examples, at least one of the outer electrodes 3010 is not aligned with the other outer electrodes 3010. In other examples, the outer electrodes 3010 can be arranged to be undulated along the second outer longitudinal axis A5, as illustrated in FIGS. 25 and 26. Other arrangements are also possible.

In some embodiments, the first and second outer longitudinal axes A4 and A5 are arranged symmetrically about the central longitudinal axis A1. In other embodiments, the first and second outer longitudinal axes A4 and A5 can be arranged asymmetrically about the central longitudinal axis A1. The first outer longitudinal axis A4 can be spaced from the central longitudinal axis A1 at a distance ranging from about 1 mm to about 6 mm in some embodiments. The second outer longitudinal axis A5 can be spaced from the central longitudinal axis A1 at a distance ranging from about 1 mm to about 6 mm in some embodiments.

The outer electrodes 3008 and 3010 can be spaced apart from their adjacent longitudinal lateral edges of the substrate at predetermined distances. Such predetermined distances can range from about 0.3 mm to about 3 mm in some embodiments, or can be about 1.5 mm (e.g., about 1 mm between the lateral longitudinal edge of the substrate and the adjacent edge of the outer electrode) in other embodiments.

In some embodiments, the first and second groups of outer electrodes 3008 and 3010 are arranged symmetrically with respect to the central longitudinal axis A1. In other embodiments, the first and second groups of outer electrodes 3008 and 3010 can be arranged asymmetrically about the central longitudinal axis A1.

The outer electrodes 3008 and 3010 in each of the first and second groups can be of various shapes, such as square, rectangle, circle, oval, etc. The outer electrodes 3008 and 3010 can be of the same shape. Alternatively, the outer electrodes 3008 and 3010 can vary in shape. The outer electrodes 3008 and 3010 in the first and second group can be of various dimensions. In one embodiment, the outer electrodes 3008 and 3010 are sized to be about 1×2 mm2. Other dimensions are also possible in other embodiments. The outer electrodes 3008 and 3010 can be of the same size. Alternatively, the outer electrodes 3008 and 3010 can vary in size.

In some embodiments, the outer electrodes 3008 and 3010 are sized to be larger (e.g., in terms of surface or cross-sectional area) than the inner electrodes 3004 and 3006 and/or the central electrodes 3002. For example, the outer electrodes 3008 and 3010 are sized longer in the longitudinal direction than the inner electrodes 3004 and 3010 so that the longer outer electrodes 3008 and 3010 can cover wider variations of the rootlets at their tips (an distal end away from the spinal cord) while the rootlets vary less at their opposite ends (a proximate end close to the spinal cord). In other embodiments, the outer electrodes 3008 and 3010 are sized to be equal to, or smaller than, the inner electrodes 3004 and 3006 and/or the central electrodes 3002.

The number of the outer electrodes 3008 and 3010 in each of the first and second groups can vary on the substrate. In some embodiments, 12 outer electrodes in each of the first and second groups are provided as illustrated in FIG. 22. Other suitable numbers of outer electrodes 3008 and 3010 can be provided in other embodiments.

The outer electrodes 3008 and 3010 in each of the first and second groups can be spaced equally along the respective first and second outer longitudinal axis A4 and A5. For example, a spacing S2 (e.g., S21, S22, or S23) between adjacent outer electrodes 3008 or 3010 is identical to a spacing S2 between other adjacent outer electrodes 3008 or 3010. In other embodiments, as illustrated in FIGS. 23 and 24, the spacing between adjacent outer electrodes 3008 and 3010 can vary along the respective first and second outer longitudinal axis A4 and A5. In some embodiments, the spacing S2 (e.g., S21, S22, or S23) between adjacent outer electrodes 3008 or 3010 can range from about 1 mm to about 7 mm. In other embodiments, the spacing S2 (e.g., S21, S22, or S23) between adjacent outer electrodes 3008 or 3010 can be about 4 mm (or about 2 mm between opposing edges of adjacent outer electrodes). In other embodiments, other ranges for the spacing S2 are also possible.

The electrode array 3000 can further include one or more output leads 3030 configured to connect the electrodes in the substrate. In the illustrated example, 8 leads are provided to connect all the electrodes in the substrate. Other numbers of the output leads 3030 can be used in other embodiments.

Referring still to FIG. 22, the substrate can have a plurality of sections that are longitudinally arranged along the central longitudinal axis A1. In the illustrated example, three sections 3020, 3022, and 3024 are defined on the substrate to generally correspond to three lumbar segments (e.g., L4, L5, and L6) with which the substrate is engaged. The central electrodes 3002 are arranged over the sections along the central longitudinal axis A1. The first and second groups of inner electrodes 3004 and 3006 are arranged on the sections along the respective inner longitudinal axes A2 and A3. Similarly, the first and second groups of outer electrodes 3008 and 3010 are arranged on the sections along the respective outer longitudinal axes A4 and A5.

In some embodiments, each of at least some of the sections is similarly configured to include the same number of inner electrodes, and/or the same number of outer electrodes. In the illustrated example, each of the sections 3020, 3022, and 3024 is configured to include 6 inner electrodes 3004 and 3006 in each of the first and second groups and 4 outer electrodes 3008 and 3010 in each of the first and second groups. In other embodiments, however, at least one of the sections can have a different number of inner electrodes and/or a different number of outer electrodes.

In some embodiments, in each of at least some of the sections, the inner electrodes in the first and second groups can be spaced equally along the first and second inner longitudinal axes. In addition or alternatively, in each of at least some of the sections, the outer electrodes in the first and second groups can be spaced equally along the first and second outer longitudinal axes.

In other embodiments, in each of at least some of the sections, at least one set of adjacent electrodes in the first group of inner electrodes can be spaced at a different distance from at least another set of adjacent electrodes in the first group of inner electrodes. Similarly, in each of at least some of the sections, at least one set of adjacent electrodes in the second group of inner electrodes can be spaced at a different distance from at least another set of adjacent electrodes in the second group of inner electrodes. Further, in each of at least some of the sections, at least one set of adjacent electrodes in the first group of outer electrodes can be spaced at a different distance from at least another set of adjacent electrodes in the first group of outer electrodes. Similarly, in each of at least some of the sections, at least one set of adjacent electrodes in the second group of outer electrodes can be spaced at a different distance from at least another set of adjacent electrodes in the second group of outer electrodes.

Referring to FIGS. 23 and 24, a second example epidural stimulation electrode array 3100 is depicted. The electrode array 3100 is configured to provide an optimal electrode density. FIGS. 23A, B, and D illustrate information similar to that in FIGS. 21A, 21B, and 21D. The electrode array 3100 is illustrated in FIGS. 23C and 24. The electrode array 3100 in this example is configured similarly to the electrode array 3000 except for the arrangement (e.g., spacing) of the electrodes. Same reference numbers in FIGS. 22 and 24 represent the same or similar elements, and the description for the same or similar elements are omitted for brevity purposes. The description below is primarily directed to features of the electrode array 3100 different from the electrode array 3000.

In this example, a spacing S1 (e.g. S11, S12, S13, S14, or S15) between adjacent inner electrodes 3004 or 3006 varies along the respective first and second inner longitudinal axis A2 and A3. The spacing between adjacent inner electrodes can be determined based on anatomical analysis, in some examples. By way of example, in a first section 3020 of the three sections 3020, 3022, and 3024 of the substrate, the spacing S11 and S15 can range from about 2 mm to 3 mm in some embodiments, or can be about 2.5 mm (e.g., 1.5 mm between opposing edges of adjacent electrodes) in other embodiments. Further, the spacing S12 and S14 can range from about 1.5 mm to 2.5 mm in some embodiments, or can be about 2 mm (e.g., 1 mm between opposing edges of adjacent electrodes) in other embodiments. Moreover, the spacing S13 can range from about 1 mm to 2 mm in some embodiments, or can be about 1.5 mm (e.g., 0.5 mm between opposing edges of adjacent electrodes) in other embodiments. In some embodiments, the other sections 3022 and 3024 can be configured with identical or similar spacing configurations between 6 inner electrodes. In other embodiments, at least one of the other sections 3022 and 3024 can be configured with different spacing configurations between 6 inner electrodes.

Further, a spacing S2 (e.g., S21, S22, and S23) between adjacent outer electrodes 3008 and 3010 can vary along the respective first and second outer longitudinal axis A4 and A5. The spacing between adjacent outer electrodes can be determined based on anatomical analysis. By way of example, in the first section 3020 of the three sections 3020, 3022, and 3024 of the substrate, the spacing S21 and S23 can range from about 2 mm to 8 mm in some embodiments, or can be about 5 mm (e.g., 3 mm between opposing edges of adjacent electrodes) in other embodiments. Further, the spacing S22 can range from about 1 mm to 7 mm in some embodiments, or can be about 3 mm (e.g., 1 mm between opposing edges of adjacent electrodes) in other embodiments. In some embodiments, the other sections 3022 and 3024 can be configured with identical or similar spacing configurations between 4 outer electrodes. In other embodiments, at least one of the other sections 3022 and 3024 can be configured with different spacing configurations between 4 outer electrodes.

In addition to the advantages discussed above, the electrode array 3100 further provides electrodes optimized for various rootlet density. Anatomical studies show that the rootlet density is higher at the center of each spinal segment (where rootlet enters dorsal column). To increase possibility of reliable electric contact, the inner and outer electrodes in the electrode array 3100 are arranged such the electrode density is higher at the center in each section of the substrate and becomes gradually lower away from the center. Further, the electrode array 3100 provides lower density of electrode between adjacent sections (and thus between adjacent corresponding lumbar segments). Thus, the electrode array 3100 provides less chance of stimulation spillover between segments and is thus capable of better targeting each spinal segment.

Referring to FIGS. 25 and 26, a third example epidural stimulation electrode array 3200 is depicted. FIGS. 25A and B illustrate information similar to that in FIGS. 21A and 21B. FIGS. 25D and 25E illustrate information similar to that in FIG. 21D. For example, FIG. 25D shows the electrode array 3200 is arranged to straight lumbar segments, and FIG. 25E shows the electrode array 3200 is arranged to curved lumbar segments.

The electrode array 3200 is illustrated in FIGS. 25C and 26. The electrode array 3200 in this example is configured similarly to the electrode array 3000 except for the arrangement of the electrodes and/or the shape of the substrate. Same reference numbers in FIGS. 22 and 26 represent the same or similar elements, and the description for the same or similar elements are omitted for brevity purposes. The description below is primarily directed to features of the electrode array 3200 different from the electrode array 3000.

In this example, the inner electrodes 3004 and 3006 can be arranged in an undulating manner along the respective longitudinal inner axes A2 and A3. In addition or alternatively, the outer electrodes 3008 and 3010 can be arranged in an undulating manner along the respective longitudinal outer axes A4 and A5. In some embodiments, in each section of the three sections 3020, 3022, and 3024 of the substrate, the inner electrodes are arranged along a line that is curved inwardly toward the central longitudinal axis A1. In addition or alternatively, in each section of the three sections 3020, 3022, and 3024 of the substrate, the outer electrodes are arranged along a line that is curved inwardly toward the central longitudinal axis A1.

In some embodiments, the substrate is configured to have lateral outlines (e.g., edges) that follow the curved lines defined by the undulating arrangements of the outer electrodes. For example, in each section of the three sections 3020, 3022, and 3024, the substrate has opposite lateral edges that are curved inwardly to correspond to the undulatingly arranged outer electrodes. A radius of curvature of the lateral edge can range from about 200 mm to about 500 mm in some embodiments, or can be about 370 mm in other embodiments. Other ranges are also possible.

In addition, a spacing S1 (e.g. S11, S12, S13, S14, or S15) between adjacent inner electrodes 3004 or 3006 varies along the respective first and second inner longitudinal axis A2 and A3. The spacing between adjacent inner electrodes can be determined based on anatomical analysis. By way of example, in a first section 3020 of the three sections 3020, 3022, and 3024 of the substrate, the spacing S11 can range from about 1 mm to 6 mm in some embodiments, or can be about 3.5 mm (e.g., 2.5 mm between opposing edges of adjacent electrodes) in other embodiments. Further, the spacing S12 can range from about 1 mm to 4.5 mm in some embodiments, or can be about 3 mm (e.g., 2 mm between opposing edges of adjacent electrodes) in other embodiments. Moreover, the spacing S13 can range from about 1 mm to 3.5 mm in some embodiments, or can be about 2.5 mm (e.g., 1.5 mm between opposing edges of adjacent electrodes) in other embodiments. Further, the spacing S14 and S15 can range from about 1 mm to 3 mm in some embodiments, or can be about 2 mm (e.g., 1 mm between opposing edges of adjacent electrodes) in other embodiments. In some embodiments, the other sections 3022 and 3024 can be configured with identical or similar spacing configurations between 6 inner electrodes. In other embodiments, at least one of the other sections 3022 and 3024 can be configured with different spacing configurations between 6 inner electrodes.

Further, a spacing S2 (e.g., S21, S22, and S23) between adjacent outer electrodes 3008 and 3010 can vary along the respective first and second outer longitudinal axis A4 and A5. The spacing between adjacent outer electrodes can be determined based on anatomical analysis. By way of example, in the first section 3020 of the three sections 3020, 3022, and 3024 of the substrate, the spacing S21 and S22 can range from about 2 mm to 8 mm in some embodiments, or can be about 5 mm (e.g., 3 mm between opposing edges of adjacent electrodes) in other embodiments. Further, the spacing S22 can range from about 1 mm to 7 mm in some embodiments, or can be about 4 mm (e.g., 2 mm between opposing edges of adjacent electrodes) in other embodiments. In some embodiments, the other sections 3022 and 3024 can be configured with identical or similar spacing configurations between 4 outer electrodes. In other embodiments, at least one of the other sections 3022 and 3024 can be configured with different spacing configurations between 4 outer electrodes.

In addition to the advantages discussed above, the electrode array 3200 can in some embodiments further improve orientation of the electric fields emitted by the electrodes along the diverging rootlet projections. The curvature can provide leverage to fix the edges of the substrate between the rootlets entering into the spinal cord, thereby reducing migration of the electrode. Further, the rounded edges can prevent the substrate from imposing too much pressure on the rootlets, thereby reducing possibility of damage caused by the electrodes. Moreover, the flexibility of the substrate in combination with the rounded design can provide improved conformity of the probe with the spinal cord, which can provide improved therapeutic outcomes. Consistent contact between the electrodes and the spinal cord can also reduce the variability of stimulation outcome depending on the subject's posture (e.g., standing or supine) observed in subjects implanted with typical paddle arrays.

Figure 28:
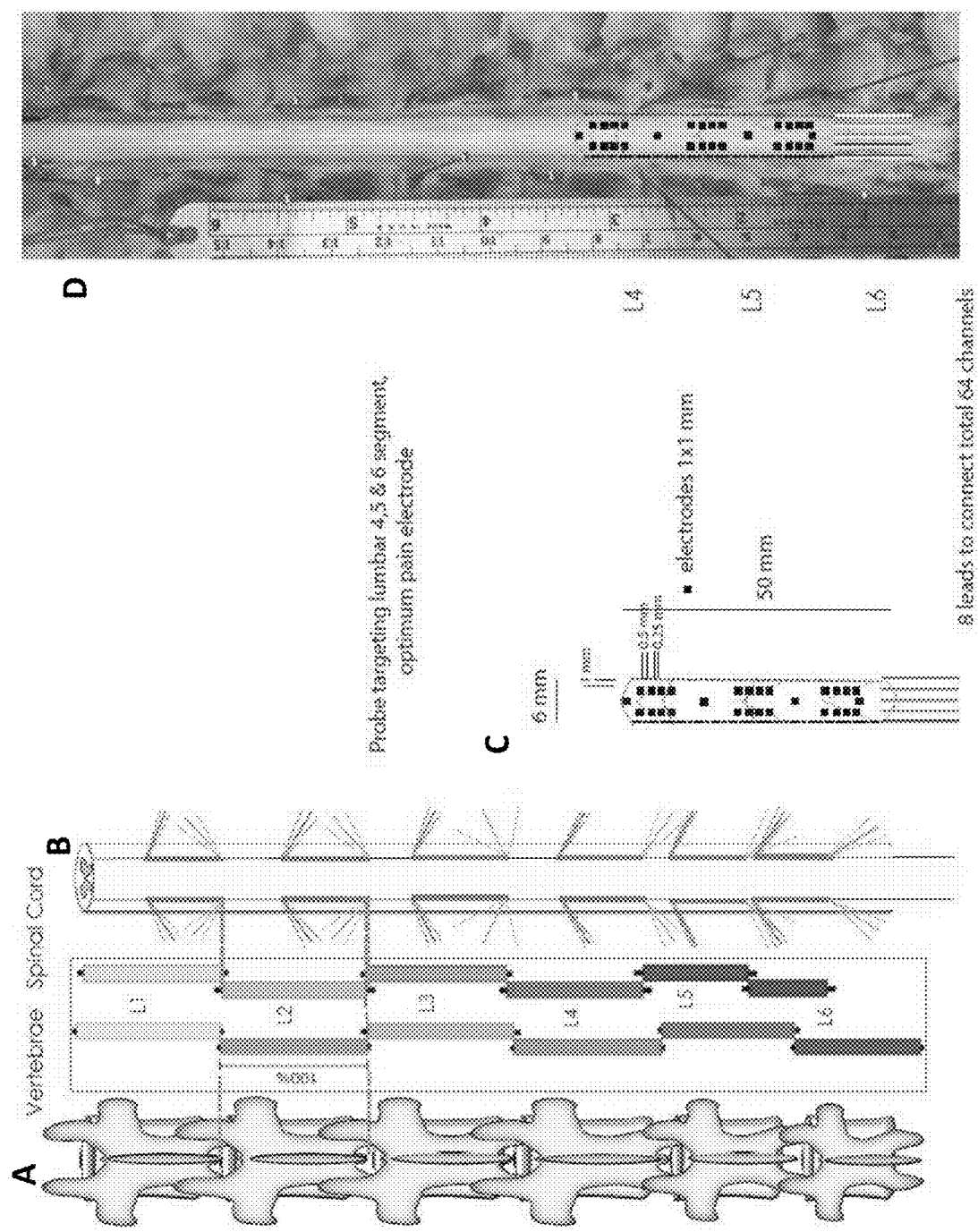
Figure 29:
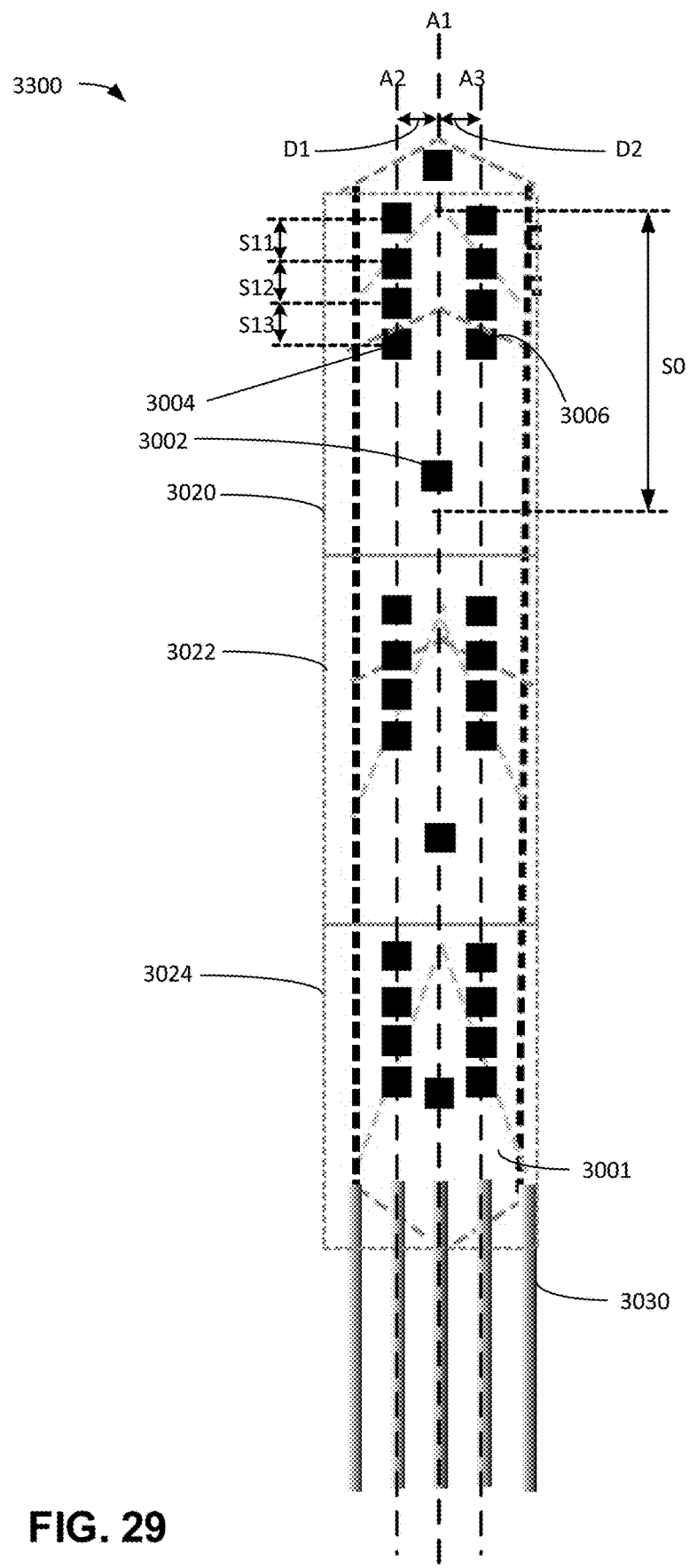

Referring to FIGS. 28 and 29, a fourth example epidural stimulation electrode array 3300 is described. The electrode array 3300 is configured to provide a design for blocking pain signals. FIGS. 28A, B, and D illustrate information similar to that in FIGS. 21A, 21B, and 21D. The electrode array 3300 are illustrated in FIGS. 28C and 29. The electrode array 3300 in this example is configured similarly to the electrode array 3000 except that two columns of electrodes are provided with the central electrodes arranged between them, instead of four columns of electrodes as shown in the electrode arrays 3000, 3100, and 3200. Same reference numbers in FIGS. 22 and 29 represent the same or similar elements, and the description for the same or similar elements are omitted for brevity purposes. The description below is primarily directed to features of the electrode array 3300 different from the electrode array 3000.

In this example, as the array 3300 includes only two columns of electrodes with the central electrodes, the substrate can be configured to be smaller than the other electrode arrays 3000, 3100, and 3200. For example, the length of the substrate can range from about 30 mm to about 70 mm, while the width of the substrate can range from about 3 mm to about 10 mm. In other embodiments, the substrate can be about 50 mm in length and 6 mm in width. Other configurations are also possible.

For ease of description, the pair of electrode columns in the array 3300 can be described as corresponding to the inner electrodes 3004 and 3006. It is understood, however, that the pair of electrode columns in the array 3300 can be described as corresponding to the outer electrodes 3008 and 3010.

In this example, the inner electrodes in each inner longitudinal axis have 4 electrodes in 1×1 mm2 each. Other numbers and sizes of electrodes are also possible.

In some embodiments, the inner electrodes 3004 and 3006 can be spaced equally along the respective inner longitudinal axes A2 and A3. In other embodiments, the spacing between adjacent inner electrodes 3004 and 3006 can vary along the respective first and second inner longitudinal axis A2 and A3. The spacing between adjacent inner electrodes can be determined based on anatomical analysis. By way of example, in a first section 3020 of the three sections 3020, 3022, and 3024 of the substrate, the spacing S11 can range from about 0.2 mm to 4 mm in some embodiments, or can be about 1.5 mm (e.g., 0.5 mm between opposing edges of adjacent electrodes) in other embodiments. Further, the spacing S12 and S13 can range from about 0.1 mm to 3 mm in some embodiments, or can be about 0.75 mm (e.g., 0.25 mm between opposing edges of adjacent electrodes) in other embodiments. In some embodiments, the other sections 3022 and 3024 can be configured with identical or similar spacing configurations between 6 inner electrodes. In other embodiments, at least one of the other sections 3022 and 3024 can be configured with different spacing configurations between 6 inner electrodes.

The electrode array 3300 can provide electrodes that are specific to segments to block pain signals from traveling upstream. The electrode tray 3300 provides anatomically correct designs that can target spinal columns only between targeted segments, thereby reducing stimulation spillover to the spinal rootlet and further reducing unwanted muscle contraction. Further, the electrode tray 3300 can block pain signals that originate across multiple segments. The electrode tray 3300 includes the intersegmental density specific design that provides high specificity without increasing the number of contacts required, thereby reducing amount of power required for stimulation.

Figure 30:
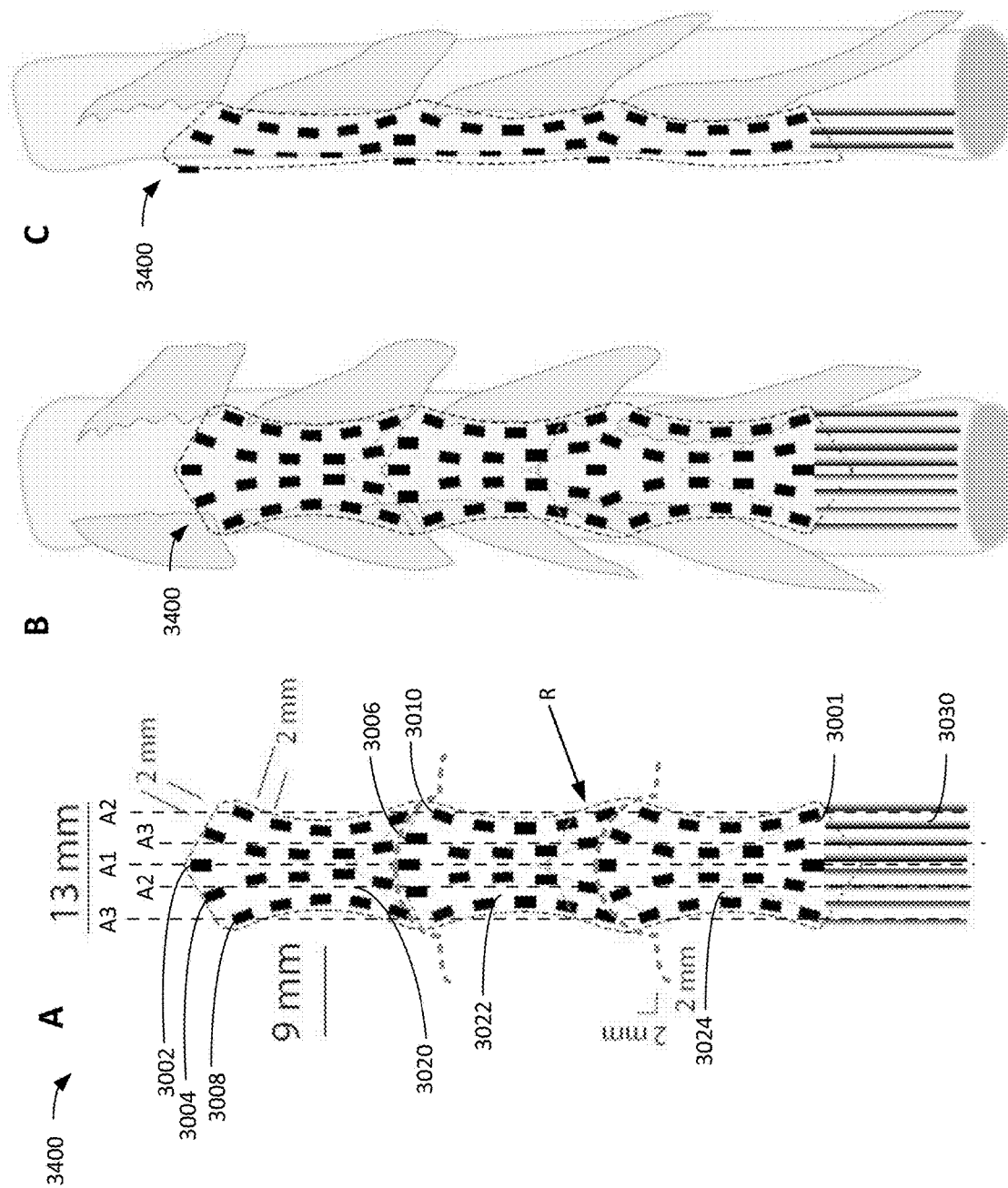

Referring to FIG. 30, a fifth example epidural stimulation electrode array 3400 is depicted. The electrode array 3400 is configured to provide a homogeneous contact density throughout a length of the electrode array (or a length of a section of the electrode array). FIG. 30A shows the electrode array 3400. FIG. 30B schematically depicts a top view of the electrode array 3400 engaged with desired lumbar segments, and FIG. 30C schematically depicts a side view of the electrode array 3400 engaged with desired lumbar segments. The electrode array 3400 in this example is configured similarly to the electrode array 3000, 3100, 3200, and/or 3300 except that the electrode array 3400 provides a homogeneous contact density. Same reference numbers in FIGS. 22, 24, 26, 29, and 30 represent the same or similar elements, and the description for the same or similar elements are omitted for brevity purposes. The description below is primarily directed to features of the electrode array 3400 different from the other electrode arrays described above.

Similarly to the electrode array 3200, the electrode array 3400 includes the inner electrodes 3004 and 3006 arranged in an undulating manner along the respective longitudinal inner axes A2 and A3. In addition or alternatively, the outer electrodes 3008 and 3010 can be arranged in an undulating manner along the respective longitudinal outer axes A4 and A5. In some embodiments, in each section of the three sections 3020, 3022, and 3024 of the substrate, the inner electrodes are arranged along a line that is curved inwardly toward the central longitudinal axis A1. In addition or alternatively, in each section of the three sections 3020, 3022, and 3024 of the substrate, the outer electrodes are arranged along a line that is curved inwardly toward the central longitudinal axis A1.

In some embodiments, the substrate is configured to have lateral outlines (e.g., edges) that follow the curved lines defined by the undulating arrangements of the outer electrodes. For example, in each section of the three sections 3020, 3022, and 3024, the substrate has opposite lateral edges that are curved inwardly to correspond to the undulatingly arranged outer electrodes. A radius of curvature of the lateral edge can range from about 200 mm to about 500 mm in some embodiments, or can be about 370 mm in other embodiments. Other ranges are also possible.

The electrode array 3400 is designed to match the spinal cord and rootlet anatomy. The curvatures of the electrode array 3400 can help conform to the rootlets, and secure it in place over time and reduce mitigation. The electrode array 340 can provide a homogeneous electrode density (or a homogeneous contact density), which can target all rootlets equally. The homogeneous electrode density can be provided by distributing electrodes evenly throughout a length of the array (or a length of a section of the array). In some implementations, stimulating electrode pairs are oriented to the angle of rootlets entering the dorsal column so as to be capable of activating with a minimum threshold, thereby resulting in minimum power required by the stimulator. The orientation specific design of the electrode array 3400 can reduce the chance of stimulation spillover to the other side of the spinal cord and eliminate a phase contradicting stimulation effect.

The electrodes in the electrode array 3400 can be made for any segment of the spinal cord. The soft electrode structure of the electrode array 3400 can conform nicely around the spinal cord without putting extra pressure on the roots.

Figure 31:
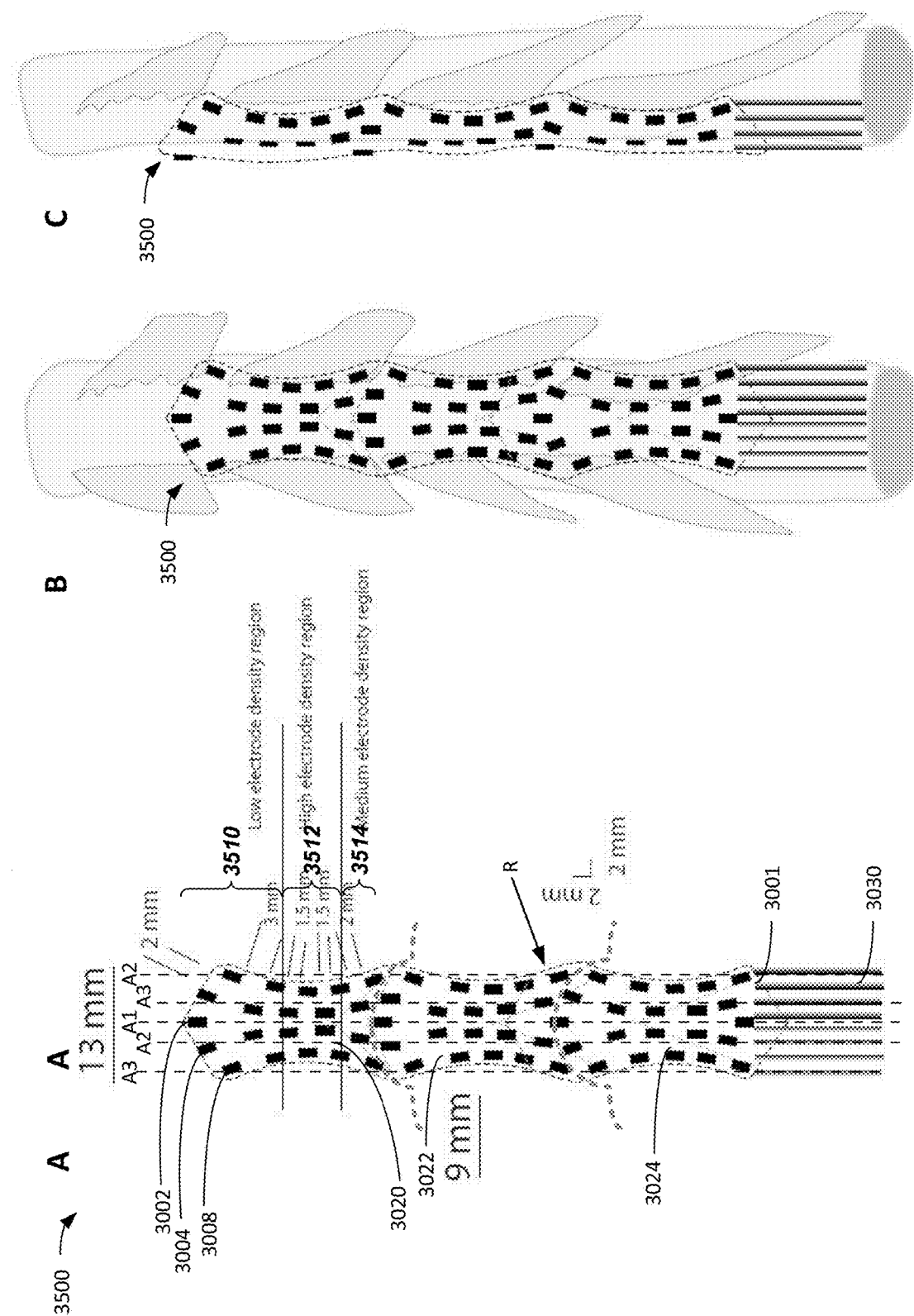

Referring to FIG. 31, a sixth example epidural stimulation electrode array 3500 is depicted. The electrode array 3500 is configured to provide a variable contact density throughout a length of the electrode array (or a length of a section of the electrode array). FIG. 31A shows the electrode array 3500. FIG. 31B schematically depicts a top view of the electrode array 3500 engaged with desired lumbar segments, and FIG. 30C schematically depicts a side view of the electrode array 3500 engaged with desired lumbar segments. The electrode array 3500 in this example is configured similarly to the electrode array 3000, 3100, 3200, 3300, and/or 3400 except that the electrode array 3500 provides a variable contact density. Same reference numbers in FIGS. 22, 24, 26, 29, 30, and 31 represent the same or similar elements, and the description for the same or similar elements are omitted for brevity purposes. The description below is primarily directed to features of the electrode array 3500 different from the other electrode arrays described above.

Similarly to the electrode array 3200, the electrode array 3500 includes the inner electrodes 3004 and 3006 arranged in an undulating manner along the respective longitudinal inner axes A2 and A3. In addition or alternatively, the outer electrodes 3008 and 3010 can be arranged in an undulating manner along the respective longitudinal outer axes A4 and A5. In some embodiments, in each section of the three sections 3020, 3022, and 3024 of the substrate, the inner electrodes are arranged along a line that is curved inwardly toward the central longitudinal axis A1. In addition or alternatively, in each section of the three sections 3020, 3022, and 3024 of the substrate, the outer electrodes are arranged along a line that is curved inwardly toward the central longitudinal axis A1.

In some embodiments, the substrate is configured to have lateral outlines (e.g., edges) that follow the curved lines defined by the undulating arrangements of the outer electrodes. For example, in each section of the three sections 3020, 3022, and 3024, the substrate has opposite lateral edges that are curved inwardly to correspond to the undulatingly arranged outer electrodes. A radius of curvature of the lateral edge can range from about 200 mm to about 500 mm in some embodiments, or can be about 370 mm in other embodiments. Other ranges are also possible.

The electrode array 3500 is similarly configured to the electrode array 3400 except for a variable contact density (or a variable electrode density) instead of the homogeneous contact density of the electrode array 3400. A variable electrode density can be provided by distributing electrodes (or contacts) unevenly along a length of the array (or a length of a section of the array). Such a variable electrode density of the electrode array 3500 can be configured such that the array can target different regions of the rootlet with multiple (e.g., three) different electrode densities. For example, each of the sections 3020, 3022, and 3024 has different electrode density regions, such as a low electrode density region 3510, a high electrode density region 3512, and a medium electrode density region 3514, as illustrated in FIG. 31. In the illustrated example, the low, high, and medium electrode density regions 3510, 3512, and 3514 are arranged in this order from the distal end of the array. Other arrangements of these regions may be possible. The density of each of these regions 3510, 3512, and 3514 can be determined to conform to the predetermined regions of the rootlets.

Figure 32:
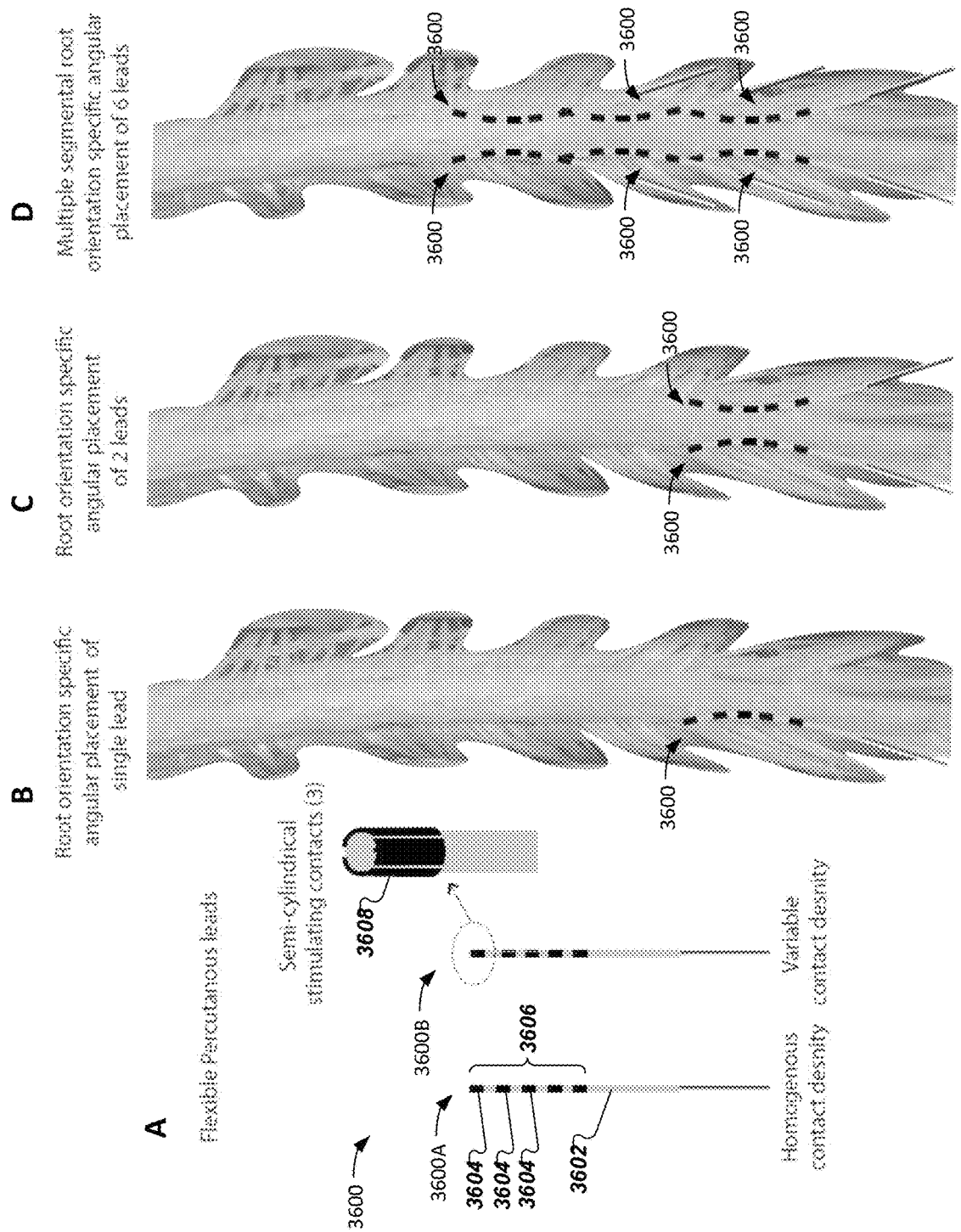

Referring to FIG. 32, an example epidural stimulation electrode lead 3600 is depicted. The electrode lead 3600 is configured as a flexible percutaneous lead. One or more electrode leads 3600 can be used to target spinal cord rootlets. FIG. 32A illustrates an electrode lead 3600A having a homogeneous contact density of electrodes, ad FIG. 32A also illustrates an electrode lead 3600B having a variable contact density of electrodes. FIG. 32B illustrates a root orientation specific angular placement of a single electrode lead 3600 engaged with a desired lumbar segment, and FIG. 32C illustrates a root orientation specific angular placement of two electrode leads 3600 engaged with a desired lumbar segment. FIG. 32D illustrates multiple segmental root orientation specific angular placement of six electrode leads 3600 engaged with desired lumbar segment.

The electrode lead 3600 can include a flexible lead wire body 3602 and an array 3606 of electrode contacts 3604. The array 3606 includes a plurality of rows of electrode contacts and is disposed along a distal portion of the lead wire body 3602. Each of the plurality of rows can include multiple semi-cylindrical stimulating contacts 3608 disposed around an axial center of the lead wire body 3602. The plurality of rows can arranged at an identical distance to provide a homogeneous contact density 3600A. Alternatively, the plurality of rows can be arranged at variable distances to provide a variable contact density 3600B.

In some implementations, the electrode lead 3600 can be less invasive than array designs. The electrode lead 3600 can be placed around the root at a specific angle so as to allow activating certain roots in a rootlet. The electrode lead 3600 includes multiple (e.g., three in the Figure) semi-cylindrical stimulating contacts which can form a cylindrical shape around the lead. Any two of the contacts can be used to generate a bipolar electric field. As depicted in FIG. 32A, the electrode lead 3600 can be of a homogeneous contact density 3600A or a variable contact density 3600B, which can be selectively used to target different rootlets more specifically. In operation, one or more of the electrode leads 3600 can be inserted based on the severity and location of the injury. Each of the electrode leads 3600 can be bent to mimic the angle at which the rootlets enter the spinal cord. For example, the bending of the electrode leads can be performed based on individual imaging and/or anatomical data collected from cadavers.

Example Implementation #1

Abstract

Background. Spinal networks that are disconnected from the brain as a result of complete spinal cord injury (SCI) can be facilitated via epidural electrical stimulation (EES) to enable standing after paraplegia. A previous study reported case of complete SCI in which EES enabled standing and volitional control of step-like leg movements while suspended in a harness. This study set out to determine if EES in the presence of a multi-modal rehabilitation (MMR) paradigm could enable walking in the same subject.

Methods. A 26-year-old male, with complete sensorimotor paralysis below T6, was implanted with an EES system at T11-L1. After 3 weeks of surgical recovery and 4 weeks of EES optimization, EES was used for 43 weeks to enable motor activities during MMR sessions. MMR sessions included seated, standing, and treadmill stepping activities with trainer assistance and body weight support provided as needed.

Results. During EES+MMR, the subject recovered the ability to walk on a treadmill using his arms on support bars for balance. Additionally, EES enabled walking over ground while using a front-wheeled walker and trainer assistance at the hips for balance. As walking performance improved, muscle activity profiles during select phases of the step cycle significantly changed ($p<0.001$) and step cycle duration significantly decreased ($p<0.001$).

Conclusion. This example demonstrated that EES-facilitation of spinal networks caudal to complete SCI enabled walking when combined with a rehabilitation paradigm focused on recovering step function after complete paraplegia.

Introduction

Conventional rehabilitation paradigms focus on compensation strategies to achieve independence during activities of daily living after complete SCI. Locomotor training, defined as activity-dependent trainer-assisted therapy that is focused on functional recovery while minimizing compensation strategies and attempting to activate neuromuscular systems below the level of injury (see Harkema S J, Hillyer J, Schmidt-Read M, Ardolino E, Sisto S A, Behrman A L. Locomotor Training: As a Treatment of Spinal Cord Injury and in the Progression of Neurologic Rehabilitation. Archives of Physical Medicine and Rehabilitation 2012; 93(9):1588-97), has been shown to improve walking speed in subjects with motor incomplete SCI during over ground and treadmill-based training. (see Field-Fote E C, Roach K E. Influence of a locomotor training approach on walking speed and distance in people with chronic spinal cord injury: a randomized clinical trial. Phys Ther 2011; 91(1):48-60; Harkema S J, Schmidt-Read M, Lorenz D J, Edgerton V R, Behrman A L. Balance and ambulation improvements in individuals with chronic incomplete spinal cord injury using locomotor training-based rehabilitation. Archives of Physical Medicine and Rehabilitation 2012; 93(9):1508-17). However, these subjects possessed the ability to volitionally generate a reciprocal, alternating flexion/extension stepping pattern prior to participating in locomotor training. These cases did not report subjects with motor complete SCI have not demonstrated improved walking ability after treadmill or over ground locomotor training. See Forrest G F, Sisto S A, Barbeau H, et al. Neuromotor and musculoskeletal responses to locomotor training for an individual with chronic motor complete AIS-B spinal cord injury. The Journal of Spinal Cord Medicine 2008; 31(5):509-21; Dobkin B, Apple D, Barbeau H, et al. Weight-supported treadmill vs over-ground training for walking after acute incomplete SCI. Neurology 2006; 66(4):484-93;

In one case, a male was reported with complete T6 paraplegia due to a traumatic SCI three years prior to study enrollment. See Grahn P J, Lavrov I A, Sayenko D G, et al. Enabling Task-Specific Volitional Motor Functions via Spinal Cord Neuromodulation in a Human With Paraplegia. Mayo Clinic Proceedings 2017; 92(4):544-54. The subject underwent 22 weeks of rehabilitation followed by implantation of an EES system. EES enabled self-assisted standing and volitional control over step-like leg movements when side-lying and when suspended vertically using a body weight support (BWS) system.

The study that is the subject of this example set out to determine if continued use of EES in the presence of a multi-modal rehabilitation (MMR) paradigm could enable walking in the same subject. The MMR paradigm was comprised of supine, side-lying with legs suspended, seated, standing and walking activities with trainer assistance and BWS support provided as needed.

Methods

The study that is the subject of this example was performed under the approval of the Mayo Clinic Institutional Review Board with a U.S. Food and Drug Administration Investigational Device Exemption (IDE G150167, NCT02592668).

Figures 3A, 3B:
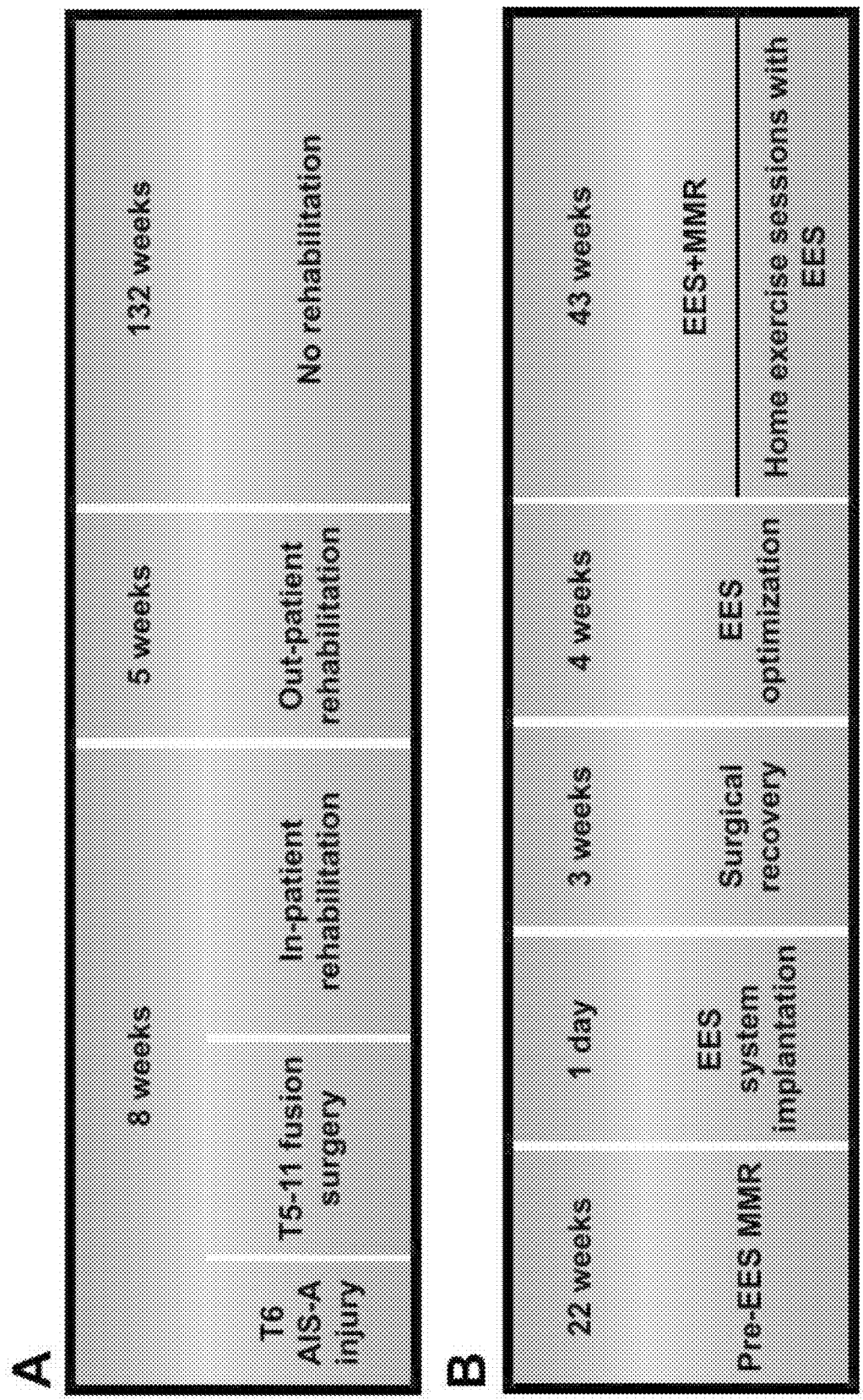
FIGS. 3A and 3B show representations of a subject's spinal cord injury (SCI) history and clinical timeline. Panel A shows the duration of time from sustaining a T6 AIS-A (American Spinal Injury Association Impairment Scale) injury to discharging from in-patient rehabilitation was 8 weeks followed by 5 weeks of outpatient rehabilitation. No rehabilitation was completed for 132 weeks prior to beginning this clinical trial. Panel B shows the subject completed 22 weeks (61 sessions) of multi-modal rehabilitation (MMR) prior to implantation of the EES (epidural electrical stimulation) system. Surgical implantation of the EES system was completed in 1 day, followed by 3 weeks of surgical recovery. After recovery, 4 weeks of EES optimization (14 sessions total) were comprised of trialing a select range of stimulation parameters to identify EES settings that enabled volitional control of flexion and extension leg movements in supine side-lying, or standing positions, as well as volitional control of rhythmic leg activities. Following EES optimization, 43 weeks of EES+MMR (multi-modal rehabilitation) (113 sessions in the laboratory and 72 self-administered home exercise sessions with EES) were completed. (Key: "T" refers to thoracic)

Description of Study Subject. A 26-year-old male sustained a complete SCI at the sixth thoracic vertebrae three years prior to study enrollment (FIGS. 3A-3B). Following injury onset, the spine was surgically fused from the T5-11 vertebrae. Next, eight weeks of inpatient rehabilitation and five weeks of outpatient compensatory rehabilitation were completed, all of which focused on gaining independence for activities of daily living from a wheelchair. For the next 132 weeks, the subject did not perform rehabilitation.

Pre-EES Multi-Modal Rehabilitation. Upon joining the study, the subject performed 22 weeks of MMR (61 sessions total) prior to EES implantation to determine if spontaneous motor recovery would occur from MMR. Sessions consisted of attempts to volitionally activate paralyzed muscles while positioned supine and side-lying, during seated trunk strengthening activities, standing, and treadmill stepping. Trainer assistance and BWS was provided during pre-EES MMR activities.

EES System Implantation. A 16-contact electrode array (SPECIFY 5-6-5, MEDTRONIC, Fridley, MN) was placed over the dorsal epidural surface of the spinal cord. Initial array positioning at the T11-L1 vertebrae was guided via intraoperative X-ray fluoroscopy. Once inserted, select electrodes on the array were activated intraoperatively and electrically-evoked spinal motor evoked potentials were recorded via intramuscular electromyography (EMG) of select leg muscles to confirm array positioning over the lumbosacral spinal cord enlargement (L2-S1 spinal segments). See Grahn P J, Lavrov I A, Sayenko D G, et al. Enabling Task-Specific Volitional Motor Functions via Spinal Cord Neuromodulation in a Human With Paraplegia. Mayo Clinic Proceedings 2017; 92(4):544-54; Sayenko D G, Atkinson D A, Dy C J, et al. Spinal segment-specific transcutaneous stimulation differentially shapes activation pattern among motor pools in humans. Journal of Applied Physiology 2015; 118(11):1364-74; Sayenko D G, Angeli C, Harkema S J, Edgerton V R, Gerasimenko Y P. Neuromodulation of evoked muscle potentials induced by epidural spinal-cord stimulation in paralyzed individuals. Journal of Neurophysiology 2014; 111(5):1088-99. The array was connected to an implanted pulse generator (RESTORE SENSOR SURE-SCAN MRI, MEDTRONIC, Fridley, MN) that was inserted subcutaneously in the right upper quadrant of the abdomen. The subject was instructed to rest at home for approximately three weeks before returning to the laboratory for four weeks of EES optimization to enable motor function below the level of injury.

Refinement of EES Settings to Enable Motor Function. A biphasic, charge-balanced waveform with a positive pulse width of 0.21 ms was used throughout the study. Initial active electrode configurations were chosen based on intraoperative electrically-evoked spinal motor potentials with reference to previously established topographical maps of electrically-evoked lumbosacral spinal motor potentials. See Grahn P J, Lavrov I A, Sayenko D G, et al. Enabling Task-Specific Volitional Motor Functions via Spinal Cord Neuromodulation in a Human With Paraplegia. Mayo Clinic Proceedings 2017; 92(4):544-54; Sayenko D G, Atkinson D A, Dy C J, et al. Spinal segment-specific transcutaneous stimulation differentially shapes activation pattern among motor pools in humans. Journal of Applied Physiology 2015; 118(11):1364-74; Sayenko D G, Angeli C, Harkema S J, Edgerton V R, Gerasimenko Y P. Neuromodulation of evoked muscle potentials induced by epidural spinal-cord stimulation in paralyzed individuals. Journal of Neurophysiology 2014; 111(5):1088-99; Sayenko D G, Atkinson D A, Floyd T C, et al. Effects of paired transcutaneous electrical stimulation delivered at single and dual sites over lumbosacral spinal cord. Neuroscience Letters 2015; 609(C): 229-34. An initial frequency range of 15-40 Hz was used based on prior literature reporting EES-facilitation of tonic and rhythmic motor activity generated by the human spinal cord. See Dimitrijevic M R, Gerasimenko Y, Pinter M M. Evidence for a spinal central pattern generator in humans. Ann NY Acad Sci 1998; 860:360-76; Minassian K, Jilge B, Rattay F, et al. Stepping-like movements in humans with complete spinal cord injury induced by epidural stimulation of the lumbar cord: electromyographic study of compound muscle action potentials. Spinal Cord 2004; 42(7):401-16; Danner S M, Hofstoetter U S, Freundl B, et al. Human spinal locomotor control is based on flexibly organized burst generators. Brain 2015; 138(3):577-88; Carhart M, He J, Herman R, D'Luzansky S, Willis W. Epidural Spinal-Cord Stimulation Facilitates Recovery of Functional Walking Following Incomplete Spinal-Cord Injury. IEEE Trans Neural Syst Rehabil Eng 2004; 12(1):32-42. During four weeks of EES optimization (14 sessions total), electrode configurations, stimulation frequencies, and voltage intensities were identified that enabled voluntary control of leg flexion and extension movements, standing, and step-like leg movements while suspended, all of which were previously reported in detail. See Grahn P J, Lavrov I A, Sayenko D G, et al. Enabling Task-Specific Volitional Motor Functions via Spinal Cord Neuromodulation in a Human With Paraplegia. Mayo Clinic Proceedings 2017; 92(4):544-54.

MMR Approach in the Presence of EES. EES settings found to enable volitional control of stand and step-like leg movements were used during MMR sessions (EES+MMR) to enable standing and stepping on a treadmill and over ground with trainer assistance and BWS as needed. Treadmill speed, trainer assistance and BWS were adjusted in the presence of EES to achieve appropriate stride length and leg movement patterns. Over ground training focused on decreasing BWS while maximizing independence and optimizing alignment and posture through trainer-guided positioning of the legs during gait. For 43 weeks (113 sessions total), EES settings, trainer assistance, amount of BWS, and the speed of the treadmill were adjusted during MMR to enable maximum independence during EES-enabled activities.

During week 23 of EES+MMR, a stimulation paradigm consisting of two interleaved programs that were symmetric with respect to electrode configuration was identified to enable bilateral volitional control over walking. The interleaved EES-paradigm provided independent adjustment of voltage intensity for each program to allow leg-specific optimization of EES-enabled volitional control over motor activity. Voltage intensities for each program were adjusted during each EES+MMR session based on the subject's verbal description of a stimulation-induced paresthesia that was perceived to change as EES voltages reached intensities that were optimal to enable volitional control of motor activity.

In addition to the 113 EES+MMR sessions performed in the rehabilitation laboratory, the subject independently completed 72 exercise sessions with EES at home on days that he did not come to the laboratory (FIGS. 3A-3B). Home exercise sessions consisted of attempts to volitionally control leg flexion and extension movement patterns, trunk extension, balance and reaching activities while seated, and static standing using EES parameters that were identified by the research team to enable the respective tasks.

Clinical and Neurophysiologic Evaluation. Clinical and neurophysiologic evaluations were performed at the start of the study, after 22 weeks of pre-EES MMR, after 3 weeks of surgical recovery, at week 25 of EES+MMR, and at the end of the study (week 43). At these time points, motor and sensory function was assessed using the International Standards for Neurological Classification of Spinal Cord Injury to classify the ASIA (American Spinal Injury Association) Impairment Scale (AIS). Additionally, transcranial magnetic stimulation motor evoked potentials recorded from major muscles below the SCI, and somatosensory evoked potentials recorded over the scalp and lumbar spine region were used to detect the presence of intact motor and sensory circuitry across the injury, respectively.

Results

Clinical and Neurophyiologic Evaluation. Clinical evaluations performed throughout the study showed no change from AIS-A classification. Transcranial magnetic stimulation over the scalp elicited motor evoked potentials in muscles above the level of injury that displayed normal latency ranges. However, responses were not present in recordings from muscles below the level of injury. Tibial somatosensory evoked potentials were within normal latency range when recorded at peripheral and lumbar spine sites, but were not present in recordings over the scalp. Altogether, these results indicate the subject maintained a complete SCI diagnosis throughout the study with no detectable neural signals passing through the injury.

EES-Enabled Walking on a Treadmill

Week 4 of EES+MMR. At week 4, a single EES program (anode: 8; cathodes: 4,10,15; 0.21 ms; 25 Hz; 5.0 V) was applied in a non-patterned fashion (FIG. 4A) while the subject attempted to walk on a treadmill moving at 0.35 m/s (FIG. 4B). In order to achieve stepping with EES at week 4, 30% BWS and trainer assistance at the hip, knee, and ankle of each leg was required (FIG. 4B). Rectus femoris (RF) activity was characterized by bursts during the stance phase with inhibition during the swing phase (FIGS. 4C and 2D). Medial hamstring (MH) activity was characterized by tonic activation throughout the step cycle. Significantly higher RF activation ($p<0.001$) occurred during the stance phase of the left leg while co-contraction of the RF and MH occurred in the right leg during stance (FIG. 4E). During the early swing phase of both legs, RF activity was inhibited significantly compared to MH ($p<0.001$) and RF activity remained inhibited compared to MH during the late swing phase of the left leg ($p<0.001$). However, the right RF and MH were co-contracted during the late swing phase.

Week 43 of EES+MMR. At week 43, two interleaved programs, symmetric with respect to electrode configuration, were used to independently adjust voltage intensity for each program (program 1 consisted of anodes: 2,8; cathodes: 4,10; 0.21 ms; 20 Hz, 3.3 V and program 2: anodes: 8,13; cathodes: 10,15; 0.21 ms; 20 Hz; 3.7 V) (FIG. 4F). The interleaved EES paradigm enabled walking on the treadmill at a speed of 0.22 m/s without trainer assistance and no BWS. During walking the subject maintained upper body balance via hand placement on support bars to facilitate anterolateral weight shifting during gait (FIG. 4G). Bursts of RF activation appeared during the stance phase with inhibition during the early part of the swing phase (FIGS. 4H and 2I). MH activity was characterized by tonic activity during stance and bursts of activation during the swing phase with reciprocal inhibition of RF activity. For both legs, co-contraction of the RF and MH occurred during the stance phase (FIG. 4J). During the early swing phase of both legs, RF activity was significantly inhibited ($p<0.001$) compared to MH activity. At the late swing phase, activation profiles demonstrated a significant increase in RF activity compared to MH ($p<0.001$). In summary, the use of two interleaved EES programs appeared to enable significant changes in muscle activity profiles during the late swing phase that coincided with the ability to walk self-assisted.

Figures 5A, 5B, 5C:
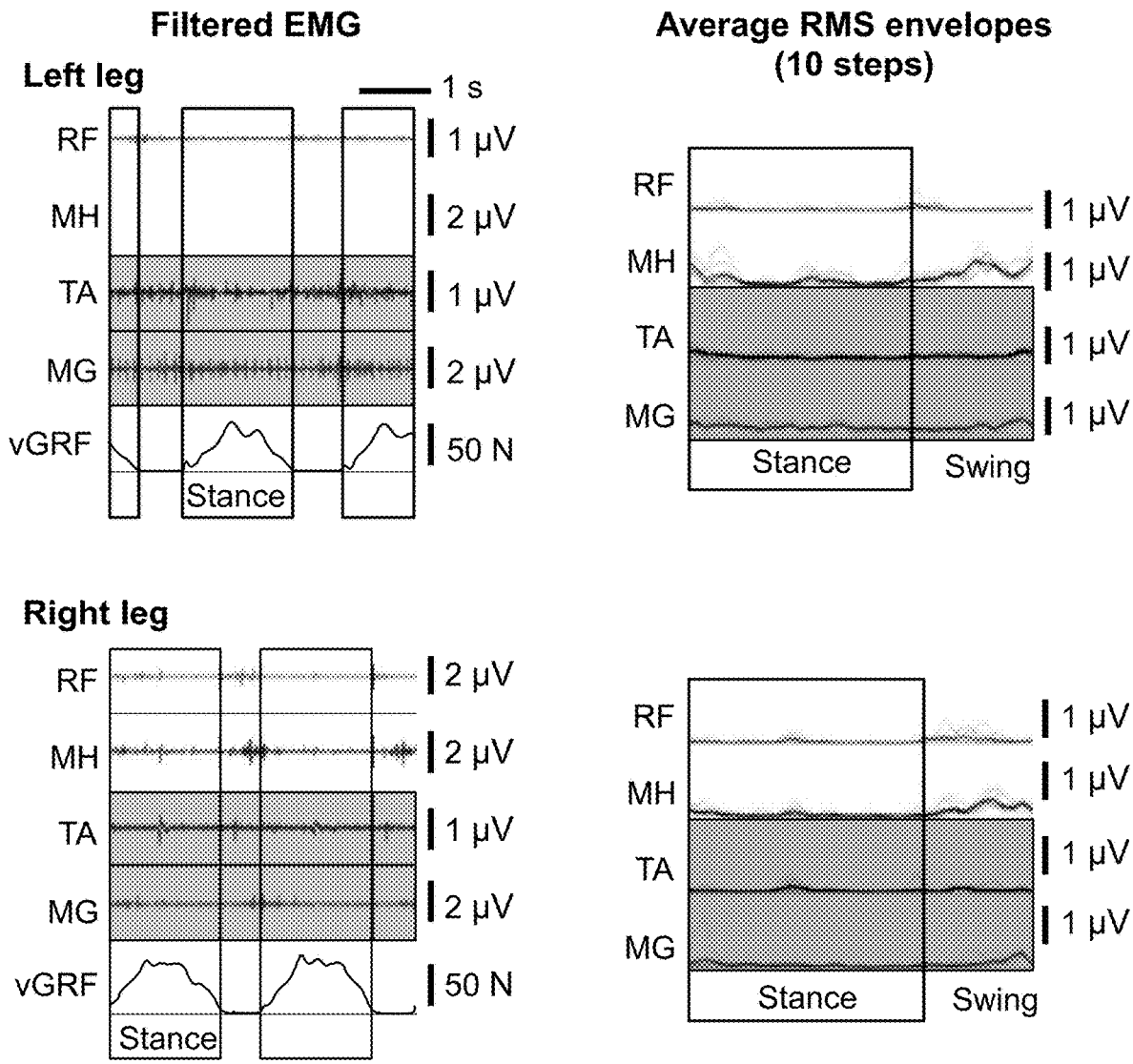
FIGS. 5A-C depict, without EES, leg muscle activity and coordination being lost during walking on a treadmill. Without EES (Panel A), walking on the treadmill at a speed of 0.35 m/s required 30% BWS and full trainer assistance to manipulate the legs in a stepping pattern. Surface EMG synchronized to vGRF indicates uncoordinated low-amplitude muscle activity throughout the step cycle. In the absence of EES, activity across all recorded muscles was significantly lower ($p<0.001$) compared to EES-enabled self-assisted walking (Panel B). Without EES, muscle activation profiles during stance, early swing, and late swing phases showed no significant differences across muscles with respect to each step cycle phase. (Key: EES=epidural electrical stimulation; Hz=Hertz; V=Volts; BWS=body weight support; EMG=electromyography; s=second; RMS=root mean square; µV; =microvolt; vGRF=vertical ground reaction force; N=Newton; RF=rectus femoris; MH=medial hamstring; TA=tibialis anterior; MG=medial gastrocnemius).

Turning EES off during week 43 resulted in an immediate loss of walking ability, requiring BWS and trainer assistance to manipulate the legs in a stepping pattern. Without EES, leg muscle activity (FIG. 5A) was significantly lower in amplitude (FIG. 5B, $p<0.001$) and uncoordinated with respect to step cycle phases (FIG. 5C) when compared to EES-enabled walking.

EES-Enabled Walking Over Ground Using A Front-Wheeled Walker

Week 16 of EES+MMR. At week 16, EES parameters consisted of a single program that was applied in a non-patterned fashion (anode: 8; cathodes: 4,10,15; 0.21 ms; 25 Hz; 6 V) (FIG. 6A). Using these settings, EES enabled walking over ground required the use of a front-wheeled walker and trainer assistance to facilitate swing phase while bracing the contralateral limb to maintain the stance phase and at the hips to facilitate weight shifting and upper body balance (FIG. 6B). RF activation occurred during the stance phase with inhibition during the swing phase, while MH activity was characterized by tonic firing in the left leg throughout the step cycle (FIGS. 6C and 4D). However, MH activity in the right leg was characterized by tonic firing with brief inhibition of activity during the transition from stance to swing inhibition. No statistical differences were found between the RF and MH during the stance phase of both legs (FIG. 6E). However, during the early and late swing phases of both legs, RF activity was significantly inhibited compared to MH ($p<0.001$).

Week 43 of EES+MMR. At week 43, the same interleaved EES program used to enable walking on the treadmill was used to walk over ground using a front-wheeled walker and intermittent trainer assistance to facilitate weight shifting and to maintain balance (FIGS. 6F and 4G). For both legs, RF activity was characterized by bursts of activation during the stance phase followed by inhibition during the early swing phase (FIGS. 6H and 4I). Tonic activity of the MH was observed during stance followed by bursts of activation during swing phase. Normalized muscle activity of the left and right leg showed no significant difference in activity between RF and MH during the stance phase (FIG. 6J). However, significantly higher activation of the MH while the RF was inhibited ($p<0.001$) occurred during the early swing phase of both legs. During the late swing phase, activation profiles demonstrated a significant increase in RF activity compared to MH (Left leg=$p<0.05$, Right leg=$p<0.001$). In summary, and similar to self-assisted walking on the treadmill, the use of two interleaved EES programs appeared to enable significant changes in muscle activity profiles during the late swing phase that coincided with the ability to walk over ground with minimal assistance, compared to using a single EES program at week 4.

Figures 7A, 7B:
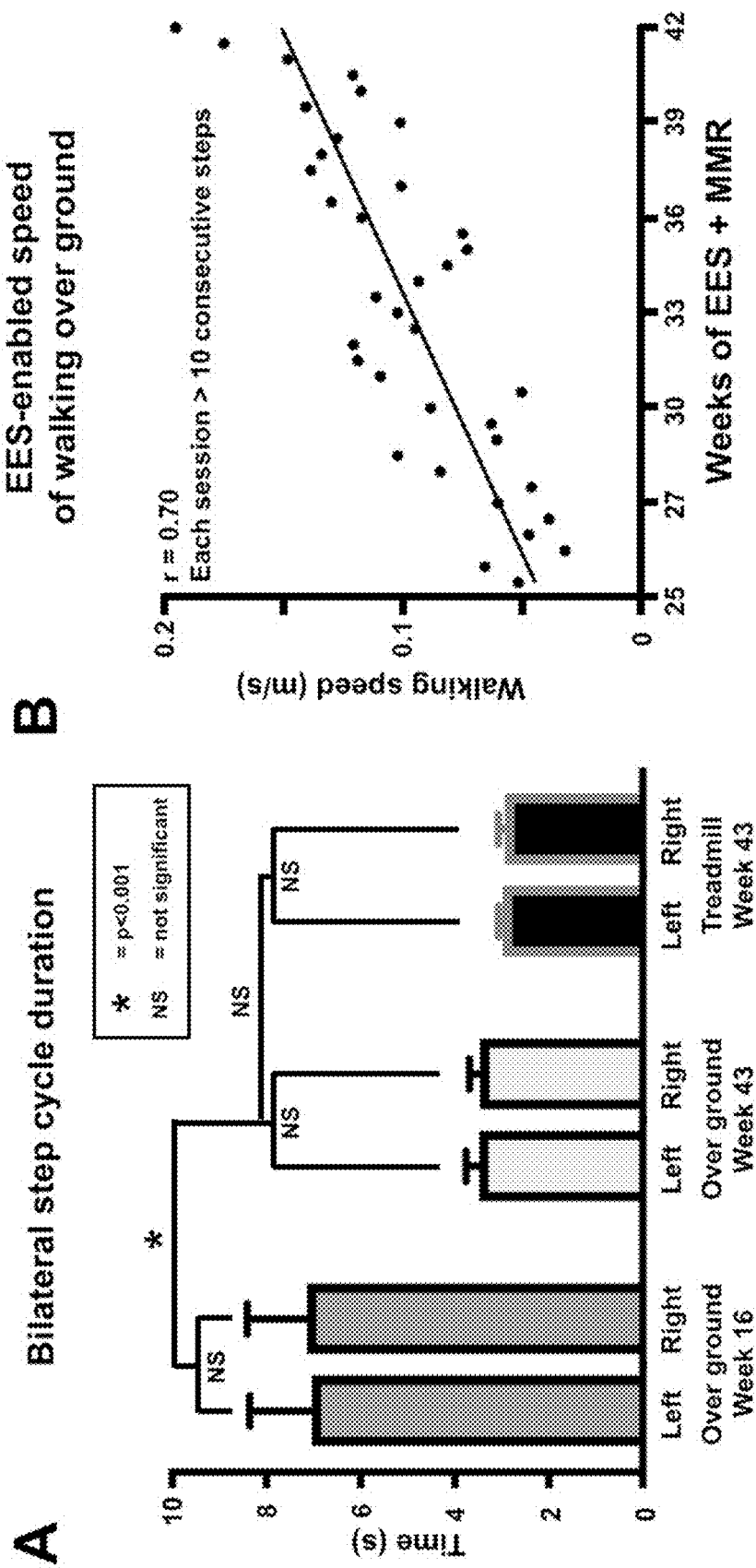
FIGS. 7A-B depict plots showing step-cycle characteristics during EES-enabled walking activities. Step cycle durations during 10 steps of the left and right leg (20 steps total) are compared at week 16 and week 43 of walking over ground and at week 43 self-assisted walking on a treadmill (Panel A). Panel B shows the progression of over ground walking speed from week 25 to 42 using two interleaved EES programs at all time points. During each over ground walking session, voltage intensities were adjusted in 0.1 V increments from 3-5 V within each program to balance the subject's bilateral control of walking. (Key: m/s=meter per second; r=correlation coefficient; EES=epidural electrical stimulation; Hz=Hertz; V=volts; NS=not significant).
Figures 8A, 8B:
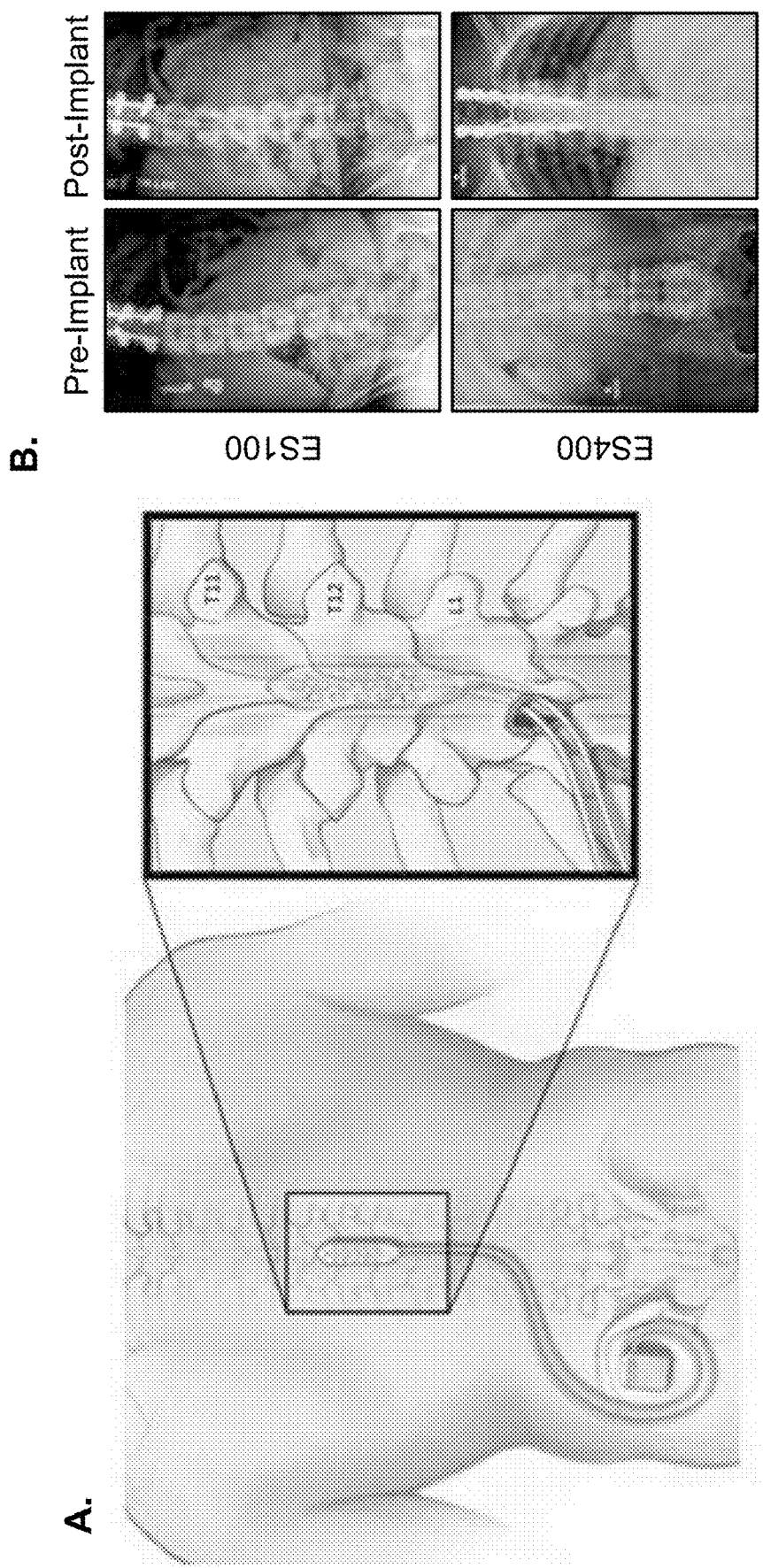
FIGS. 8A-8B show images depicting surgical implantation of an EES array.

EES-Enabled Step Cycle Characteristics. Step cycle durations between the left and right leg were not significantly different during week 16 and 43 of walking over ground, as well as during week 43 of self-assisted walking on the treadmill (FIG. 7A). However, bilateral step cycle durations from week 16 to week 43 of walking over ground decreased significantly (p<0.001), which resulted in treadmill and over ground step cycle durations that were not significantly different by week 43.

Electrode configurations and stimulation frequencies of the interleaved EES program were held constant for all over ground walking sessions from week 25 to 42. During these sessions, trainers focused on minimizing the amount of assistance provided. EES-enabled walking speed improved from 0.05 m/s at week 25 to 0.20 m/s at week 42 (FIG. 7B). The maximum number of steps taken during a single EES+MMR session was 331 and the maximum distance traveled was 102 meters. A front-wheeled walker was used for all sessions.

Discussion

Over the course of 43 weeks, EES+MMR enabled a human with complete paraplegia to walk self-assisted on a treadmill. Additionally, walking over ground was achieved in the presence of EES while using a front-wheeled walker and intermittent trainer assistance. For both treadmill and over ground walking, the use of two interleaved EES programs enabled a significant change in muscle activity profiles during the swing phase of the step cycle. This shift in coordination coincided with an ability to walk self-assisted on the treadmill and with minimal trainer assistance over ground. These results, combined with prior evidence of enabling motor control via EES following motor complete SCI emphasize the need to reassess current understanding of the biological underpinnings of complete SCI and how spinal neuromodulation with MMR progressively enables functions that were once thought to be permanently lost following SCI. See, e.g., Rejc E, Angeli C, Harkema S. Effects of Lumbosacral Spinal Cord Epidural Stimulation for Standing after Chronic Complete Paralysis in Humans. PLoS ONE 2015; 10(7):e0133998-20; Rejc E, Angeli C A, Bryant N, Harkema S J. Effects of Stand and Step Training with Epidural Stimulation on Motor Function for Standing in Chronic Complete Paraplegics. Journal of Neurotrauma 2017; 34(9):1787-802; Gerasimenko Y, et al. Noninvasive Reactivation of Motor Descending Control after Paralysis. Journal of Neurotrauma 2015; 32(24):1968-80; Lu D C, Edgerton V R, Modaber M, et al. Engaging Cervical Spinal Cord Networks to Reenable Volitional Control of Hand Function in Tetraplegic Patients. Neurorehabilitation and Neural Repair 2016; 30(10):951-62; Gad P, Gerasimenko Y, Zdunowski S, et al. Weight Bearing Over-ground Stepping in an Exoskeleton with Non-invasive Spinal Cord Neuromodulation after Motor Complete Paraplegia. Front Neurosci 2017; 11:1394-8.

The interleaved EES paradigm identified in this study played a role in enabling walking abilities. However, the MMR paradigm used in concert with EES may also play a role in re-educating spinal neural networks associated with locomotor activities. For example, during EES+MMR, the subject was encouraged to use his arms on support bars to manipulate his body during EES-enabled walking. In addition, trainer assistance, BWS, and the speed of treadmill and over ground walking were adjusted as EES-enabled walking performance improved in order to maximize independence.

Facilitating spinal neural networks, via interleaved EES with MMR, generated coordinated motor activity that was controlled by the subject to achieve walking activities. It is possible that new neural connections were formed across the lesion during EES+MMR. However, when EES was turned off, the subject's paralysis remained the same over the course of the study, suggesting that any new connections that arose remained subfunctional. Therefore, combined with prior evidence (see, e.g., Angeli C A, Edgerton V R, Gerasimenko Y P, Harkema S J. Altering spinal cord excitability enables voluntary movements after chronic complete paralysis in humans. Brain 2014; 137(5):1394-409; Harkema S J, Gerasimenko Y P, Hodes J, et al. Effect of epidural stimulation of the lumbosacral spinal cord on voluntary movement, standing, and assisted stepping after motor complete paraplegia: a case study. The Lancet 2011; 377(9781):1938-47; Grahn P J, Lavrov I A, Sayenko D G, et al. Enabling Task-Specific Volitional Motor Functions via Spinal Cord Neuromodulation in a Human With Paraplegia. Mayo Clinic Proceedings 2017; 92(4):544-54; Gerasimenko Y, et al. Noninvasive Reactivation of Motor Descending Control after Paralysis. Journal of Neurotrauma 2015; 32(24):1968-80; Lu D C, Edgerton V R, Modaber M, et al. Engaging Cervical Spinal Cord Networks to Reenable Volitional Control of Hand Function in Tetraplegic Patients. Neurorehabilitation and Neural Repair 2016; 30(10):951-62; Gad P, Gerasimenko Y, Zdunowski S, et al. Weight Bearing Over-ground Stepping in an Exoskeleton with Non-invasive Spinal Cord Neuromodulation after Motor Complete Paraplegia. Front Neurosci 2017; 11:1394-8), the findings in the instant study that is the subject of this example implementation support the concept that electrical facilitation of spinal neural networks enables supraspinal control of motor activities by modulating the excitability of spared connections across the injury that were functionally silenced during SCI.

Example Implementation #2

Introduction

Severe, traumatic injury of the spine can result in fracture and dislocation of spine structures that in turn can lead to acute and chronic disruption of spinal cord tissues. This example implementation explores treatment options for volitional control over spinal cord injury (SCI)-induced motor function deficits such as standing or walking.

The study that is the subject of this example describes, among other things, 1) the surgical approach to implant the epidural electrical stimulation system and 2) the intraoperative and post-operative electrophysiological monitoring of electrically evoked motor potentials which both guided placement in the operating room, and confirmed stimulator positioning post-operatively.

Methods

This study was performed under the approval of the Mayo Clinic Institutional Review Board with a U.S. Food and Drug Administration Investigational Device Exemption (IDE G150167, NCT02592668).

Subjects. Two individuals with motor and sensory complete (ASIA-A) SCI were recruited for this study.

Device Specifics. The EES system in this study included a 16-contact epidural electrode array (SPECIFY 5-6-6, MEDTRONIC, Fridley, MN) and implantable pulse generator (RESTORE-SENSOR SURE-SCAN MRI, MEDTRONIC, Fridley, MN).

Operative Procedure. Placement of the epidural electrode was accomplished via a laminectomy from T12-L1. Following anesthesia induction, placement of IV lines and a Foley catheter, patients were positioned prone on a Jackson surgical table with head fixation in a Mayfield clamp. A midline incision was planned based on appropriate anatomical landmarks and confirmed with a pre-operative radiograph. A midline incision was performed with a sharp knife and carried down through the lumbodorsal fascia to the level of the spinous process in an avascular plane using Bovie electrocautery. The correct spinal level is confirmed intraoperatively by placement of a perforating towel clip on the spinous process and obtaining a localization plain film x-ray. Once the appropriate level is confirmed, subperiosteal dissection of the muscle from the spinous process down to the lamina and then laterally toward the facets was performed. The T11-12 and L1-2 interspinous ligaments are severed and the spinous processes of T12 and L1 are removed with an Adson rongeur. The laminae are then thinned with a 4-mm diamond drill bit and removed with Kerrison rongeurs. The ligamentum flavum is dissected free from the underlying dura.

The EES electrode array is then placed directly on the dura of the T12-L1. The electrodes were carefully inspected to ensure full contact with the dura and the leads are secured to the paraspinal muscles. Intraoperative fluoroscopy is utilized to ensure and document appropriate electrode placement. The leads are then tunneled subcutaneously toward the right upper abdomen where a small subcutaneous pocket is made to house the lead wires. After meticulous hemostasis and irrigation with a bacitracin solution, the wounds are closed in anatomical layers. The patient is then disconnected from the Mayfield headframe removed from the Jackson table onto a stretcher. The pocket housing the lead wires is then reopened and the neurostimulator attached and secured to the underlying soft tissue. The wound is then irrigated and closed in anatomic layers as before.

Intraoperative Electrophysiology. To guide placement of the epidural electrode, electrophysiology was performed intraoperatively by stimulating the spinal cord at multiple configurations and monitoring electrically evoked motor potentials via intramuscular electromyography (EMG) recorded from six lower leg muscles, bilaterally: Rectus Femoris (RF), Vastus Lateralis (VL), Medial Hamstring (MH), Tibialis Anterior (TA), Medial Gastrocnemius (MG), and Soleus (SOL). Additionally, an EMG electrode was implanted paraspinally in order to record a stimulation artifact. Stimulation was performed at 0.5-1 Hz with a 210 µs pulse width. Voltages were incrementally increased to establish recruitment curves for each subject.

Post-Operative Electrophysiology. To assess how translatable the results obtained intraoperatively were to the results obtained after surgery, the subjects were stimulated using identical configurations and voltages after three weeks of surgical recovery. Identical muscles were analyzed using surface EMG as during the intraoperative procedure. Subjects lied supine on a mat while stimulation was performed in order to evaluate EMG responses.

Results

Intraoperative Testing To Locate Optimal Position. After insertion of the electrode array between T11 and L1 under intraoperative fluoroscopic guidance, evoked potentials were generated and monitored from leg muscle in order to determine array position with respect to lumbosacral spinal circuitry. As shown in FIG. 9, rostral and caudal configurations were used in both subjects to evoke motor potentials. In the rostral configurations, mainly proximal muscle activity was achieved, with little activity in distal muscles. Similarly, caudal configurations stimulated distal muscles with little proximal muscle activation. Furthermore, in ES400 the electrode array was activated on the left and right sides following closing of the surgical incision. Activation of left and right muscles were observed with the respective ipsilateral electrode configuration. The contralateral muscles were not activated.

In addition to motor pool specific placement of the contacts of the electrode, real-time electrophysiology guided manipulation of the array by the surgeon on order to position it over the L2-S1 spinal segments in a symmetrical fashion with respect to e-phys/not just imaging. As shown in FIG. 10, a midline caudal configuration was used to stimulate for distal muscle activation. However, as shown in FIG. 10A, this did not cause consistent activation of the left, distal muscles. Therefore, the electrode was shifted slightly leftwards. Following this movement, a more symmetric activation pattern was achieved as shown in FIG. 10B.

Figure 11:
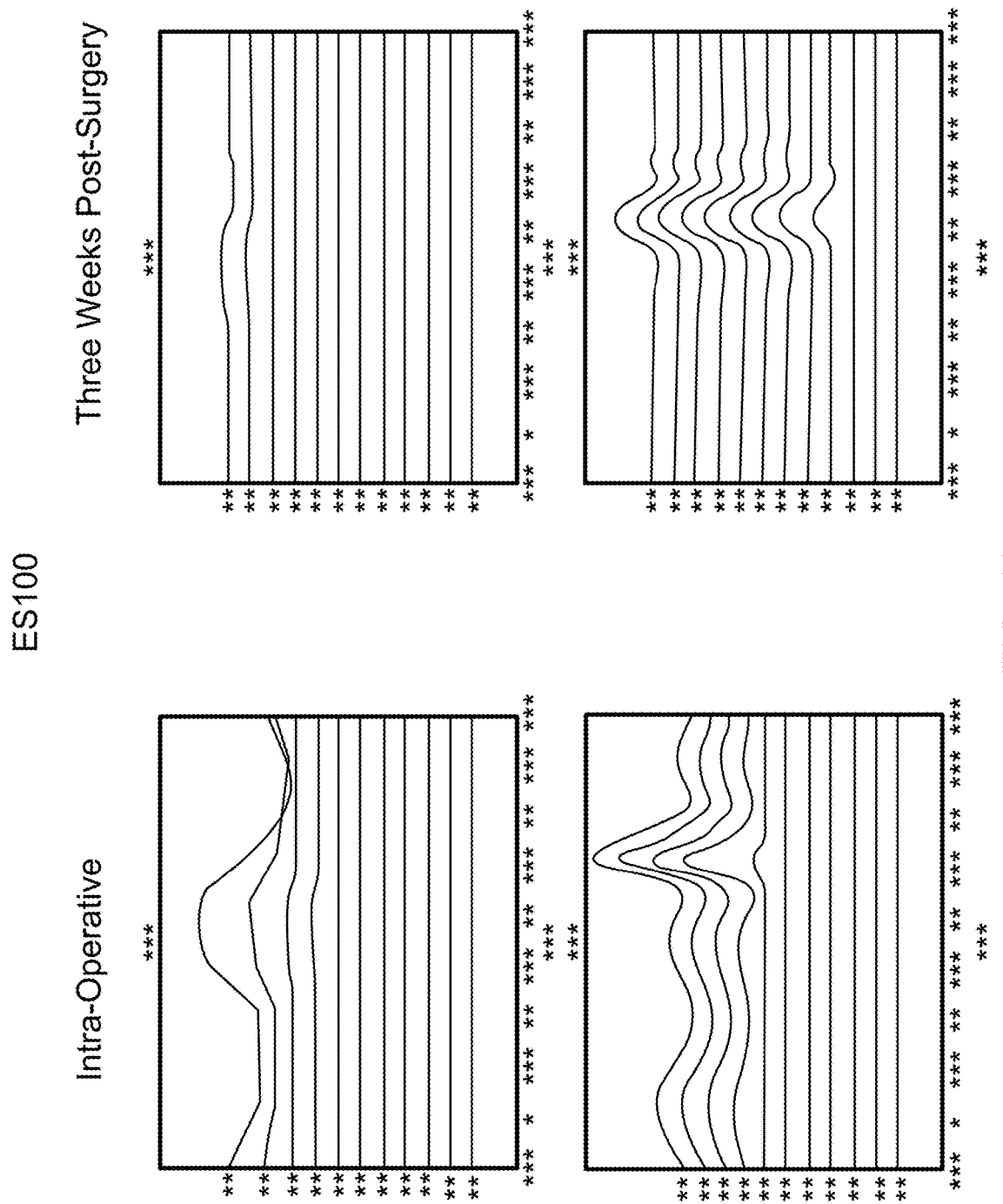
FIG. 11 depicts plots of intraoperative electrophysiology to predict post-operative electrophysiology results. EMG (Electromyography) data from both subjects recorded intraoperatively and after three weeks of recovery from surgery. Each line represents the average of at least five stimulations recorded at increasing voltages. Data is recorded from the left RF (rectus Femoris) and left MG (medial gastrocnemius). Identical configurations were used across all trials (+5/−10, 210 μs pulse width, 1 Hz.).
Figure 11:
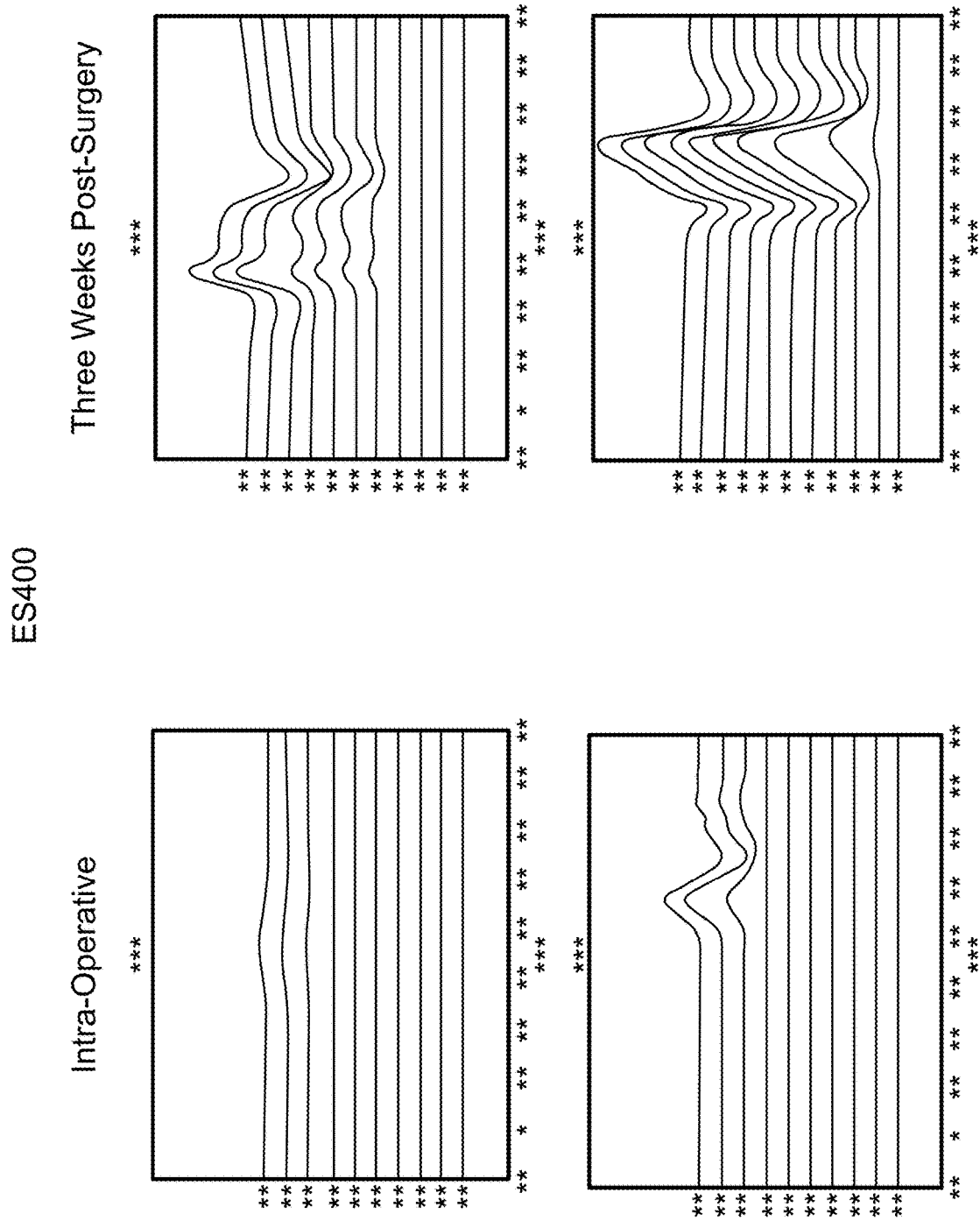

Comparison Between Intraoperative And Post-Operative Electrophysiology. Both subjects were stimulated with the same configurations intraoperatively and following three weeks of surgical recovery. In FIG. 11, a +5/−10 configuration is used to stimulate the spinal cord in both subjects to create the recruitment curves. As shown in FIG. 11, motor responses were achieved intraoperatively in proximal and distal muscles. These responses had similar pattern, but were achieved at lower stimulation thresholds when performed post-operatively.

The characteristics of the responses across all muscles were analyzed as shown in FIG. 12. Using the same +5/−10 caudal configuration as in FIG. 11, the voltage was incrementally increased in a stepwise fashion. In both subjects, intraoperatively and postoperatively, all muscles were active at maximum voltage as shown in FIG. 12A. Furthermore, muscles were recruited in a physiological fashion, with distal muscles recruited prior to proximal muscles. Similar to FIG. 11, all muscles show lower recruitment threshold post-operatively. ES400 displayed high activation thresholds intraoperatively, however post-operative voltages were similar to ES100. Additionally, as shown in FIG. 12B, latencies of activation were similar across subjects and testing conditions within muscles.

Discussion

The description of the study that is the subject of this example implementation discusses the surgical procedure in detail. The surgical procedure described herein includes important differences from EES surgical procedures used for chronic pain management. However, there are many nuances to the surgery which should be carefully considered in order to lead to optimal results. Additionally, many neurophysiology researchers interested in translating their results to a clinical trial using EES may be unfamiliar with the surgical procedure required in order to achieve an excellent outcome. This description provides a framework from which to guide future clinical trials using EES for a variety of functional improvements following SCI.

Intraoperative electrophysiologic monitoring allows for real-time assessment of the nervous system during surgery. Here, we demonstrate the utility of intraoperative monitoring to predict beneficial outcomes for subjects undergoing EES procedures instead of monitoring for adverse events during surgery.

Recording intraoperative electrophysiological data allowed for precise placement of the epidural electrode. By applying stimuli at multiple different regions of the spinal cord using differing configurations, optimal electrode location could be identified in both the rostral-caudal and medial-lateral directions. In the case of the second subject, the electrode was determined to be off-set slightly to the right as shown in FIG. 10 where a symmetric configuration led to activation of only the right leg muscles. This was detected and quantified by the intraoperative recording equipment, and required only a small movement by the neurosurgeon. However, this position change was critical in activating desired motor pools that would lead to optimal benefit to the patient.

In addition to providing real-time monitoring of the electrophysiological responses during surgery, intraoperative monitoring predicts responses and optimal configurations to be used in evoking muscle activity post-operatively as shown in FIGS. 4 and 5. Responses happened at lower amplitudes of stimulation post-operatively, but the intraoperative responses predicted that responses would occur when stimulated at distinct regions of the spinal cord. The lower threshold of responses could be caused by a number of reasons including: prone vs. supine positioning, intramuscular vs. surface EMG, or enclosure of the EES electrode within the epidural space following closure of the surgical incision. However as shown in FIGS. 4 and 5, these intraoperative responses were similar in characteristics to those seen post-operatively. Therefore, the intraoperative recordings were key in identifying correct location of the EES device and allowing for real-time analysis of electrophysiology within the operating room.

Example Implementation #3

In this example, a study was performed analyzing the neuroanatomy of the swine lumbar spinal cord. The spatial orientation of dorsal rootlet projections was correlated to the anatomical landmarks of the lumbar spine and to the magnitude of motor evoked potentials during epidural electrical stimulation (EES). It was found that the proximity of the stimulating electrode to the dorsal rootlet projections across spinal segments was a critical factor to evoke higher peak-to-peak motor responses. Positioning the electrode close to the dorsal roots produced a significantly higher impact on motor evoked responses than rostro-caudal shift of electrode from segment to segment. Based on anatomical measurements of the lumbar spine and spinal cord, significant differences were found between L1-L4 to L5-L6 segments in terms of spinal cord gross anatomy, dorsal roots and spine landmarks. Linear regression analysis between intersegmental landmarks was performed and L2 intervertebral spinous process length was selected as the anatomical reference in order to correlate vertebral landmarks (i.e., vertebral features) and the spinal cord structures. These findings present for the first time, the influence of spinal cord anatomy on the effects of epidural stimulation and the role of specific orientation of electrodes on the dorsal surface of the dura mater in relation to the dorsal roots. These results are critical to consider as spinal cord neuromodulation strategies continue to evolve and novel spinal interfaces translate into clinical practice.

Epidural electrical stimulation (EES) of the spinal cord has emerged as a promising therapy for enabling motor function, respiratory muscle activation and bladder control following spinal cord injury (SCI). Several known factors can influence the effect of EES, such as spatial orientation of dorsal spinal cord structures, electrical properties of intraspinal elements, nerve fibers activated, presence of ipsi- and/or contralateral afferents and the timing of stimulation pulses in relation to the intended motor activity. Although the dorsal roots and dorsal ascending spinal columns are considered the main target of EES, the precise mechanisms underlying the effect of EES on these spinal neural structures remain unclear. Initial computational modeling of EES suggest that activation threshold depends on the orientation of electrical field along the target fibers, specifically the curvature of the dorsal root anatomy and the angles between the dorsal fibers and the spinal cord axis. More recent computer simulations further define that thick dorsal root fibers are recruited at the lowest EES intensities and particularly that Group Ia/Ib and Group II afferents are the first neural elements to be depolarized. In vivo experiments in rodent models have shown that high-intensity EES leads to activation of ventral spinal neural structures that in turn produce an early response (ER) with latencies of 3-5 ms at recording sites with active muscles. At lower EES intensities, activation of dorsal spinal structures produces a middle response (MR) in muscles with latencies between 5-9 ms. The difference in timing of these two responses is likely due to an intraspinal synaptic relays from dorsal root structures to ventral horn and ventral roots.

Computational modeling and rodent studies have shed some light on the mechanisms by which EES enables motor function after SCI. However, small animal models, such as the rodent, are not optimal for studying these structures due to significant difference in spinal cord anatomy between human and rodent spinal cord anatomy. Large animals including calf, sheep, and swine, have been successfully used as translational models. Particularly, the swine spine has gained attention as a suitable model due to its similarity to humans in terms of vertebral morphometry and biomechanical properties; however, a description of the swine spinal cord anatomy and its intersegmental relationship with the spine is missing. In this study, the swine model was chosen due to its translational relevance and its emergence as an optimal model to study EES following SCI.

The primary goal of this investigation was to evaluate the role of spinal cord neuroanatomy in effect of EES and how spinal circuitry may inform the optimal electrode positioning in relation to spinal cord dorsal structures. More specifically, this study: (1) described the gross anatomy of the swine lumbar spinal cord and the spatial orientation of dorsal spinal cord roots, rootlets (root fibers), and dorsal rootlet projections; (2) identified anatomical landmarks of the spine and spinal cord to correlate bony landmarks to spinal cord segments; and (3) determined the role of dorsal spinal cord Neuroanatomy in EES motor evoked responses.

Materials and Methods

Subjects

All study procedures were conducted with the approval of the Mayo Clinic Institutional Animal Care and Use Committee and in accordance with the National Institutes of Health Guidelines for Animal Research (Guide for the Care and Use of Laboratory Animals). 11 domestic white swine males aged 8-12 weeks and weighing 25-40 Kg were used for this study. Animals were kept in separate cages in a controlled environment (constant temperature at 21° C. and humidity at 45%) on a 12-hour light/dark cycle with ad libitum access to water, and were fed once daily.

Post-Mortem Spine Dissection and Anatomical Measurements

The lumbosacral spine was extracted en bloc from each subject for dissection. Once extracted, landmarks were established along the facet joints, transverse processes, as well as anterior and posterior portions of the vertebral laminae as indicated on FIG. 13A. The distances between these landmarks included: a) intervertebral length; b) midvertebrae foramen length (right and left); c) intervertebral spinous process length and d) vertebral bone length (left and right). Anatomical bone landmarks (features) were measured manually using slide calipers. A laminectomy was then performed across all lumbosacral vertebrae to expose the spinal cord. The dura was incised to expose the spinal cord, and anatomical landmarks were determined across lumbar segments as illustrated in FIG. 13A and measured with slide calipers as follows: a) transverse diameter at the dorsal root entry with reference at three locations: rostral, middle and caudal; b) spinal cord segment length, from the caudal extent of a segment's rootlet entry zone to the caudal extent of the next segment's rootlet entry zone; c) segment width at dorsal root entry zone and d) distance from midvertebrae foramen to dorsal rootlet entry. Together, these parameters characterize the size of the dorsal rootlet projections. Next, high resolution pictures of each segment were taken with a surgical microscope (LEICA M20, 4× objective) after which measurements were taken of the spatial orientation of the dorsal roots and rootlets (FIG. 14A,B) using GEOGEBRA open source software (www.geogebra.org). Lumbar dorsal root and rootlets projections analysis included: a) number of dorsal rootlets; b) root width from bone; c) rostral and caudal roots angles; d) rostral and caudal rootlet length from bone; e) width across dorsal columns and f) rostral root to caudal root length.

EES Procedure

Two animals underwent in vivo electrophysiological experiments consisting of recording spinally evoked motor responses from select hind limb muscles during EES. Intramuscular telazol (5 mg/kg) and xylazine (2 mg/kg) were administered for anesthesia induction and 1.5-3% isoflurane for maintenance. Fentanyl was continuously administered during surgery (2-5 mg/kg/hr) for analgesia. Briefly, laminectomies were performed to expose the lumbosacral spinal cord (L1-S1). Connective and fat tissue was removed keeping the dura mater intact. For EES, two types of electrodes were used: Subject 1 was tested with a single contact, custom-made spherical stainless steel electrode (2.5 mm diameter) and Subject 2 with an 8-contact stainless steel rod array (1.3 mm diameter, 3 mm contact length, 4 mm spacing between contacts) (Model 3874, MEDTRONIC, MN). The spherical electrode was sequentially placed over the dorsal roots entry zones at L1, L2 and L3 segments as well as distally locations to the dorsal roots in intersegmental positions (L1-L2, L2-L3 and L3-L4) (FIG. 18A). This approach allowed the electrode to be manipulated with ease in relationship to the dorsal spinal cord anatomy (i.e. dorsal rootlets). To study caudal segments, the rod array that was placed on the midline spanning L4-L6 segments to cover most of the dorsal rootlets in that region was used, which are denser compared to the rostral segments, and therefore, an intersegmental distance between them cannot be identified (FIG. 14A). A reference electrode was inserted in the paravertebral muscles on the right side of the surgical site. An isolated pulse generator (A-M SYSTEMS, Sequim, WA) delivered biphasic square wave pulses (500 μs pulse width) at 0.5 Hz with amplitudes ranging from 0.25-4.5 mA.

Electrophysiological Recordings

To record spinally evoked motor responses, muscles of the hind limbs were dissected bilaterally and a pair of two stainless steel wires (AS 631, Cooner wire) were placed intramuscularly to capture electromyography (EMG) from the following muscles: gluteus maximus (GLU); rectus femoris (RF); vastus lateralis (VL); tibialis anterior (TA); soleus (SOL); and medial gastrocnemius (MG). Signals were amplified (BIO AMPLIFIER AD Instruments, Colorado Springs, CO) and digitized (sampled at 4 KHz, hi-pass 0.5 Hz) using a POWERLAB acquisition system (AD INSTRUMENTS, Colorado Springs, CO). Offline, the recorded responses were band-pass filtered (20-500 Hz, Butterworth) in MATLAB (The MATHWORKS Inc., Natick, MA). To determine the onset and amplitude of each response, waveforms were analyzed and compared starting from the voltage threshold that elicited the onset of early (ER) and middle (MR) responses and continuing as stimulation intensity was incrementally increased in 0.25 mA steps. Peak-to-peak response amplitudes and latencies were measured in a window of 5 to 25 ms from stimulation artifact using a custom MATLAB script. ER peak-to-peak amplitude was determined on the positive slope of the waveform and on the negative slope for MR. Examples of the peak-to-peak amplitude and latency measurements are depicted in the bottom traces of FIG. 17A. If evoked responses were not distinguishable, latencies and amplitudes were measured at the first and second peaks in the same time window.

Data Analysis

SIGMAPLOT (SYSTAT SOFTWARE, San Jose, CA) was used to perform statistical analysis. The Shapiro-Wilk method was used to determine if the data were normally distributed. If so, an Equal Variance Test was performed using the Brown-Forsythe method. Significant differences were determined by one-way repeated-measures analysis of variance (ANOVA). Pairwise multiple comparisons (Holm-Sidak) were performed to determine statistically significant differences between lumbar segments. Data that were not normally distributed were analyzed using Tukey test and pairwise multiple comparisons were done using Dunn's method. Nine of the eleven swine used for this study were acquired post-mortem following unrelated experimental studies in which the spinal column and cord remained intact. The relationship between intersegmental measurements of the spine and spinal cord across lumbar segments was determined via linear regression. The following spine variables (vertebral features) were correlated with the spinal cord segments lengths: intervertebral spinous processes, vertebral bone length and midvertebrae foramen lengths. Then, the highest correlation coefficient was used to determine a proper a) intersegmental vertebrae landmark (vertebral feature) and b) spine segment, and to use them as a reference to establish ratios between spine and spinal cord across segments. The means of the intersegmental landmark lengths (spine and spinal cord) were used to obtain the ratios. Once identified the proper intersegmental landmark and spinal segment (expressed as 100%, ±SD), a diagram illustrating the relationship between the spine and the spinal cord was performed. For this purpose, the length's values of the intersegmental landmark and spinal cord were expressed as percentage (±SD) in relation to the spinal segment used as reference.

Figure 18:
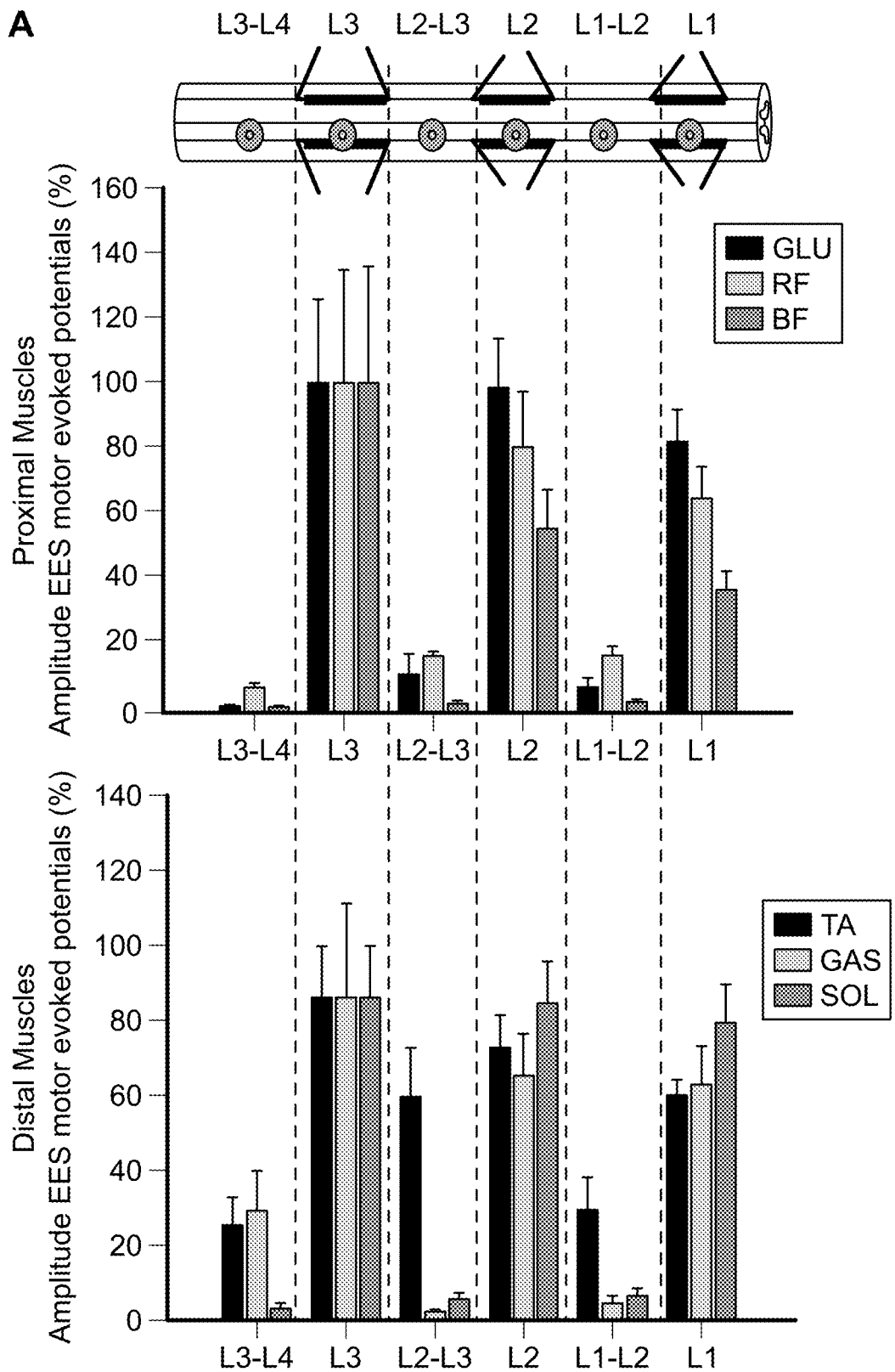
FIG. 18 depicts motor responses during EES at L1-L3/L4. (A) Upper panel shows the electrode positions (single spherical electrode) over dorsal root entries zones (at L1, L2 and L3) and between segments (at L1-L2, L2-L3 and L3-L4) in subject 1. Amplitude of the motor evoked potentials is expressed as % (±SEM). Responses were recorded in proximal (upper plot) and distal muscles (bottom plot). (B) Representative averaged traces of motor potentials (gray rectangles, 10 ms time window) evoked at 1.4 mA. Each trace represents the average of ten motor responses. The electrode was placed on dorsal roots (L3, left traces) and between segments (L3-L4, right traces). Mean latencies (±SD) of the first (red bar) and second peak (black bar) are shown below the traces on left for each muscle.
Figure 18:
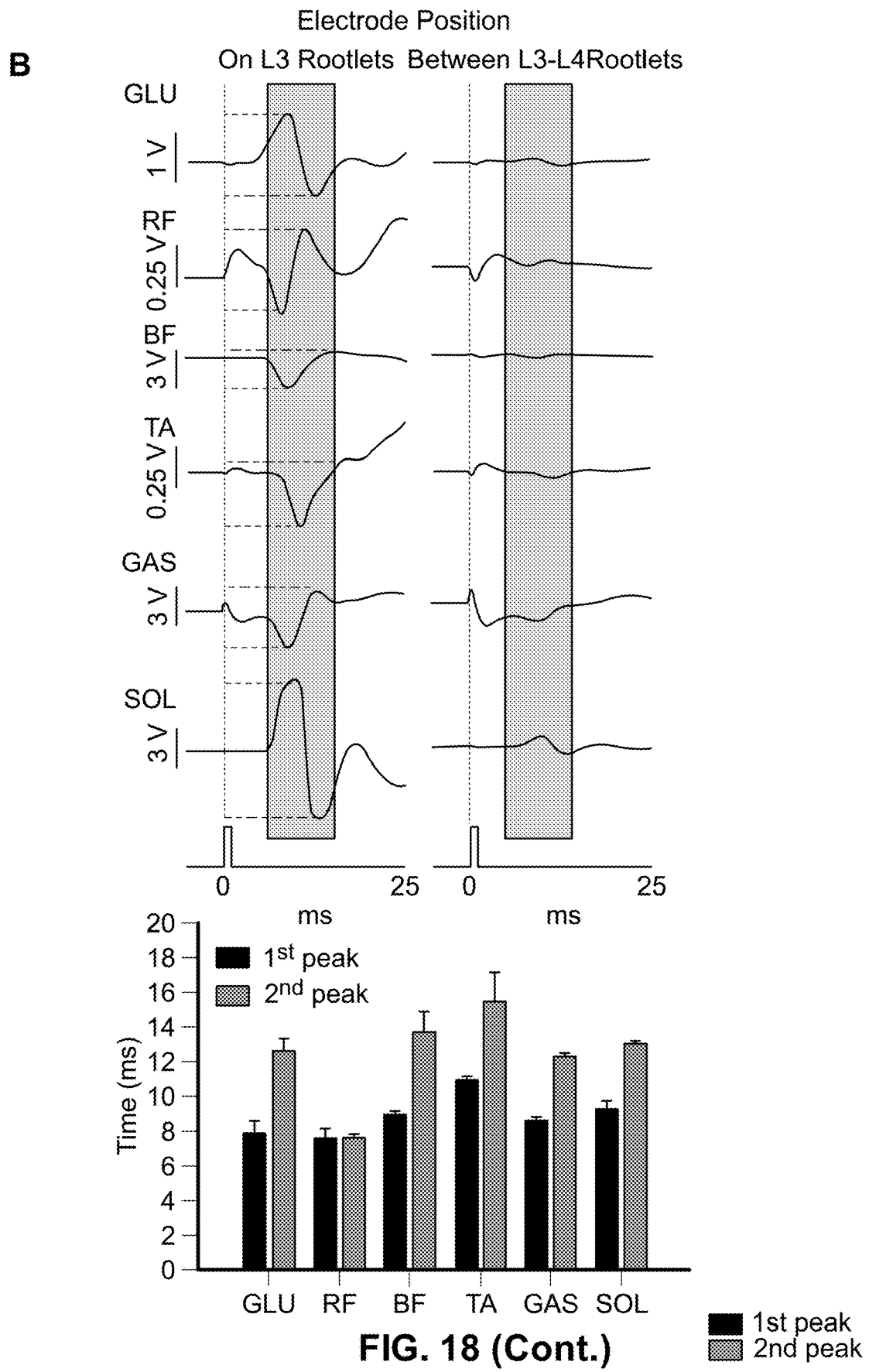
Figure 19:
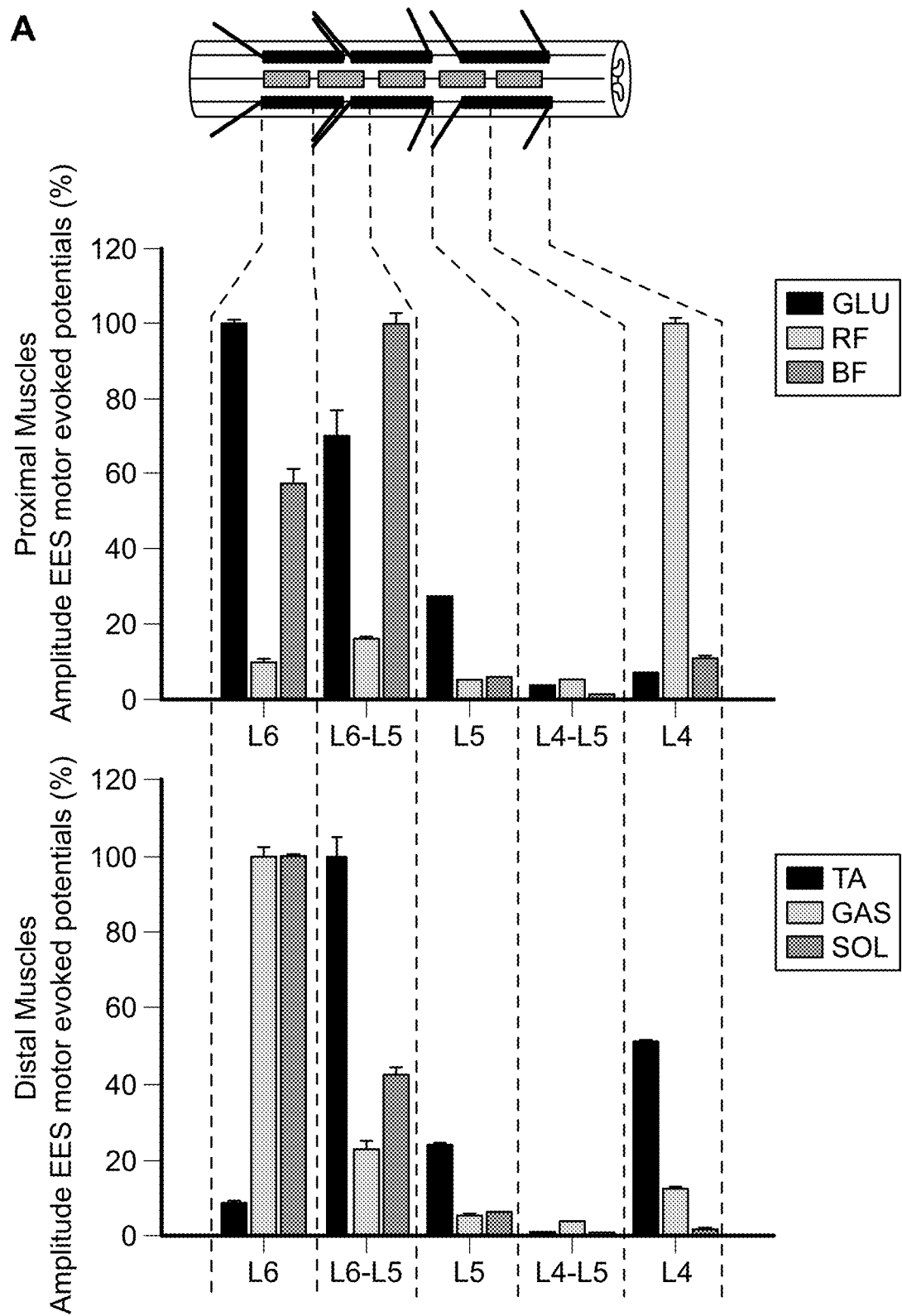
FIG. 19 depicts motor responses during EES at L4-L6. (A) The multi-array rod electrode (8-contacts rod array, Model 3874, Medtronic, MN) was placed on the midline of the spinal cord at the dorsal rootlets entry levels (L4, L5 and L6) and in approximate locations between the segments (L4-L5 and L5-L6) in subject 2. Gray rectangles in the upper diagram represent the relative position of the multi-array rod electrode. Amplitude of the motor evoked responses is expressed as % (±SEM). Responses were recorded in proximal (upper plot) and distal muscles (bottom plot). (B) Representative averaged traces of motor responses (gray rectangles, 10 ms time window) evoked at 1.4 mA. The electrode was located proximal to L6 dorsal root entry zone (left traces) and in the intersegmental location L4-L5 (right traces). EMG's of distal and proximal muscles were recorded. Each trace represents the average of ten motor responses. Mean latencies (±SD) of the first (red bar) and second peak (black bar) are shown below traces on left for each muscle.
Figure 19:
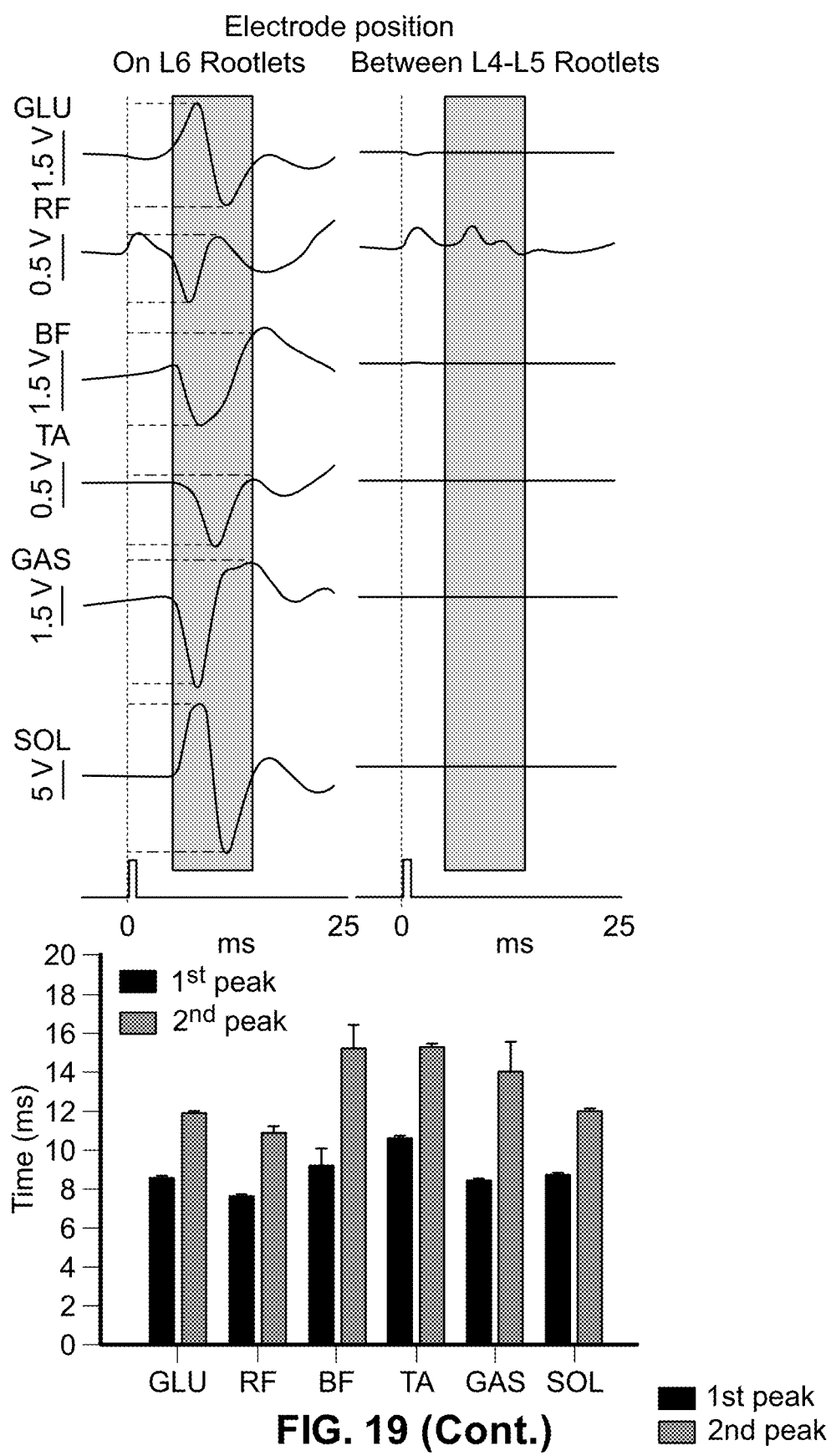

Electrophysiological data (n=2 male swine) were analyzed as follows: ten evoked responses were averaged for each stimulation trial and the highest amplitude values across lumbar segments were expressed as 100% for each muscle. Then, the rest of the amplitudes were expressed as % (±SEM) of the maximal value. Data sets were analyzed separately for each electrode used: spherical in L1-L3/L4 (FIG. 18) and 8-contacts rod array in L4-L6 (FIG. 19).

Results

Lumbar Spinal Cord Gross Anatomy

Lumbar spinal cord gross anatomical landmarks (i.e., spinal cord features) including transverse diameter, segment length, segment length at dorsal root entry and midvertebrae foramen to rootlets distance are illustrated in FIG. 13A. Data (mean, ±SD) from these anatomical measurements are summarized in Table 1 (all tables shown at the end of the results section). Because no statistical differences were found between the three measured transverse diameters at dorsal root entry with respect to rostral, middle or caudal reference points (data not shown), they were averaged into a single diameter measurement per segment. Spinal cord transverse diameter was similar from L1 to L3, but increased at more caudal segments L4-L6, with longer diameter at L5 in 8/9 subjects (FIG. 13B, Table 1). In fact, the transverse diameter from L4 to L6 was significantly higher than L1, as well as L5 compared to L2 (Table 2). The length of the spinal cord segments was similar from L1 to L3, and then gradually decreased from L4 to L6 (FIG. 13C), with the L5 and L6 segments being significantly shorter than the L1-L4. Moreover, L6 was also significantly shorter than L5 (Table 2). In FIG. 13D and Table 1, is shown that the segment width at the dorsal root entry was similar across all lumbar segments and no significant differences across segments were found (Table 2). The distance from the midvertebrae foramen to dorsal rootlets in L11-L4 was similar and then increased at L5 and L6 (FIG. 1E, Table 1), being just L6 significantly higher than L1-L4 (Table 2). These results show significant anatomical differences at L4-L6 segments compared with a relatively similar anatomy in L1-L3 segments. These differences are primarily characterized by an increase in spinal cord diameter and a decrease in segment length in L4-L6, as well as an increase in the distance from the midvertebrae foramen to the dorsal rootlets at the same segments, with a significantly higher distance at L6.

Lumbar Dorsal Root, Rootlets (Root Fibers), and Rootlet Projection Anatomy

As shown in FIG. 14A, the dorsal roots vary in orientation across lumbar segments. Anatomical measurements of the dorsal roots and rootlets are illustrated in FIG. 14B and included: number of dorsal rootlets, root width from bone, rostral and caudal root angles, rostral and caudal root lengths, width across dorsal columns and rostral root-caudal root length. Data (mean, ±SD) from dorsal roots and rootlets anatomy are listed in Table 3. In order to facilitate the comparison between rostral and caudal dorsal root angles, as well as rostral and caudal root lengths from bone, and to emphasize the anatomical differences across lumbar segments (for example, FIG. 14A), means (±SD) are plotted in corresponding FIGS. 14C-D for 7 specimens. While the rostral root angles from L1 to L6 did not vary significantly from one another, the caudal angles showed significant differences (FIG. 14C, Table 3), being L5 smaller than those at L1 and L2 an L6 smaller than L1-L3 (Table 4). Both rostral and caudal root lengths were found similar in L1-L4 (FIG. 14D and Table 3) and then they increased significantly at L5-L6 (Table 4). In FIGS. 14E-H, data per specimen are presented to show variability across animals. The number of dorsal rootlets was consistent across the L1, L2 and L3 segments and gradually increased from L4 to L6 (FIG. 14E, Table 3), being the number of dorsal rootlets higher at L5 compared to L1 and L6 compared to L1-L3 (Table 4). We also found a gradual increase in dorsal root width from bone across spinal cord segments (FIG. 14F, Table 3). In fact, the dorsal root width from bone at L5 was higher compared to L1 as well as L6 compared to L1 and L2 (Table 4). The width across the dorsal columns was generally uniform from L1 to L4, and then exhibited an increase at L5 and L6 (FIG. 14G); however, no statistical differences across spinal segment were found (Table 4). No significant differences in rostral-root to caudal-root distance across lumbar segments were found even though there was a trend towards higher values at L2-L4 when compared to L1 and L5-L6 (FIG. 14H, Table 4). Altogether, neuroanatomical measurements showed non-homogenous morphometric characteristics when comparing L1-L3 and L4-L6. The changes in the most caudal spinal cord segments L4, L5, and L6, included higher number of dorsal rootlets and sharper dorsal roots angles as well as an increase in the rostral and caudal root lengths and root with from bone.

Spine Anatomical Landmarks

Figure 15:
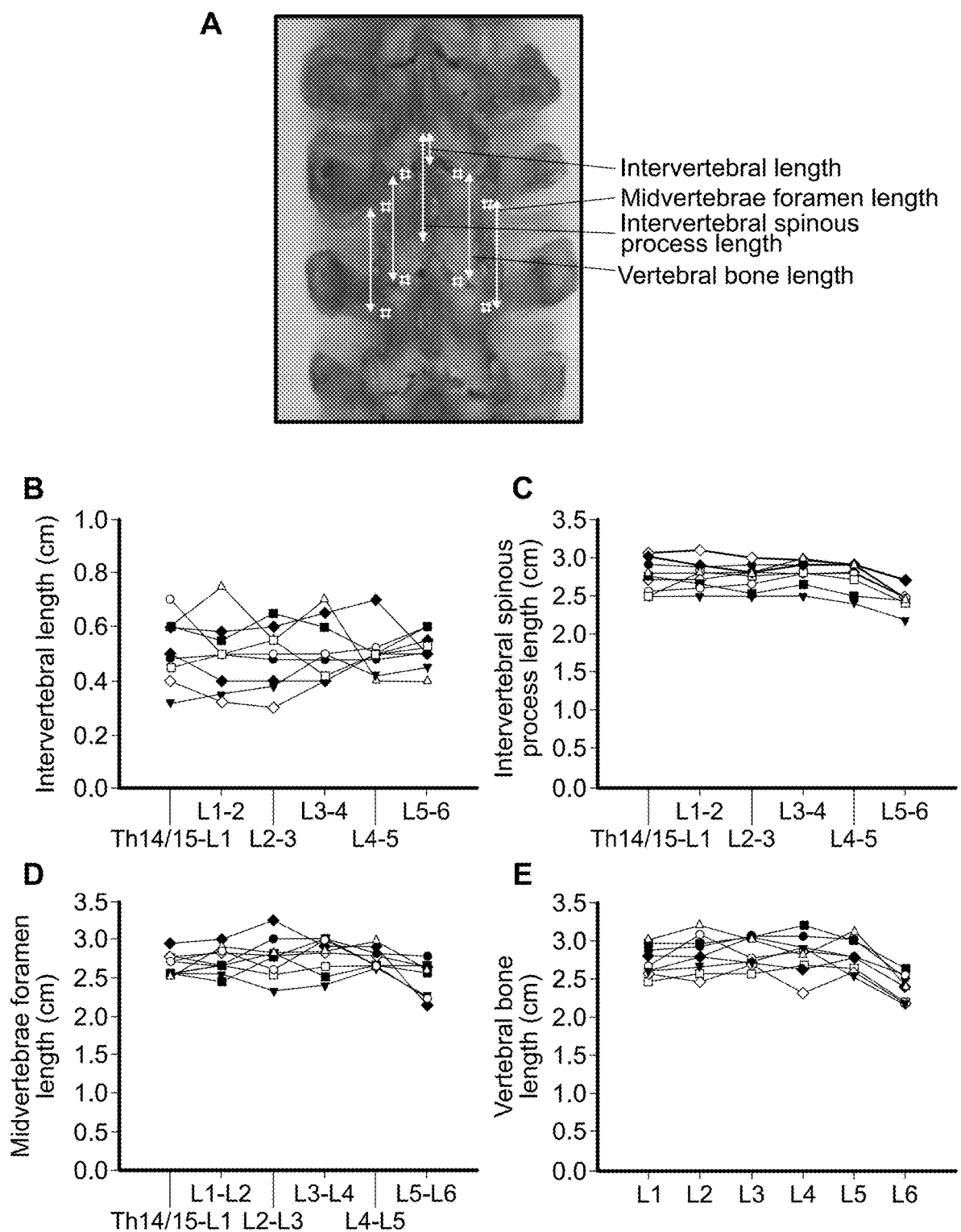
FIG. 15 depicts images of the swine's lumbar spine anatomy. (A) Vertebral landmark measurements. Data per specimen (n=9) across Th14/Th15-L1 to L5-L6 intersegments is shown for: (B) Intervertebral length, (C) Intervertebral spinous process lengths, (D) Midvertebrae foramen length and (E) Vertebral bone length.

Data from intersegmental spine landmarks (features) are summarized in Table 5 and plotted in FIG. 15, these measurements include the following lengths: intervertebral, intervertebral spinous process, midvertebrae foramen and vertebral bone (FIG. 15A). Intervertebral length across lumbar segments is plotted in FIG. 15B per specimen (n=9). This anatomical landmark was not statistically different across lumbar segments (Table 6). Intervertebral spinous process length at L5-L6 was found to be shorter compared to L2-L3, L3-L4 and L4-L5 in all specimens (n=9) as shown in FIG. 15C and Table 6. In FIG. 15D, midvertebrae foramen length is shown per specimen (n=9). This anatomical landmark did not vary significantly across lumbar segments except for L5-L6 which were found to be the shortest (Table 6). Vertebral bone length was similar from L1 to L4, although it was slightly higher at L4 in 8/9 specimens (FIG. 15E), but then decreased significantly at L6 (Table 6). Except for the intervertebral length, the rest of the intersegmental spine landmarks exhibited a decrease in length at the most caudal segments (L5-L6).

Relationship Between Anatomical Landmarks of the Spine and Spinal Cord

A linear regression analysis was performed to examine the intersegmental relationships between the spinal cord and the spine using the following anatomical landmarks: spinal cord segments lengths (FIG. 13C, Table 1), midvertebrae foramen, intervertebral spinous process, and vertebrae bone length (FIG. 15C-E, Table 3). Correlation coefficients are listed in Table 7. The strongest correlations were found between the length of the intervertebral spinous process and the length of the lumbar spinal cord segments, particularly at L2 (r=0.904) and L4 (r=0.858). However, the correlation between the vertebral bone length and the spinal cord segment length was weak as well as the correlation between the midvertebrae foramen and the spinal cord segment length (see Table 7). Due to the high correlation between the intervertebral spinous process length and the spinal cord length at L2, we used this segment as a reference to establish an intersegmental anatomical relationship between the spine and the spinal cord. Then, ratios were established between the mean of the spinal cord segment length across lumbar segments and the mean of L2 intervertebral spinous process length (FIG. 16A, black line and circles). Ratios were similar around the rostral segments (L1, 0.95; L2, 0.98; L3, 0.96 and L4, 0.92) but were lower at L5 and L6 (0.71 and 0.54, respectively). As a reference, the ratios between the mean of the intervertebral spinous process length across segments and the mean of L2 intervertebral spinous process length (blue line and squares: L1, 0.98; L2, 1.00; L3, 1.00; L4, 1.00, L5, 0.90 and L6, 0.86) as well as the ratios between the mean of the spinal cord segment length across segments and the mean of L2 spinal cord segment length (red line and diamonds: L1, 0.96; L2, 1.00; L3, 0.96; L4, 0.94; L5, 0.73 and L6, 0.55) were included (FIG. 16A). In FIG. 16B, diagrams represent the spine (top) and spinal cord (bottom) intersegmental relationship. The blue and red palettes rectangles indicate the intervertebral spinous process lengths and spinal cord segmental lengths, respectively. The L2 segment was selected as a reference as indicated above. Then, the L2 mean intervertebral spinous process length was defined as 100% and intervertebral spinous processes lengths and spinal cord segmental lengths were defined as a percentage with respect to L2. Note that the length of the spinal cord in relation to the vertebrae in the rostral segments (L1 to L3) tends to be similar, while the spinal cord shortening is evident in the L4-L6 segments. Among the spine landmarks described in this study, the intervertebral spinous process length, specifically at segment L2, could be used to establish an anatomical segmental relationship between the spine and the spinal cord in order to target dorsal spinal structures based on vertebral bones landmarks.
Functional Neuroanatomy of the Lumbosacral Spinal Cord Next, the relationship between the EES motor evoked potentials and the neuroanatomy of the spinal cord was analyzed. The amplitude and latency of spinally evoked motor responses was evaluated during EES in proximal sites to the dorsal rootlet projections and in distal sites at intersegmental locations across the lumbar segments. In FIG. 17A, representative examples of spinally evoked ER and MR in proximal (BF) and distal (TA and SOL) muscles in Subject 2 are presented. EES was delivered through electrode contacts located close to the dorsal root entry zone at L5 (BF and SOL) and L6 (TA). Visible motor evoked responses appeared at 2.5 mA in BF and SOL and at 1.75 mA in TA. Averaged latencies were determined for ER (BF, 7.97±0.57 ms; TA, 8.80±0.30 ms and SOL, 9.94±0.69 ms) and MR (BF, 11.77±0.71 ms; TA, 10.74±0.27 ms and SOL, 14.10±1.25 ms). Recruitment curves showing the stimulus amplitude (mA) and the mean (in volts) of the EES motor evoked potentials (±SD) of both ER and MR for the same muscles are depicted in FIG. 17B. While in these examples the ER and MR are clearly defined, the difference between ER and MR in other muscles at different contact locations was not clearly distinguishable (i.e. on FIGS. 18 and 19). At the same time, the amplitudes and latencies of the EES motor evoked potentials were corresponding to the first and second peaks (similar to ER and MR) and were measured in a time window similar to the examples shown in FIG. 17A.
Spinally Evoked Motor Responses from Proximal and Distal Lumbar Segments Proximal Segments (L1-L4): Higher amplitudes were consistently observed for both proximal and distal muscles when EES (2.5 mA stimulus amplitude) was delivered over the dorsal rootlet projections within segments (L1, L2 and L3) compared to when stimulated in between the segments (L1-L2, L2-L3 and L3-L4) (FIG. 18A). Maximal amplitudes of responses were expressed as 100% (±SEM) and were found when stimulating at L3 for proximal (GLU, ±25.96%; RF, ±34.86% and BF, ±35.75%) and distal muscles (TA, ±15.92%; GAS, ±28.83% and SOL, ±15.89%). On the other hand, lowest amplitude responses occurred in proximal (GLU, 1.78±0.39%; RF, 7.08±1.42%; BF 1.43±0.64%) and distal (TA, 29.35±8.86%; SOL, 3.44±1.67%) muscles when EES was delivered at L3-L4, with the exception of GAS for which the lowest response was recorded when stimulating at L2-L3 (3.44±1.67%).

EES responses in GLU evoked stimulating over the dorsal rootlet projection at L1, L2 and L3 were higher compared to stimulation delivered distally from dorsal root entry zones at L1-L2, L2-L3 and L3-L4 (p<0.05). RF motor responses in L1 and L3 were higher just compared to L3-L4 (p<0.001) while motor responses evoked in L2 were higher compared to all intersegmental electrode positions: L1-L2, L2-L3 (p<0.05) and L3-L4 (p<0.001). Similarly to GLU, BF exhibited higher amplitudes when stimulating at L1 compared to L2-L3 (p<0.05) and L3-L4 (p<0.001) as well as stimulation in L2 compared to L1-L2, L2-L3 (p<0.05) and L3-L4 (p<0.001) and L3 compared to L1-L2, L2-L3 (p<0.05) and L3-L4 (p<0.001). A similar pattern was observed in distal muscles. Motor responses in TA evoked by stimulation over the dorsal rootlet projection at L2 were higher compared to L1-L2 and L3-L4 (p<0.05) as well as L3 compared to L1-L2 (p<0.05) and L3-L4 (p<0.001). Motor responses however, were not higher compared to L2-L3, where TA had a relatively high amplitude response (68.78±15.56%) as shown on FIG. 18A. Amplitudes obtained in GAS when stimulating over dorsal root entry zone at L1, L2 and L3 were higher compared to L1-L2 (p<0.05) and L2-L3 (p<0.001) but not to L3-L4. SOL motor potentials evoked were also higher compared to L3-L4 (p<0.05). Finally, SOL exhibited higher amplitudes in L1, L2 and L3 compared to all intersegmental electrode positions (L1-L2, L2-L3 and L3-L4, p<0.05, being p<0.001 in L2 compared to L3-L4).

These results show that EES-induced motor responses are highly dependent upon position of the electrode over the dorsal roots entry zone. Shifting the electrode just a few millimeters away from that area, for example from L1 to L1-L2, leads to a significant increase in motor thresholds, while shifting the electrode a few centimeters, for example from L1 to L3 segment, causes no significant difference in evoked responses in both proximal and distal muscles. Particularly, maximal peak-to-peak amplitudes were observed when EES was delivered at L3 in all recorded muscles and no significant differences were found when comparing amplitudes with those in L1 or L2 (FIG. 18A), where electrode was located ≈5.2 cm and ≈2.6 cm apart, respectively. A dramatic decrease in amplitudes was observed when EES was applied at intersegmental locations compared with stimulation over the dorsal root entry zone in nearby electrode locations. For instance, the difference in amplitudes when EES was delivered at L3 and L3-L4 was up to 90% in proximal and 60% in distal muscles (FIG. 18A), considering that the distance between L3 and L3-L4 electrode positions was approximately 1cm. In FIG. 18B, examples of ten averaged EES-evoked motor responses applying 1.4 mA are shown for proximal and distal muscles. Note the difference in amplitudes between evoked responses when the electrode was placed over the dorsal root entry at L3 (highest amplitudes, 100%) and between L3-L4 segments, distally from dorsal rootlets (lower amplitudes). Mean latencies (±SD) of the first and second identified peaks (on L3 rootlets) are plotted in the bottom panel on FIG. 18B.

Distal Segments (L4-L6): Amplitudes and latencies of EES evoked motor potentials in L4-L6 were investigated using the multi-contact rod array placed on the midline of the spinal cord in subject 2 (FIG. 19). As shown in FIGS. 12 and 13, L4-L6 segments exhibit significant anatomical differences compared with the relatively invariant rostral segments L1-L3. The shortening of caudal segments is accompanied with an increasing number of dorsal roots and a change in angles as they enter the spinal cord (FIG. 13C, 14C,E). These anatomical differences preclude determining intersegmental positions clearly, as distance between dorsal roots is smaller, especially from L5 to L6 (≈0.19 cm). Positioning of electrode contacts was related to the proximity to dorsal root entry zone (L4, L5 and L6) and neighboring intersegmental locations (L4-L5 and L5-L6). Highest amplitudes during EES-evoked responses were expressed as 100% (±SEM). In general, maximal amplitudes were evoked delivering EES at the most caudal electrode locations: L5-L6 in BF (±2.7%) and TA (±4.99%) and L6 in GLU (±1.4%), GAS (±2.46%) and SOL (±0.52%). The exception was RF, which exhibited maximal amplitude (100%) when EES was delivered at L4 (±1.17%) as shown in FIG. 19. On the other hand, EES at L4-L5 evoked the lowest amplitudes in GLU (3.50±0.05%), BF (0.97±0.04%), TA (0.62±0.05%), GAS (3.85±0.32%) and SOL (0.48±0.04%). RF exhibited the lowest amplitude at L5 (4.86±0.04%) but not significantly different from that in L4-L5 (4.92±0.35%) as shown in FIG. 19. As shown in the previous section, lowest amplitudes at L4-L5 can be attributed to the fact that the contact position was located in an intersegmental location (between two adjacent dorsal rootlet projections), distally from dorsal rootlet projections. The distance between these segments was about 0.67 cm. (see for example FIG. 14A and diagram on FIG. 16B for comparison with intersegmental distance between L5 and L6). Multiple comparisons showed that the amplitude of the GLU motor response when stimulating at the most caudal electrode positions L5, L5-L6 and L6 were higher compared to more rostral segments. In fact, higher amplitudes were evoked in L6 compared to L4-L5, L4 ($p<0.001$) and L5 ($p<0.05$). Stimulation in the adjacent position L5-L6, produced higher amplitudes compared to that in L4-L5 ($p<0.001$) and L4 ($p<0.05$). Albeit stimulation at L5 evoked a small amplitude (27.26±0.12%) compared to that in more caudal segments L5-L6 (70.24±6.59%) and L6 (100±1.46%), EES in L5 evoked higher amplitudes than that in L4-L5 ($p<0.05$). Evoked responses in BF stimulating at L4 produced higher amplitudes compared with adjacent position L4-L5 ($p<0.05$). EES at L5-L6 exhibited higher amplitudes than the intersegmental position at L4-L5 ($p<0.001$) but also compared to L5 ($p<0.01$) and L4 ($p<0.05$). Also, EES at L6 produced higher amplitudes compared to L4-L5 ($p<0.001$) and L5 ($p<0.05$). The amplitude of the RF motor potentials when delivering EES at L4 was higher compared to that in L4-L5, L5 ($p<0.001$) and L6 ($p<0.05$). Moreover, amplitude of the motor response evoked at L5-L6 was also higher than that in L4-L5 and L5 ($p<0.05$). Similar results were obtained for distal muscles, where EES at caudal electrode positions (L5-L6 and L6) evoked higher amplitudes than motor potentials stimulating at more rostral electrode positions (L4, L4-L5 and L5). The exception was the amplitude in TA when EES was delivered at L4, being 51.09±0.42% with respect of the maximal amplitude (100%) evoked at L5-L6 (FIG. 19A). The amplitude of TA motor potentials evoked at L5-L6 was higher compared to L4-L5, L6 ($p<0.001$) and L5 ($p<0.05$) as well as EES at L4 and L5 compared to amplitudes recorded in the adjacent contact location L4-L5 ($p<0.001$ and $p<0.05$ respectively). EES at L4 was also higher compared to L6 ($p<0.05$). Similar motor response amplitudes were recorded in GAS and SOL with EES at L6 (100% in both muscles). EES at L6 in GAS evoked higher amplitudes than those in L4-L5, L5 ($p<0.001$) and L4 ($p<0.05$), similar pattern was observed in SOL (L6 vs L4-L5, L4, $p<0.001$ and vs L5 $p<0.05$). Moreover, stimulation in the adjacent electrode position L5-L6 in GAS and SOL evoked higher amplitudes compared to L4-L5 ($p<0.001$). EES in the same intermediate electrode position L5-L6 produced higher amplitudes in GAS compared to L5 ($p<0.05$) and in SOL compared to L4 ($p<0.05$). Finally, motor responses in SOL evoked by stimulation at L5, produced higher amplitudes compared to those at L4-L5, ($p<0.05$). Representative examples of ten averaged EES motor responses evoked at 1.6 mA are shown for proximal and distal muscles in FIG. 19B. Mean latencies (±SD) of the first and second identified peaks (EES was delivered at L6) are shown in the bottom panel on FIG. 19B. Overall, results of functional neuroanatomy of lumbar segments show that the peak-to-peak amplitude of EES evoked motor responses across lumbar segments is highly dependent upon the proximity of the electrode to the dorsal rootlets entry zone and less dependent to the position of the electrode across different spinal segments, regardless of whether they were evoked by the spherical single electrode (FIG. 18) or the multi-contact rod array (FIG. 19).

TABLE 1

Spinal cord measurements

| | L1 | L2 | L3 | L4 | L5 | L6 |
|---|---|---|---|---|---|---|
| SCD | 0.75 ± 0.10 | 0.78 ± 0.080 | 0.81 ± 0.08 | 0.90 ± 0.08 | 0.94 ± 0.12 | 0.89 ± 0.09 |
| SLcc | 2.62 ± 0.20 | 2.69 ± 0.28 | 2.64 ± 0.28 | 2.53 ± 0.30 | 1.93 ± 0.33 | 1.48 ± 0.29 |
| SLDRE | 0.47 ± 0.06 | 0.50 ± 0.09 | 0.51 ± 0.11 | 0.54 ± 0.09 | 0.56 ± 0.10 | 0.53 ± 0.07 |
| MFR | 1.25 ± 0.19 | 1.19 ± 0.24 | 1.21 ± 0.26 | 1.22 ± 0.14 | 1.58 ± 0.29 | 2.17 ± 0.29 |

Numbers are in cm (±SD). Nomenclature: SCD, Spinal cord transverse diameter; SLcc, Spinal cord segment length caudal-to-caudal; SLDRE, Segment length at dorsal root entry; MFR, Midvertebrae foramen to rootlets length. n = 9.

TABLE 2

Anatomical spinal cord comparisons across spinal segments

| Anatomical landmark | | |
|---|---|---|
| | L4 | L1, $p < 0.05$ |
| SCD | L5 | L1, L2, $p < 0.01$ |
| | L6 | L1, $p < 0.05$ |
| SLcc | L5 | L1, L2, L3, L4, $p < 0.001$; L6 $p < 0.05$ |
| | L6 | L1, L2, L3, L4, $p < 0.001$ |
| SLDRE | | ND |
| MFR* | L6 | L1, L4 $p < 0.01$; L2, L3, $p < 0.001$ |

ANOVA test. All pairwise multiple comparison (Holm-Sidak method).

*Tukey test, all pairwise multiple comparison.

Nomenclature: SCD, Spinal cord transverse diameter; SLcc, Spinal cord segment length caudal-to-caudal; SLDRE, Segment length at dorsal root entry; MFR, Midvertebrae foramen to rootlets length.

ND, No statistical differences were found.

TABLE 3

Dorsal spinal rootlet projection parameters

| | L1 | L2 | L3 | L4 | L5 | L6 |
|---|---|---|---|---|---|---|
| rRA (°), n = 7 | 159.72 ± 4.19 | 159.8 ± 7.43 | 165.81 ± 5.47 | 161.48 ± 3.42 | 164.95 ± 2.05 | 160.55 ± 5.45 |
| cRA (°), n = 7 | 138.43 ± 10.79 | 138.33 ± 12.88 | 124.62 ± 35.7 | 56.78 ± 13.78 | 45.43 ± 20.77 | 34.13 ± 11.72 |
| rR (mm), n = 7 | 7.84 ± 2.03 | 9.24 ± 2.99 | 11.31 ± 2.33 | 11.64 ± 2.77 | 12.86 ± 5.84 | 16.89 ± 5.84 |
| cR (mm), n = 7 | 4.52 ± 1.31 | 4.89 ± 1.54 | 4.18 ± 1.40 | 4.26 ± 0.68 | 7.08 ± 2.64 | 10.79 ± 3.24 |
| DR (#), n = 9 | 15.11 ± 6.49 | 15.78 ± 4.23 | 15.0 ± 4.18 | 23.55 ± 10.45 | 26.22 ± 8.39 | 30.22 ± 5.69 |
| rWB (mm), n = 6 | 2.85 ± 0.80 | 2.96 ± 0.57 | 3.27 ± 0.73 | 5.43 ± 0.64 | 6.13 ± 0.62 | 6.87 ± 1.04 |
| DC (mm), n = 7 | 3.77 ± 0.59 | 4.03 ± 0.39 | 4.38 ± 0.55 | 4.46 ± 0.40 | 4.92 ± 0.52 | 5.09 ± 0.61 |
| rR-cR (mm), n = 6 | 12.94 ± 0.32 | 14.43 ± 0.47 | 16.12 ± 0.26 | 14.19 ± 0.14 | 12.97 ± 0.27 | 12.76 ± 0.59 |

Nomenclature: rRA, rostral root angle; cRA, caudal root angle; rR, rostral root length; cR, caudal root length; DR, dorsal rootlets; rWB, root width from bone; DC, width across dorsal columns; rR-cR, rostral root to caudal root length.

TABLE 4

Anatomical dorsal spinal cord comparisons across spinal segments

| Anatomical landmark | | |
|---|---|---|
| rRA | | ND |
| cRA* | L5 | L1, L2, p < 0.05 |
| | L6 | L1, L2, L3 p < 0.01 |
| rR* | L6 | L1, p < 0.01; L2 p < 0.05 |
| cR | L5 | L1, L3, L4, p < 0.05; L6, p < 0.01 |
| | L6 | L1, L2, L3, L4, p < 0.001; |
| DR | L5 | L1, p < 0.05 |
| | L6 | L1, L2, L3 p < 0.01 |
| rWB* | L5 | L1, p < 0.05 |
| | L6 | L1, p < 0.01 L2 p < 0.05 |
| DC | | ND |
| rR-cR | | ND |

ANOVA test. All pairwise multiple comparison (Tukey test).
*All pairwise multiple comparison (Dunn test).
Nomenclature: DR, dorsal rootlets; rWB, root width from bone; rRA, rostral root angle; cRA, caudal root angle; rR, rostral root length; cR, caudal root length; DC, width across dorsal columns; rR-cR, rostral root to caudal root length.
ND, No statistical differences were found.

TABLE 5

Intersegmental spine measurements

| | Th14/Th15-L1 | L1-L2 | L2-L3 | L3-L4 | L4-L5 | L5-L6 | L6-S1 |
|---|---|---|---|---|---|---|---|
| IL | 0.51 ± 0.11 | 0.49 ± 0.13 | 0.49 ± 0.11 | 0.51 ± 0.11 | 0.50 ± 0.08 | 0.48 ± 0.13 | 0.47 ± 0.08 |
| ISPL | 2.69 ± 0.15 | 2.73 ± 0.11 | 2.75 ± 0.20 | 2.75 ± 0.16 | 2.46 ± 0.15 | 2.35 ± 0.14 | |
| MVFL | 2.67 ± 0.16 | 2.72 ± 0.19 | 2.76 ± 0.26 | 2.78 ± 0.23 | 2.74 ± 0.15 | 2.49 ± 0.22 | |

| | L1 | L2 | L3 | L4 | L5 | L6 |
|---|---|---|---|---|---|---|
| VBL | 2.66 ± 0.16 | 2.76 ± 0.19 | 2.79 ± 0.19 | 2.77 ± 0.25 | 2.74 ± 0.18 | 2.38 ± 0.36 |

Numbers are in cm (±SD). Nomenclature: IL, intervertebral length; ISPL, Intervertebral spinous processlength; MVFL, Midvertebrae foramen length; VBL, vertebral bone length.
n = 9

TABLE 6

Anatomical intersegmental spine comparisons across spinal segments

| Anatomical landmark | | |
|---|---|---|
| IL | | ND |
| MVFL | L4-L5 | L5-L6, p < 0.01 |
| | L5-L6 | L1-L2, p < 0.05; L2-L3, p < 0.01; L3-L4, p < 0.001 |
| ISPL | L4-L5 | L5-L6, p < 0.05 |
| | L5-L6 | L2-L3, L3-L4, p < 0.05 |
| VBL | L6 | L1, p < 0.01, L2, L3, L4, L5, p < 0.001 |

ANOVA test. All pairwise multiple comparison (Holm-Sidak method).
Nomenclature: IL, intervertebral length; MVFL, Midvertebrae foramen length; ISPL, Intervertebral spinous process length; VBL, vertebral bone length.
ND, No statistical differences were found.

TABLE 7

Linear correlation analysis between vertebrae bone and spinal cord

| Spinal level | ISP-SLcc | VB-SLcc | MVF-SLcc |
|---|---|---|---|
| L1 | 0.711 | 0.359 | 0.263 |
| L2 | 0.904 | 0.329 | 0.161 |
| L3 | 0.541 | 0.482 | 0.100 |
| L4 | 0.858 | 0.087 | 0.217 |
| L5 | 0.204 | 0.335 | 0.469 |
| L6 | 0.236 | 0.366 | 0.286 |

Numbers are coefficients (r).
Nomenclature: ISP, Intervertebral spinous process length; VB, vertebral bone length; MVF, Midvertebrae foramen length; SC, spinal cord segment length (caudal to caudal).
n = 9.

Discussion

This example study provides evidence of the influence of electrode position in relation to the dorsal roots spatial orientation on effect of EES.

Anatomy of the Swine Lumbar Spinal Cord

Figure 14:
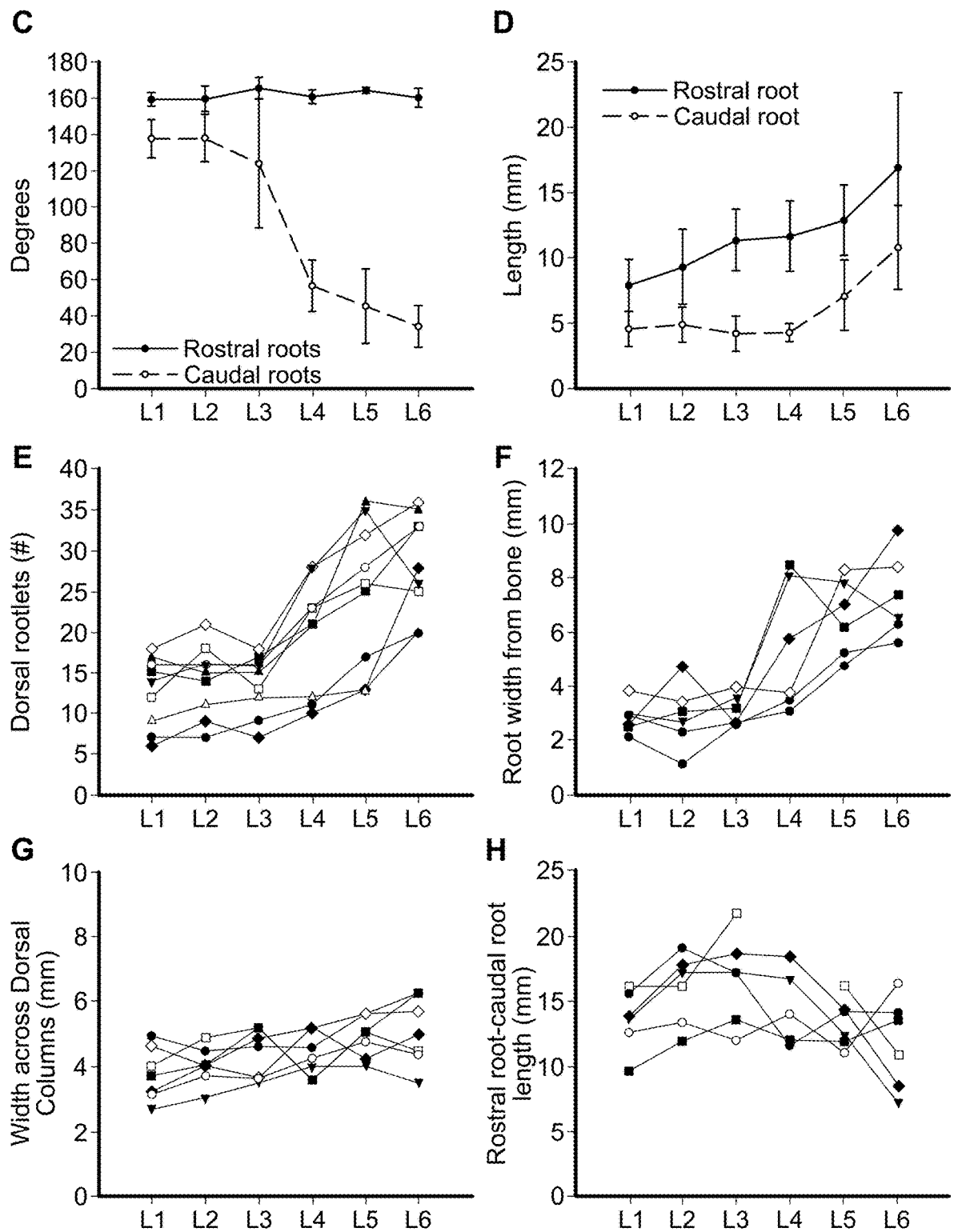
FIG. 14 depicts images of the dorsal root anatomy of the swine's lumbar spinal cord. (A) Dorsal roots orientation in the swine lumbar spinal cord (Th14/15-L6 segments). Note the changes in orientation of angles, from rostral to caudal segments, denoted by dotted lines. Changes in dorsal root caudal angles are more evident in L4-L6. (B) Dorsal spinal cord anatomical measurements and dorsal rootlets count (inset). (C) Rostral (black dots) and caudal (white dots) dorsal root angles (mean±SD) (n=5). (D) Rostral (black dots) and caudal (white dots) root lengths (Mean±SD) (n=5). Data per specimen across lumbar segments is shown for: (E) Number of dorsal rootlets (n=9), (F) Root width from bone (n=6), (G) Width across dorsal columns (n=7) and (H) Rostral root-caudal root length (n=6).

Relevant anatomical landmarks in bony structures and spinal cord are described herein. Still, anatomical differences between human and swine spinal cord should be taken into account, for example, the number of lumbar vertebrae (5 in human and 6 in swine) and some vertebral morphometric characteristics. In terms of the spinal cord anatomy, the length of the spinal cord in humans terminates at L1-L2 while the swine spinal cord continues to lower lumbosacral segments. In addition, segment length in the swine (FIG. 13C and Table 1) is also longer compared to humans. At lumbar segments, the number of dorsal roots at the rootlet projection in humans has been shown to range between 4.7±0.6 at L5 to 6.7±1.2 at L3. In the swine, the highest values were found, ranging from 15.0±4.18 at L3, to 30.22±5.69 at L6 (FIG. 14D). In the swine, significant anatomical differences in L5 and L6 segments were found compared to L1-L4 segments (FIGS. 13-14 and Tables 1-2). The shortening of the spinal cord in L5-L6 is related with an increase in the midvertebrae foramen to rootlets distance (FIG. 13D). A decrease in L5-L6 caudal root angles (FIG. 14C) and an increase in the root-to-root length in these segments were also found (FIG. 14E). A significant increase in rostral and caudal root length and root width from bone in L6 compared to L1-L3 was also observed (FIG. 14F). Spine morphometric differences are not only observed in the swine, but also in different large animals used as translational models to assess vertebral biomechanical properties, spine pathology and surgical implantation techniques; therefore, specific anatomical differences should be noticed according to the purpose of the research. Another aspect of the swine model that should be considered is the weight (size) of the animals as conventional breeds can reach more than 100 kg typically at four months. This study used swine with similar weight (25-40 kg) as reported in papers describing vertebral morphometry, feasibility of EES as a restorative paradigms and stereotactic-guided micro stimulation. For chronic experiments with EES, minipigs breeds might be considered as an option in terms of their growth and handling. The study of the effect of EES in relation to the dorsal neuroanatomy provided here contributes to filling the gaps regarding the swine as a large animal model during neuromodulation strategies.

Intersegmental Correlation Between Vertebrae and Spinal Cord

This study measured intersegmental vertebral landmarks (features) (FIG. 15) instead of measuring anatomical dimensions in isolated vertebrae. After performing linear regression analysis (Table 4), high correlation coefficients between the intervertebral spinous process lengths and the spinal cord segment lengths were found, particularly at L2 (r=0.9). This approach denoted similarities between L1-L3 segments and the shortening of the spinal cord in relationship to the spine at segments L1-L4. For this reason, L2 intervertebral spinous process length was selected as segmental reference to establish ratios between the spine and spinal cord and to develop a model of the spinal cord including features of the dorsal root anatomy (FIG. 16A, B). In some aspects, correlations between intersegmental spine and spinal cord landmarks can be used in preclinical surgical maneuvers. Moreover, the anatomical data and particularly intersegmental correlations provided here may be combined with imaging studies in order to develop a 3D-model of the spinal cord to help in the implementation of specific targeting during implantation procedures.

EES Evoked Motor Responses in the Swine Model

Initially described on rodent, three types of responses are observed during EES: ER, related with direct activation of motor fibers (latency about 3-5 ms); MR with latency (5-9 ms) associated with the activation of muscles afferents (group I and group II) and with formation of EMG bursts, and late response (LR) with a latency more than 10 ms related with functional recovery of spinal cord circuitry after SCI. MR latencies have been reported from 9 ms to 17 ms in SCI patients during EES, while others have reported latencies in a range between 6 ms to 20 ms. Higher latencies ranging between 15.6±2.9 ms (rectus femoris) to 31.0±3.6 ms (flexor digitorum brevis) described as monosynaptic responses were evoked in healthy individuals during percutaneous electrical stimulation. Discrepancy in latencies can be attributed to different placement of electrodes in relation of spinal structures (EES vs percutaneous electrical stimulation), segmental electrode location, and distinction between ER and MR in evoked motor potentials. This study shows the characteristics of the EES evoked motor responses in terms of amplitude and latency in the swine model (FIGS. 17-19).

The latencies of EES evoked motor responses were found to be close to the human. FIG. 17A clearly shows ER and MR, however, in many cases it was not easy to distinguish between both components, similar to what was also described in human studies.

The Amplitude of the EES Evoked Motor Responses Depends on Stimulating Electrode Proximity to Dorsal Root Entry Zone In previous studies of healthy and chronic SCI rats, epidural electrodes were placed on the midline of the spinal cord, typically, at L2 and/or S1, and different motor responses based on amplitude and waveform were observed during stimulation. These differences were never related with the electrode position in relation to the spinal cord dorsal structures. Our results show that EES delivered close to the dorsal rootlet projections provide the most robust motor responses (FIGS. 18-19). In general, the amplitude of the motor evoked responses was higher with the electrode placed in proximity to the dorsal rootlet projections, compared to the responses recorded with the stimulating electrode in between the dorsal rootlet projections (FIGS. 18-19). The latter was clearly evident with single electrode stimulation over the L1, L2 and L3 dorsal root entry zones, compared to EES at intermediate positions (L1-L2, L2-L3 and L3-L4). In fact, changes in EES evoked motor responses were similar in proximal and distal muscles with exception of the relative high amplitude in TA when EES was applied at L2-L3 (FIG. 18A). The influence of electrode placement in relation to the dorsal rootlet projections was even more critical than position of electrode in relation to different spinal segments (rostral vs. caudal electrode position). For example, maximal peak-to-peak amplitudes were observed when EES was delivered at L3 in most muscles recorded, but no significant differences were found when comparing EES at L1 or L2 (FIG. 18A), where electrode was located ≈5.2 cm and ≈2.6 cm apart, respectively. Moreover, a dramatic decrease in amplitude was observed when comparing nearby electrode locations, for example, the distance between L3 and L3-L4 electrode positions was 1 cm approximately but the difference in amplitudes was up to 90% in proximal and 60% in distal muscles (FIG. 18A). When the multi-contact rod array was placed on the midline of the spinal cord spanning L4-L6, maximum amplitudes (100%) were observed during stimulation at locations close to the dorsal roots entrance zones, for example at L6 for GLU, GAS and SOL, while EES applied at L4 produced maximal amplitude in RF. At the same time, BF and TA amplitudes were maximal when stimulating at L5-L6 (FIG. 19A). Minimal amplitudes were observed in all muscles when EES was applied at L4-L5 (FIG. 19A). Interestingly, increasing amplitudes from L4-L5 electrode position to L6 was observed in GLU, GAS and SOL muscles and similar pattern was observed in RF and TA muscles with maximal amplitudes at L5-L6. The proximity of dorsal rootlet projections particularly between L5 and L6 could in part explain our results. Location of stimulating electrodes proximal to the dorsal rootlet projections in L5-L6 could provide more specific responses as observed using the single electrode in L1,L2 and L3(FIG. 18). In summary, the electrode position in relation to the dorsal roots anatomy is a critical factor that produces a stronger impact on EES rather than shifting the electrode to rostral or caudal segments.

Conclusions

In this study, evaluation of functional neuroanatomy of the swine spinal cord was performed based on EES evoked motor responses. Examination of anatomical spine and spinal cord landmarks showed significant differences from rostral to caudal lumbar segments and particularly between L1-L3 and L5-L6. Among the intersegmental landmarks, the intervertebral spinous process length and particularly at L2, could be used as an anatomical reference to establish a relationship between the spine and spinal cord. The results demonstrate that amplitude of the EES evoked motor responses, particularly the MR (monosynaptic response), dramatically depends on the position of the stimulating electrode in relationship to the dorsal root entry zones.

Figure 33A:
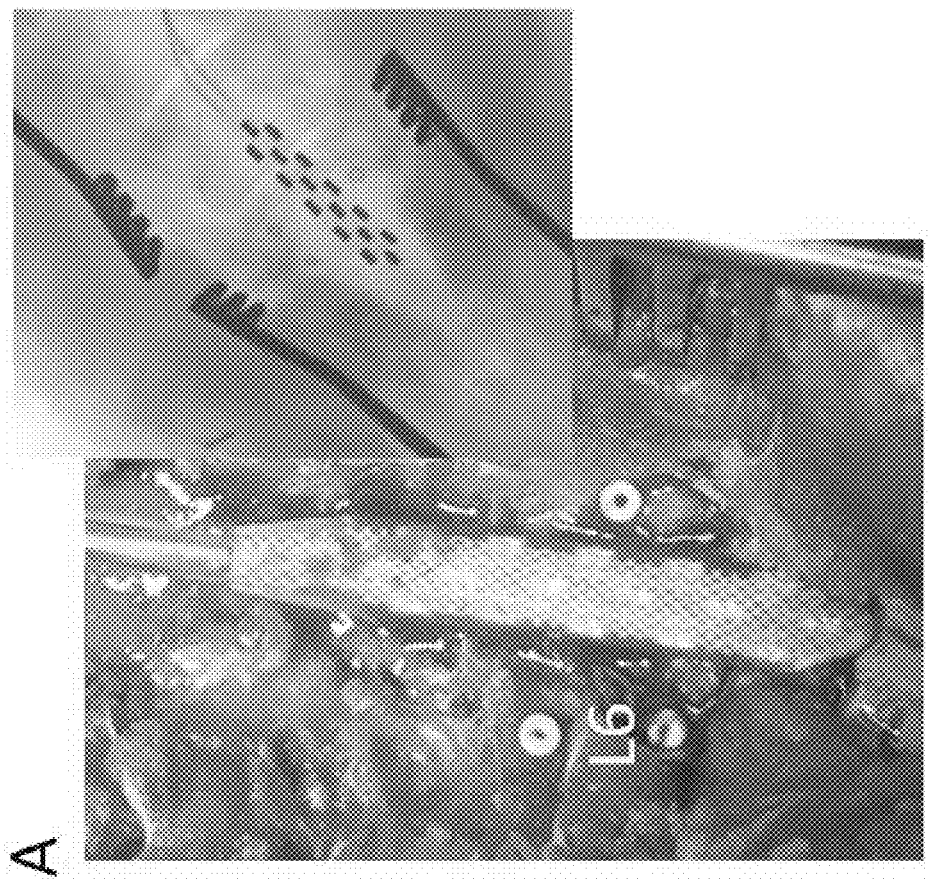
FIGS. 33A-D depict epidural electrical stimulation evoked activation comparison in domestic swine between a commercially available MEDTRONIC 5-6-5 paddle array and a custom dorsal rootlet projection (DRP) anatomy specific array.
Figure 33B:
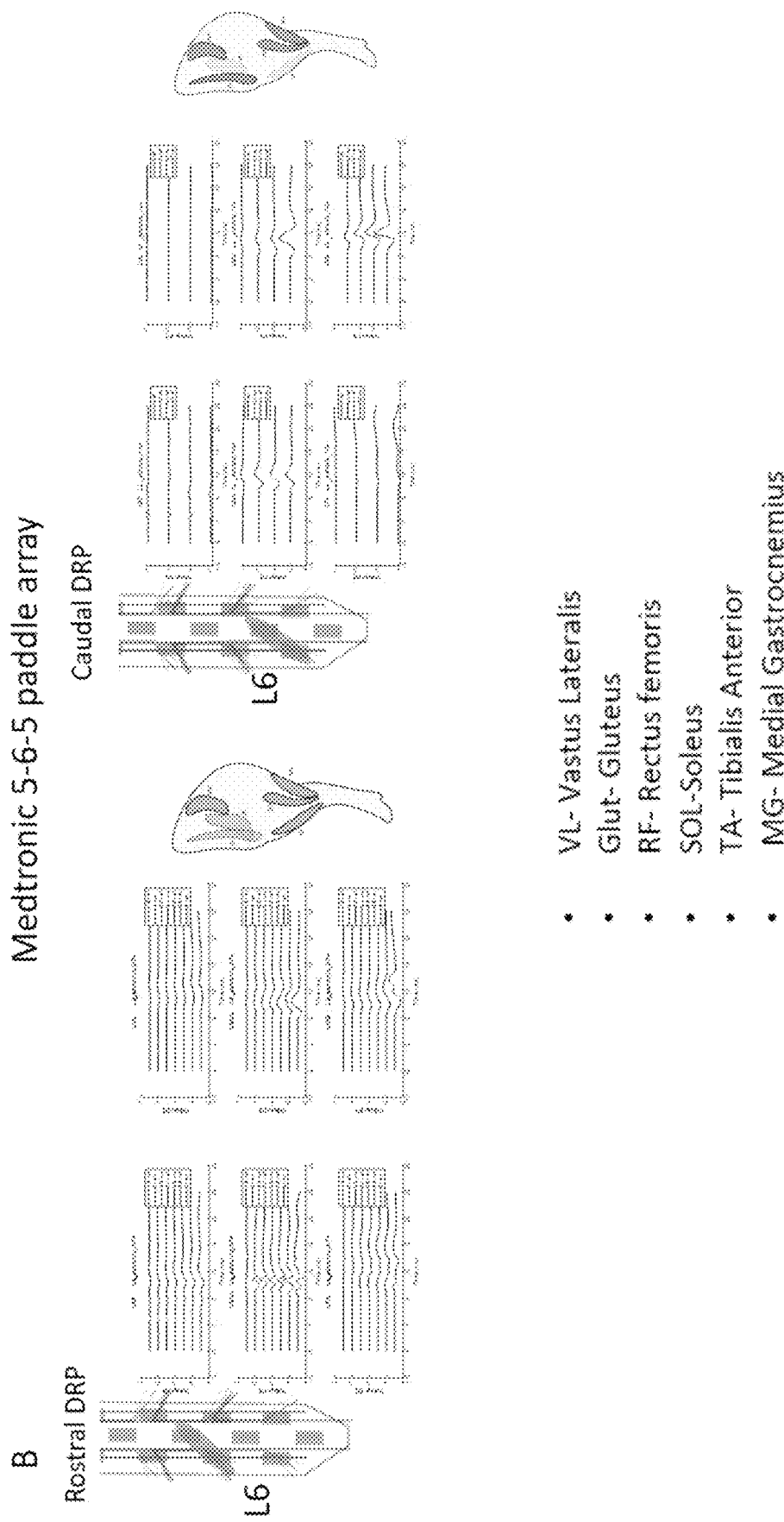
Figure 33C:
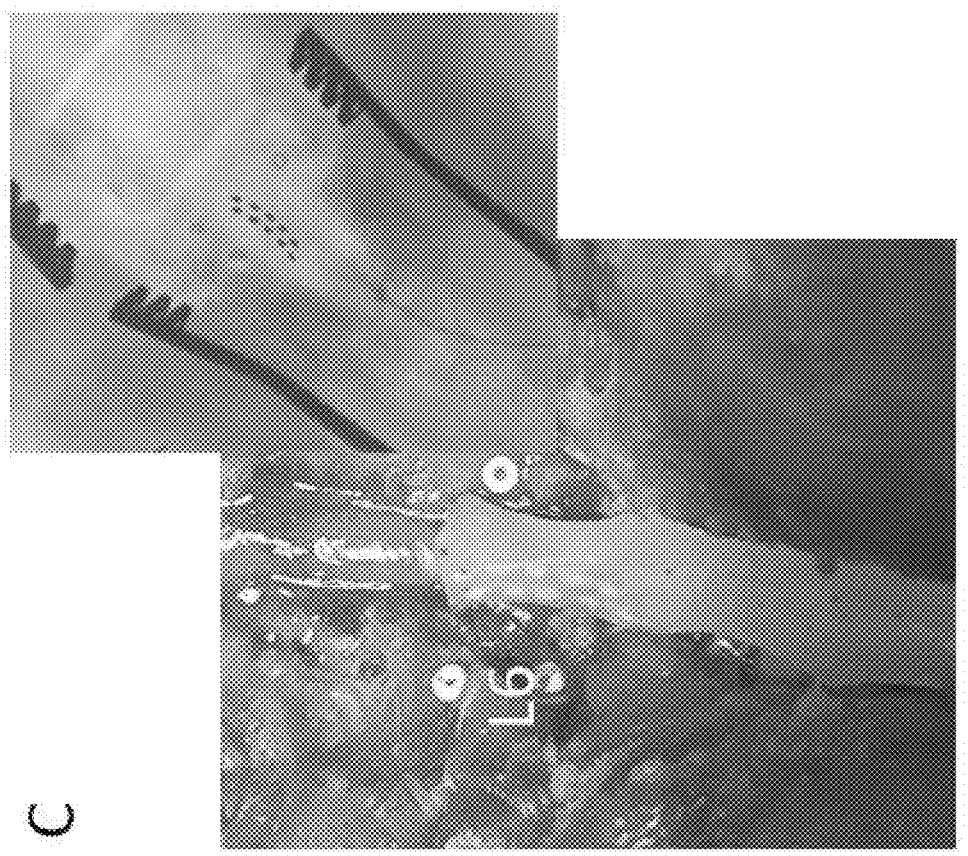
Figure 33D:
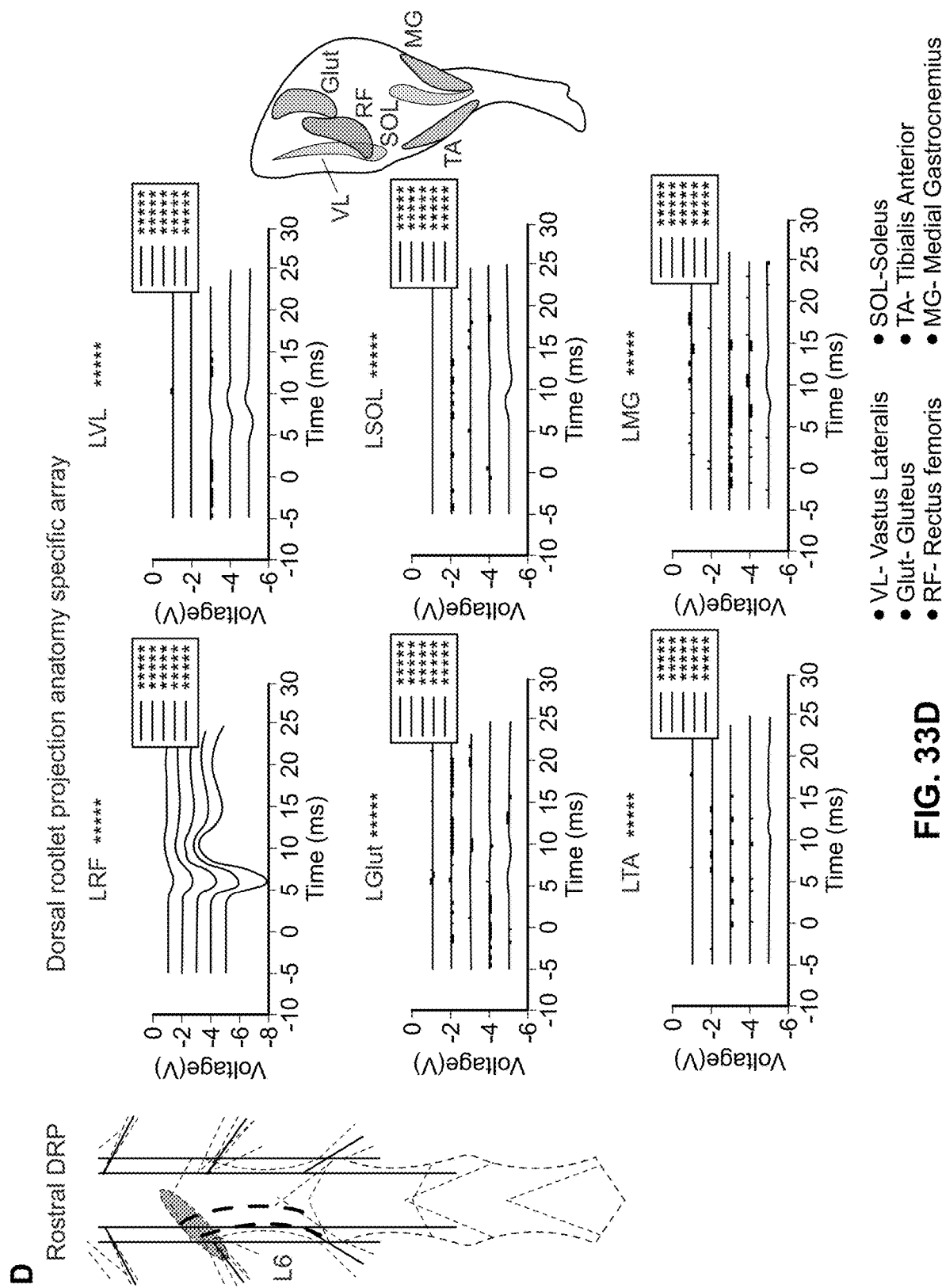
Figure 33D:
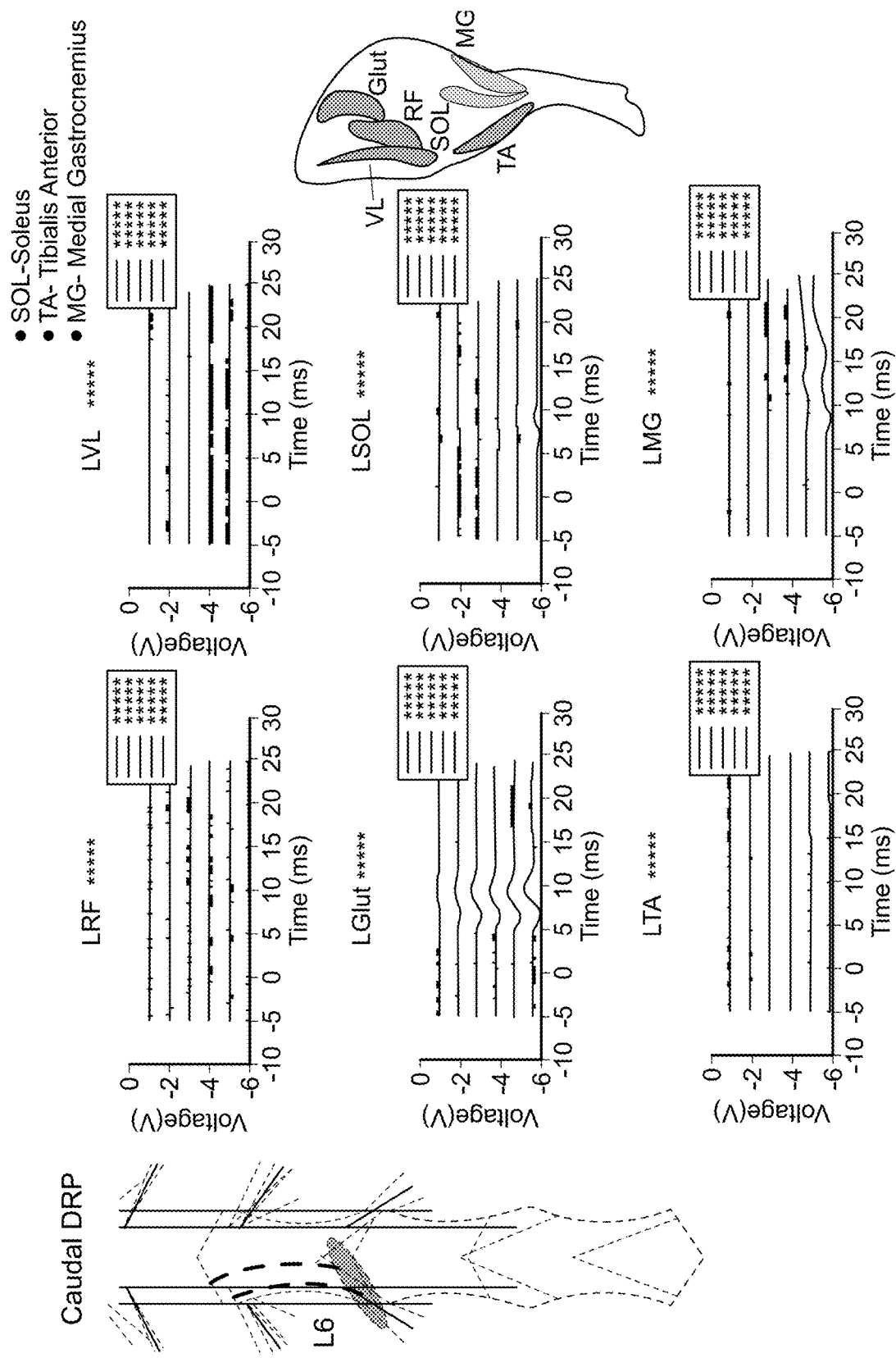

FIGS. 33A-D depict epidural electrical stimulation evoked activation comparison in domestic swine between a commercially available MEDTRONIC 5-6-5 paddle array and a custom dorsal rootlet projection (DRP) anatomy specific array configured according to certain innovative aspects of the subject matter disclosed herein. Hind limb EMG was recorded from VL—Vastus Lateralis, Glut—Gluteus, RF—Rectus femoris, SOL-Soleus, TA—Tibialis Anterior, MG—Medial Gastrocnemius, while a same region of the spinal cord was activated using a voltage level above motor threshold. FIG. 33A show images of the MEDTRONIC 5-6-5 paddle array implanted in domestic swine at Lumbar-6 (L6) segment, and fluoroscopy image showing location of the array with respect to vertebrae. FIG. 33B depicts plots of EMG activation during stimulation of rostral region of L6 DRP VS EMG activation during stimulation of caudal region of L6 DRP using the MEDTRONIC 5-6-5 paddle array. In addition to EMG response, muscle activation is also depicted. The little amount of difference in activated muscle groups and same muscles (Glut, SOL, MG) shows strong activation resulting from both configurations. FIG. 33C shows images of the custom DRP anatomy specific array in the same swine at the same spinal segment (L6), and fluoroscopy image showing location of the array with respect to vertebrae. The custom DRP anatomy specific array was placed at the same location as the MEDTRONIC array. FIG. 33D depicts plots of EMG activation during stimulation of rostral region of L6 DRP VS EMG activation during stimulation of caudal region of L6 DRP. Almost no overlap was observed between stimulation using the two configurations, demonstrating improved selectivity of custom array in activation of DRP.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non transitory program carrier for execution by, or to control the operation of, data processing apparatus. Alternatively or in addition, the program instructions can be encoded on an artificially generated propagated signal, e.g., a machine-generated electrical, optical, or electromagnetic signal, that is generated to encode information for transmission to suitable receiver apparatus for execution by a data processing apparatus. The computer storage medium can be a machine-readable storage device, a machine-readable storage substrate, a random or serial access memory device, or a combination of one or more of them. The computer storage medium is not, however, a propagated signal.

The term "data processing apparatus" encompasses all kinds of apparatus, devices, and machines for processing data, including by way of example a programmable processor, a computer, or multiple processors or computers. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, or a combination of one or more of them.

A computer program (which may also be referred to or described as a program, software, a software application, a module, a software module, a script, or code) can be written in any form of programming language, including compiled or interpreted languages, or declarative or procedural languages, and it can be deployed in any form, including as a stand alone program or as a module, component, subroutine, or other unit suitable for use in a computing environment. A computer program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub programs, or portions of code. A computer program can be deployed to be executed on one computer or on multiple computers that are located at one site or distributed across multiple sites and interconnected by a communication network.

As used in this specification, an "engine," or "software engine," refers to a software implemented input/output system that provides an output that is different from the input. An engine can be an encoded block of functionality, such as a library, a platform, a software development kit ("SDK"), or an object. Each engine can be implemented on any appropriate type of computing device, e.g., servers, mobile phones, tablet computers, notebook computers, music players, e-book readers, laptop or desktop computers, PDAs, smart phones, or other stationary or portable devices, that includes one or more processors and computer readable media. Additionally, two or more of the engines may be implemented on the same computing device, or on different computing devices.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit).

Computers suitable for the execution of a computer program include, by way of example, can be based on general or special purpose microprocessors or both, or any other kind of central processing unit. Generally, a central processing unit will receive instructions and data from a read only memory or a random access memory or both. The essential elements of a computer are a central processing unit for performing or executing instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

Embodiments of the subject matter described in this specification can be implemented in a computing system that includes a back end component, e.g., as a data server, or that includes a middleware component, e.g., an application server, or that includes a front end component, e.g., a client computer having a graphical user interface or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), e.g., the Internet.

The computing system can include clients and servers. A client and server are generally remote from each other and typically interact through a communication network. The relationship of client and server arises by virtue of computer programs running on the respective computers and having a client-server relationship to each other.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. An electrode array for epidural stimulation comprising:
an elongated substrate having a central longitudinal axis;
a first group of inner electrodes arranged on the substrate along a first serpentine path that undulates laterally back and forth across a first inner longitudinal axis from a first end of the substrate to a second end of the substrate thereby conforming the first group of inner electrodes to the locations of a first set of spinal cord rootlets when the electrode array is positioned over the spinal cord, the first inner longitudinal axis parallel to the central longitudinal axis; and
a second group of inner electrodes arranged on the substrate along a second serpentine path that undulates laterally back and forth across a second inner longitudinal axis from the first end of the substrate to the second end of the substrate thereby conforming the second group of inner electrodes to the locations of a second set of spinal cord rootlets when the electrode array is positioned over the spinal cord, the second inner longitudinal axis parallel to the central longitudinal axis.

2. The electrode array of claim 1, wherein the second group of inner electrodes is symmetrical to the first group of inner electrodes with respect to the central longitudinal axis.

3. The electrode array of claim 1, further comprising:
   a first group of outer electrodes arranged on the substrate along a third serpentine path that undulates laterally back and forth across a first outer longitudinal axis from the first end of the substrate to the second end of the substrate, the first outer longitudinal axis parallel to the first inner longitudinal axis, the first inner longitudinal axis positioned between the central longitudinal axis and the first outer longitudinal axis; and
   a second group of outer electrodes arranged on the substrate along a fourth serpentine path that undulates laterally back and forth across a second outer longitudinal axis from the first end of the substrate to the second end of the substrate, the second outer longitudinal axis parallel to the second inner longitudinal axis, the second inner longitudinal axis positioned between the central longitudinal axis and the second outer longitudinal axis.

4. The electrode array of claim 3, wherein the second group of outer electrodes is symmetrical to the first group of outer electrodes with respect to the central longitudinal axis.

5. The electrode array of claim 3, comprising a plurality of sections arranged longitudinally along the substrate, each section defining a different respective set of electrodes from the first and second groups of outer electrodes that can be selectively activated independent of the respective sets of electrodes in other sections; and
   wherein, in each of the sections, respective set of electrodes in that section are spaced equally along the first and second outer longitudinal axes.

6. The electrode array of claim 3, comprising a plurality of sections arranged longitudinally along the substrate, each section defining a different respective set of electrodes from the first and second groups of outer electrodes that can be selectively activated independent of the respective sets of electrodes in other sections;
   wherein, in each of the sections, at least one pair of adjacent electrodes are spaced at a different distance from at least another pair of adjacent electrodes in that section; and
   wherein, in each of the sections, at least one pair of adjacent electrodes are spaced at a different distance from at least another pair of adjacent electrodes in that section.

7. The electrode array of claim 3, wherein the arrangement of the first group of inner electrodes, the second group of inner electrodes, the first group of outer electrodes, and the second group of outer electrodes along the first, second, third, and fourth serpentine paths, respectively, provides a variable contact density of electrodes along a length of the substrate.

8. The electrode array of claim 7, wherein the variable contact density is defined at least by a low electrode density region along the length of the substrate, a medium electrode density region along the length of the substrate, and a high electrode density region along the length of the substrate, wherein each of the low, medium, and high density regions comprise multiple electrodes from the first group of inner electrodes, multiple electrodes from the second group of inner electrodes, multiple electrodes from the first group of outer electrodes, and multiple electrodes from the second group of outer electrodes.

9. The electrode array of claim 1, comprising a plurality of sections arranged longitudinally along the substrate, each section defining a different respective set of electrodes from the first and second groups of inner electrodes that can be selectively activated independent of the respective sets of electrodes in other sections; and
   wherein, in each of the sections, the respective set of electrodes in that section are spaced equally along the first and second inner longitudinal axes.

10. The electrode array of claim 1, comprising a plurality of sections arranged longitudinally along the substrate, each section defining a different respective set of electrodes from the first and second groups of inner electrodes that can be selectively activated independent of the respective sets of electrodes in other sections;
    wherein, in each of the sections, at least one pair of adjacent electrodes are spaced at a different distance from at least another pair of adjacent electrodes in that section; and
    wherein, in each of the sections, at least one pair of adjacent electrodes are spaced at a different distance from at least another pair of adjacent electrodes in that section.

11. The electrode array of claim 9, wherein adjacent electrodes within each section are spaced closer to each other than adjacent electrodes in adjacent sections.

12. The electrode array of claim 1, further comprising:
    a plurality of central electrodes arranged on the substrate along the central longitudinal axis.

13. The electrode array of claim 12, wherein the plurality of central electrodes includes four central electrodes spaced along a length of the substrate.

14. The electrode array of claim 1, wherein the arrangement of the first group of inner electrodes and the second group of inner electrodes along the first serpentine path and the second serpentine path, respectively, provides a variable contact density of electrodes along a length of the substrate.

15. The electrode array of claim 14, wherein the variable contact density is defined at least by a low electrode density region along the length of the substrate, a medium electrode density region along the length of the substrate, and a high electrode density region along the length of the substrate, wherein each of the low, medium, and high density regions comprise multiple electrodes from the first group of inner electrodes and multiple electrodes from the second group of inner electrodes.

16. The electrode array of claim 1, wherein the substrate is configured to have lateral outlines that follow curved lines defined by an undulating arrangement of electrodes on the substrate.

17. The electrode array of claim 16, wherein the lateral outlines of the substrate comprise lateral edges of the substrate that follow curved lines defined by an undulating arrangement of outer electrodes on the substrate.

* * * * *